United States Patent
Maeda et al.

(10) Patent No.: US 7,622,469 B2
(45) Date of Patent: Nov. 24, 2009

(54) 2,4-DIAMINO-1,3,5-TRIAZINE DERIVATIVES

(75) Inventors: Shirou Maeda, Nagaokakyo (JP); Toshiko Kita, Takatsuki (JP); Kanji Meguro, Nishinomiya (JP)

(73) Assignee: Hamari Chemicals, Ltd., Osaka (JP)

( * ) Notice: Subject to any disclaimer, the term of this patent is extended or adjusted under 35 U.S.C. 154(b) by 326 days.

(21) Appl. No.: 10/539,234

(22) PCT Filed: Dec. 16, 2003

(86) PCT No.: PCT/JP03/16131

§ 371 (c)(1),
(2), (4) Date: Jul. 15, 2005

(87) PCT Pub. No.: WO2004/054989

PCT Pub. Date: Jan. 7, 2004

(65) Prior Publication Data

US 2006/0154928 A1 Jul. 13, 2006

(30) Foreign Application Priority Data

| Dec. 17, 2002 | (JP) | 2002-365927 |
| Oct. 23, 2003 | (JP) | 2003-363820 |

(51) Int. Cl.
| A61K 31/53 | (2006.01) |
| A01N 43/66 | (2006.01) |
| A61K 31/47 | (2006.01) |
| A01N 43/42 | (2006.01) |
| C07D 251/00 | (2006.01) |
| C07D 251/10 | (2006.01) |

(52) U.S. Cl. ............... 514/245; 514/241; 514/246; 514/311; 544/204; 544/208; 544/209

(58) Field of Classification Search ............... 544/204, 544/208; 514/245
See application file for complete search history.

(56) References Cited

U.S. PATENT DOCUMENTS

| 3,168,519 | A | | 2/1965 | Nagy |
| 3,287,365 | A | | 11/1966 | Newman et al. |
| 3,287,366 | A | * | 11/1966 | Newman et al. ............ 544/206 |
| 3,563,988 | A | | 2/1971 | Feichtinger et al. |
| 5,565,451 | A | | 10/1996 | Peake et al. |
| 7,034,021 | B2 | * | 4/2006 | Moinet et al. ............... 514/245 |
| 2003/0109530 | A1 | | 6/2003 | Moinet et al. |

FOREIGN PATENT DOCUMENTS

| JP | 45-41591 | 12/1970 |
| WO | 99/01442 | 1/1999 |
| WO | 00/32580 | 6/2000 |
| WO | 01/055122 | 8/2001 |
| WO | WO 01/55122 A1 * | 8/2001 |
| WO | 2004/087153 | 10/2004 |

OTHER PUBLICATIONS

Edward J. Modest and Philip Levine, "Chemical and Biological Studies on 1,2-Dihyrdo-s-triazines. III. Two-Component Synthesis", Journal of Organic Chemistry, 1956, 21(1), 14-20.*
H.C. Carrington, A.F. Crowther, D.G. Davey, A.A. Levi, and F.L. Rose, "A Metabolite of 'Paludrine' with High Antimalarial Activity", Nature, 1951, 168, 1080.*
R. J. A. Walsh et al., "The Structure Activity Relationship of Antibacterial Substituted 1-Phenyl-4,6-Diamino-1,2-Dihydro-2,2-Dimethyl-s-triazines", Eur. J. Med. Chem., vol. 12, No. 6, pp. 495-500, Nov.-Dec. 1977.
M. S. Bartlett et al., "Evaluation of Potent Inhibitors of Dihydrofolate Reductase in a Culture Model for Growth of Pneumocystis carinii", Antimicrobial Agents and Chemotherapy, pp. 2436-2441, vol. 39, No. 11, Nov. 1995.
L. Chio et al., "Identification of Highly Potent and Selective Inhibitors of Toxoplasma gondii Dihydrofolate Reductase", Antimicrobial Agents and Chemotherapy, vol. 37, No. 9, pp. 1914-1923, Sep. 1993.
H. M. Eisa et al., "Synthesis of certain 2-aminoadamantane derivatives as potential antimicrobial agents", Pharmazie, vol. 46, No. 3, pp. 182-184, 1991.
H. M. Eisa et al., "Synthesis and Antimicrobial Testing of 2-Amino-4-(p-Fluro-m-Nitroanilino)-6-Substituted-s-Triazines", Pakistan J. Sci. Ind. Res., vol. 31, No. 7, pp. 474-478, Jul. 1988.
E. A. Coats et al., "Quantitative Structure-Activity Relationship of Antifolate Inhibition of Bacteria Cell Cultures Resistant and Sensitive to Methotrexate", J. Med. Chem. vol. 28, No. 12, pp. 1910-1916, 1985.
B. Testa et al., "Steric and Lipophobic Components of the Hydrophobic Fragmental Constant", Drug Res., vol. 31, No. 7, pp. 1053-1058, 1981.
C. S. Genther et al., "Antifolate Studies. Activities of 40 Potential Antimalarial Compounds against Sensitive and Chlorguanide Triazine Resistant Strains of Folate-Requiring Bacteria and Escherichia coi", Journal of Medicinal Chemistry, vol. 20, No. 2, pp. 237-243, 1977.

(Continued)

Primary Examiner—Johann R Richter
Assistant Examiner—Nathan W Schlientz
(74) Attorney, Agent, or Firm—Wenderoth, Lind & Ponack, L.L.P.

(57) ABSTRACT

The present invention relates to an antibacterial agent, which comprises, as an active ingredient, a compound represented by the following general formula (1):

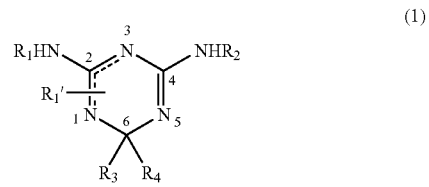

or a pharmaceutically acceptable salt thereof.

6 Claims, No Drawings

OTHER PUBLICATIONS

B. R. Baker, "Differential Binding to the Hydrophobic Bonding Region of $T_2$ Phage Induced, *Escherichia coli* B, and Pigeon Liver Dihydrofolic Reductases[1,2]", Journal of Medicinal Chemistry, vol. 10, No. 5, pp. 912-917, Sep. 1967.

T. Seo et al., "Syntheses and Properties of Polyguanamine from Diester and Bisbiguanide", Nippon Kagaku Kaishi, No. 12, pp. 2419-2424, 1974, in Japanese language with English abstract.

A. Rosowsky et al., "Structure-Activity and Structure-Selectivity Studies on Diaminoquinazolines and other Inhibitors of *Pneumocystis carinii* and *Toxoplasma gondii* Dihydrofolate Reductase", Antimicrobial Agents and Chemotherapy, vol. 39, No. 1, pp. 79-86, Jan. 1995.

W. R. Turner et al., "Novel Bis[1,6-dihydro-6,6-dimethyl-1,3,5-triazine-2,4-diamines] as Antitrypanosomal Agents[1,2]", J. Med. Chem., vol. 28, No. 11, pp. 1728-1740, 1985.

Partial Supplementary European Search Report issued Sep. 25, 2007 in the European Application No. 03780808.6-1211, PCT/JP0316131, of which the present application in the U.S. National Stage.

Foley, G.E. et al., "A Comparative Study of the Use of Microoraganisms in the Screening of Potential Antitumor Agents", Annals of The New York Academy of Science, New York, NY, US, vol. 76, No. 3, pp. 413-441.

* cited by examiner

2,4-DIAMINO-1,3,5-TRIAZINE DERIVATIVES

This application is a U.S. national stage of International Application No. PCT/JP2003/016131 filed Dec. 16, 2003.

TECHNICAL FIELD

The present invention relates to a novel antibacterial agent and a novel 2,4-diamino-1,3,5-triazine derivative.

BACKGROUND ART

Many infectious diseases have been overcome by development of various bactericides/disinfectants, antibiotics, and synthetic antibacterial agents, and the average life span of human beings has been considerably extended. On the other hand, however, many bacteria resistant to these drugs appear and, at the same time, in elderly people, so-called opportunistic infection with bacteria which are usually weak in their infectious power has been increased due to a cause such as reduction in immunity, and increase in hospital infection and population infection in other facilities has become a great social problem. Especially in recent years, infectious diseases which cannot be treated by conventional drugs, including those caused by methicillin-resistant *Staphylococcus aureus* (MRSA) and vancomycin-resistant enterococci (VRE) or, nowadays those caused by vancomycin-resistant MRSA, multiple drug-resistant *Pseudomonas aeruginosa, pneumococcus* and *Serratia bacteria*, have increased rapidly, and development of effective methods of preventing or treating such diseases is now keenly desired.

Since the discovery of 4,6-diamino-1-(p-chlorophenyl)-1, 2-dihydro-2,2-dimethyl-s-triazine (Cycloguanil) which is an active metabolite of an anti-malaria agent Proguanil fifty several years ago (Journal of Pharmacology 1947, Vol. 2, p. 161-168; British H. C. Carrington et al., Nature 1951, Vol. 168, p. 1080), various patent applications or study reports have been made.

For example, E. J. Modest et al., Journal of the American Chemical Society 1952, Vol. 74, p. 855-856 describes antivitamin activity and anti-malaria activity of 4,6-diamino-2,2-dimethyl-s-triazine derivatives. E. J. Modest et al., Journal of Organic Chemistry 1956, Vol. 21, p. 1-13, p. 14-20 describes 4,6-diamino-1,2-dihydro-2,2-dimethyl-1-phenyl-s-triazines regarding anti-vitamin, anti-malaria, anti-cancer and anti-coccidium activities. U.S. Pat. No. 5,565,451 describes the use of 1-(3-phenylpropyl)-2,4-diamino-6,6-dimethyl-1,6-dihydro-1,3,5-triazines as an insecticide. EP No. 0504290 describes that 4,6-diamino-1,2-dihydro-1-phenyl-s-triazines have an action of inhibiting growth of *Pneumocystic carinii*. WO 01/53276 describes the use of 1-p-chlorophenyl-4,6-diamino-1,2-dihydro-1,3,5-triazine and the like as an anthelmintic (anti-malaria agent etc.). However, the aforementioned known references do not refer to antibacterial activity at all.

U.S. Pat. No. 3,682,912 describes 4,6-diamino-1,2-dihydro-1,3,5-triazine derivatives as a compound having antibacterial activity in addition to anti-malaria activity, and U.S. Pat. No. 3,723,429 describes 4,6-diamino-1,2-dihydro-1,3,5-triazine derivatives as an anti-malaria/antibacterial active compound. However, since compounds described in these known references have all a substituent at position 1 of the 1,2-dihydro-1,3,5-triazine ring using —O— as an intervening group, they are different compounds from those of the present invention, and no data of antibacterial activity are described therein.

U.S. Pat. No. 3,287,365 describes a compound represented by the following formula (4) having herbicidal activity in Working Example 5, but antibacterial activity thereof is not described at all.

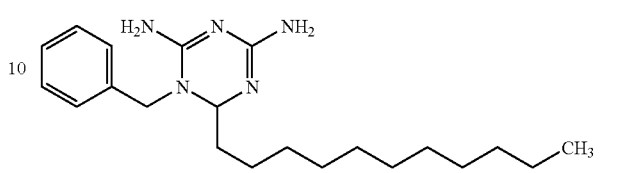

(4)

U.S. Pat. No. 3,287,366 describes a compound represented by the following formula (5) having herbicidal activity in Working Example 3, but nothing is known about antibacterial activity thereof.

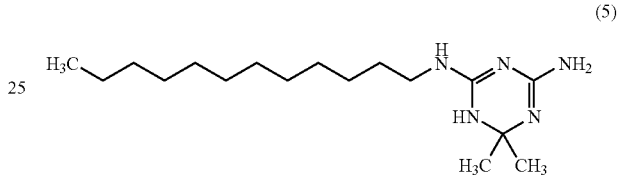

(5)

Andre Rosowsky et al., Antimicrobial Agents and Chemotherapy 1995, Vol. 39, p. 79-86 describes a compound represented by the following formula (6) as a dehydrofolate reductase inhibitor (anthelmintic (anti-malaria)). However, the aforementioned known reference does not describe antibacterial activity of the same compound at all.

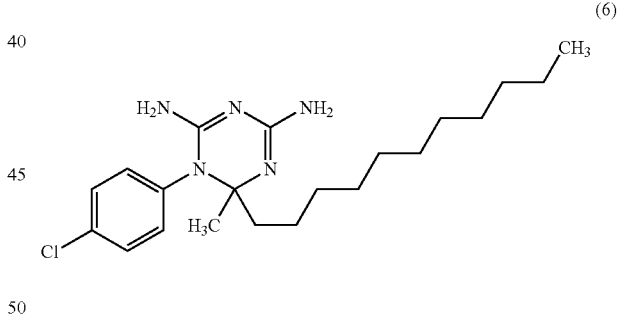

(6)

DISCLOSURE OF THE INVENTION

An object of the present invention is to provide a novel antibacterial agent containing, as an active ingredient, a 2,4-diamino-1,3,5-triazine derivative or a pharmacologically acceptable salt thereof. Another object of the present invention is to provide novel 2,4-diamino-1,3,5-triazine derivatives or pharmacologically acceptable salts thereof.

In order to attain the aforementioned objects, the present inventors have created novel triazine derivatives and investigated physiological activity thereof and, as a result, found that 2,4-diamino-1,3,5-triazine derivatives or pharmacologically acceptable salts thereof have a wide range of strong growth inhibiting effect and bactericidal effect against Gram-positive and Gram-negative bacteria. Based on these findings, the present invention has been completed.

That is, the present invention relates to:

1) An antibacterial agent, which comprises, as an active ingredient, a compound represented by the following general formula (1):

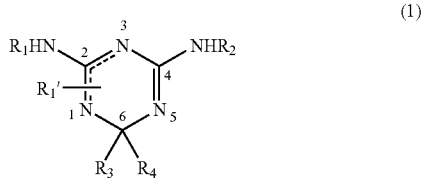

(wherein $R_1$ represents (i) a hydrogen atom, (ii) a phenyl group or a phenylalkyl group, each of which is optionally substituted, (iii) a naphthyl group or a naphthylalkyl group, each of which is optionally substituted, (iv) a heterocyclic group, a heterocyclic alkyl group or a heterocyclic aminoalkyl group, each of which is optionally substituted, (v) an optionally substituted alkyl group of 1 to 16 carbon atoms, or (vi) a cycloalkyl group or a cycloalkyl-alkyl group, each of which is optionally substituted;

(a) when $R_1$ is a hydrogen atom, $R_1'$ represents (i) a phenyl group or a phenylalkyl group, each of which is optionally substituted, (ii) a naphthyl group or a naphthylalkyl group, each of which is optionally substituted, (iii) a heterocyclic group, a heterocyclic alkyl group or a heterocyclic aminoalkyl group, each of which is optionally substituted, (iv) an optionally substituted alkyl group of 1 to 16 carbon atoms, or (v) a cycloalkyl group or a cycloalkyl-alkyl group, each of which is substituted, said groups (i) to (v) being substituted at position 1 of the dihydrotriazine ring, or (b) when $R_1$ is other than a hydrogen atom, $R_1'$ represents a hydrogen atom attached to the nitrogen atom at position 1 or 3 of the dihydrotriazine ring;

$R_2$ represents a hydrogen atom or an optionally substituted alkyl group of 1 to 16 carbon atoms;

$R_3$ and $R_4$ represent that $R_3$ is a hydrogen atom or an optionally substituted alkyl group of 1 to 3 carbon atoms, and $R_4$ is a hydrogen atom or an optionally substituted alkyl group of 1 to 16 carbon atoms, or $R_3$ and $R_4$ are taken together with the adjacent carbon atom to form a spirocycloalkane group or an alkyl spirocycloalkane group; and the dashed line indicates that the position of a double bond is either between 1 and 2 or between 2 and 3), or a tautomer thereof or a pharmacologically acceptable salt thereof, 2) The antibacterial agent according to the above 1), wherein any one of $R_2$ and $R_4$ is an optionally substituted alkyl group of 7 to 16 carbon atoms, 3) A compound represented by the general formula (1a):

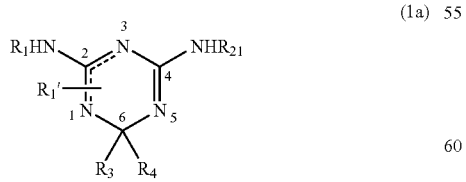

(wherein $R_1$ represents (i) a hydrogen atom, (ii) a phenyl group or a phenylalkyl group, each of which is optionally substituted, (iii) a naphthyl group or a naphthylalkyl group, each of which is optionally substituted, (iv) a heterocyclic group, a heterocyclic alkyl group or a heterocyclic aminoalkyl group, each of which is optionally substituted, (v) an optionally substituted alkyl group of 1 to 16 carbon atoms, or (vi) a cycloalkyl group or a cycloalkyl-alkyl group, each of which is optionally substituted;

(a) when $R_1$ is a hydrogen atom, $R_1'$ represents (i) a phenyl group or a phenylalkyl group, each of which is optionally substituted, (ii) a naphthyl group or a naphthylalkyl group, each of which is optionally substituted, (iii) a heterocyclic group, a heterocyclic alkyl group or a heterocyclic aminoalkyl group, each of which is optionally substituted, (iv) an optionally substituted alkyl group of 1 to 16 carbon atoms,(v) a cycloalkyl group or a cycloalkyl-alkyl group, each of which is optionally substituted, said groups (i) to (v) being substituted at position 1 of the dihydrotriazine ring, or (b) when $R_1$ is other than a hydrogen atom, $R_1'$ represents a hydrogen atom attached to the nitrogen atom at position 1 or 3 of the dihydrotriazine ring;

$R_{21}$ represents an optionally substituted alkyl group of 7 to 16 carbon atoms;

$R_3$ and $R_4$ represent that $R_3$ is a hydrogen atom or an optionally substituted alkyl group of 1 to 3 carbon atoms, and $R_4$ is a hydrogen atom or an optionally substituted alkyl group of 1 to 16 carbon atoms, or $R_3$ and $R_4$ are taken together with the adjacent carbon atom to form a spirocycloalkane group or an alkyl spirocycloalkane group; and the dashed line indicates that the position of a double bond is either between 1 and 2 or between 2 and 3), or a tautomer thereof or a salt thereof, 4) The compound according to the above 3), wherein $R_1$ is (i) a hydrogen atom, (ii) a phenyl group or a phenylalkyl group, each of which is optionally substituted, (iii) an optionally substituted naphthyl group, (iv) a heterocyclic group, a heterocyclic alkyl group or a heterocyclic aminoalkyl group, each of which is optionally substituted, (v) an optionally substituted alkyl group of 1 to 16 carbon atoms, or (vi) a cycloalkyl group or a cycloalkyl-alkyl group, each of which is optionally substituted;

(a) when $R_1$ is a hydrogen atom, $R_1'$ is (i) a phenyl group or a phenylalkyl group, each of which is optionally substituted, (ii) a naphthyl group or a naphthylalkyl group, each of which is optionally substituted, (iii) a heterocyclic group, a heterocyclic alkyl group or a heterocyclic aminoalkyl group, each of which is optionally substituted, or (iv) an optionally substituted alkyl group of 1 to 16 carbon atoms, said groups (i) to (iv) being substituted at position 1 of the dihydrotriazine ring, or a tautomer thereof or a salt thereof, 5) The compound according to the above 3), wherein $R_1$ is a phenyl group or a phenylalkyl group, or an alkyl group of 1 to 16 carbon atoms, each of which is optionally substituted; $R_3$ is an optionally substituted alkyl group of 1 to 3 carbon atoms; and $R_4$ is an optionally substituted alkyl group of 1 to 16 carbon atoms, or a tautomer thereof or a salt thereof, 6) A compound represented by the following general formula (1b):

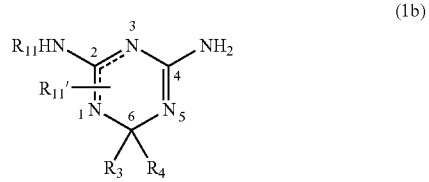

(wherein $R_{11}$ represents (i) a hydrogen atom, (ii) an optionally substituted phenyl group, (iii) a naphthyl group or a naphthylalkyl group, each of which is optionally substituted, (iv) a heterocyclic group or a heterocyclic alkyl group, each of which is optionally substituted, or (v) a cycloalkyl group or a cycloalkyl-alkyl group, each of which is optionally substituted;

(a) when $R_{11}$ is a hydrogen atom, $R_{11}'$ represents (i) a naphthyl group or a naphthylalkyl group, each of which is optionally substituted, (ii) a heterocyclic group or a heterocyclic alkyl group, each of which is optionally substituted, (iii) an optionally substituted alkyl group of 1 to 16 carbon atoms, or (iv) a cycloalkyl group or a cycloalkyl-alkyl group, each of which is optionally substituted, said groups (i) to (iv) being substituted at position 1 of the dihydrotriazine ring, or (b) when $R_{11}$ is other than a hydrogen atom, $R_{11}'$ represents a hydrogen atom attached to the nitrogen atom at position 1 or 3 of the dihydrotriazine ring;

$R_3$ and $R_4$ represent that $R_3$ is a hydrogen atom or an alkyl group of 1 to 3 carbon atoms, and $R_4$ is a hydrogen atom or an alkyl group of 1 to 16 carbon atoms, or $R_3$ and $R_4$ are taken together with the adjacent carbon atom to form a spirocycloalkane group or an alkyl spirocycloalkane group; and the dashed line indicates that the position of a double bond is either between 1 and 2 or between 2 and 3, provided that at least one of $R_{11}'$ and $R_4$ is an optionally substituted alkyl group of 7 to 16 carbon atoms), or a tautomer thereof or a salt thereof, 7) The compound according to the above 6), wherein $R_{11}$ is an optionally substituted phenyl group, or a tautomer thereof or a salt thereof, 8) A compound represented by the following general formula (1c):

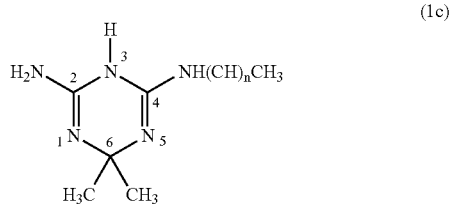

(wherein n represents an integer of 13 to 15), or a tautomer thereof or a salt thereof, 9) A compound represented by the following general formula (1d):

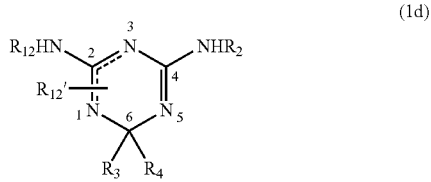

(wherein $R_{12}$ represents a hydrogen atom, or a heterocyclic group, a heterocyclic alkyl group or a heterocyclic aminoalkyl group, the last three groups being optionally substituted, (a) when $R_{12}$ is a hydrogen atom, $R_{12}'$ represents an optionally substituted heterocyclic group, an optionally substituted heterocyclic alkyl group or an optionally substituted heterocyclic aminoalkyl group, said groups being substituted at position 1 of the dihydrotriazine ring, or (b) when $R_{12}$ is other than a hydrogen atom, $R_{12}'$ represents a hydrogen atom attached to the nitrogen atom at position 1 or 3 of the dihydrotriazine ring;

$R_2$ represents a hydrogen atom, or an optionally substituted alkyl group of 1 to 16 carbon atoms;

$R_3$ and $R_4$ represent that $R_3$ is a hydrogen atom or an optionally substituted alkyl group of 1 to 3 carbon atoms, and $R_4$ is a hydrogen atom or an optionally substituted alkyl group of 1 to 16 carbon atoms, or $R_3$ and $R_4$ are taken together with the adjacent carbon atom to form a spirocycloalkane group or an alkyl spirocycloalkane group; and the dashed line indicates that the position of a double bond is either between 1 and 2 or between 2 and 3), or a tautomer thereof or a salt thereof, 10) A bactericidal/disinfectant agent, which comprises, as an active ingredient, a compound represented by the general formula (1) as defined in the above 1), or a tautomer thereof or a pharmacologically acceptable salt thereof, 11) An antiseptic/preservative agent for cosmetics, which comprises, as an active ingredient, a compound represented by the general formula (1) as defined in the above 1), or a tautomer thereof or a pharmacologically acceptable salt thereof, 12) A method of treating or preventing bacterial infectious diseases, which comprises administering a therapeutically effective amount of a compound represented by the general formula (1) as defined in the above 1), or a tautomer thereof or a pharmacologically acceptable salt thereof to mammals, birds or fish in need of treatment or prevention of bacterial infectious diseases, and 13) Use of a compound represented by the general formula (1) as defined in the above 1), or a tautomer thereof or a pharmacologically acceptable salt thereof for preparation of a medicament for treating or preventing bacterial infectious diseases.

Since the compounds (1) which are an active ingredient of the present invention have strong antibacterial activity and bactericidal activity, they are extremely useful as antibacterial agents or bactericides/disinfectants.

BEST MODE FOR CARRYING OUT THE INVENTION

The compounds used in the present invention represented by the formula (1), and the compounds represented by the formulae (1a), (1b) and (1d) will be explained in detail below.

Each substituent in the formula (1) will be explained.

The substituent $R_1$ is (i) a hydrogen atom, (ii) a phenyl group or a phenylalkyl group, each of which is optionally substituted, (iii) a naphthyl group or a naphthylalkyl group, each of which is optionally substituted, (iv) a heterocyclic group, a heterocyclic alkyl group, or a heterocyclic aminoalkyl group, each of which is optionally substituted, (v) an optionally substituted alkyl group of 1 to 16 carbon atoms or (vi) a cycloalkyl group or a cycloalkyl-alkyl group, each of which is optionally substituted.

Herein, examples of the "phenylalkyl group" include a group in which a linear or branched alkyl group of 1 to 6 carbon atoms is attached to a phenyl group, and preferable examples include benzyl, 1-phenylethyl, 2-phenylethyl, 1-phenylpropyl, 2-phenylpropyl and 3-phenylpropyl.

Examples of the "naphthyl group" include 1-naphthyl and 2-naphthyl.

Examples of the "naphthylalkyl group" include a group in which a linear or branched alkyl group of 1 to 6 carbon atoms is attached to a naphthyl group, and preferable examples include 1-naphthylmethyl, 2-naphthylmethyl, 1-naphthylethyl and 2-naphthylethyl.

Examples of the "heterocyclic group" include a 3 to 6-membered heterocyclic group containing 1 to 3 atoms selected from a nitrogen atom, an oxygen atom and a sulfur atom, to which a benzene ring may be fused, and examples include pyridyl such as 2-pyridyl, 3-pyridyl and 4-pyridyl; pyrazinyl; furyl such as 2-furyl; thiazolyl such as 2-thiazolyl; piperidyl such as 1-piperidyl; piperazyl such as 1-piperazyl; tetrahydrofuryl; 2-oxotetrahydrofuryl; thienyl; pyrrolyl; pyrrolidinyl; oxazolyl; imidazolyl; isooxazolyl; isothiazolyl; pyrazolyl; tetrahydropyranyl; 2-oxotetrahydropyranyl; pyrimidinyl; pyridazinyl; morpholinyl; 1,3,5-triazinyl; 1,2,4-triazinyl; quinolyl such as 2-quinolyl, 3-quinolyl, 4-quinolyl, 5-quinolyl and 8-quinolyl; and isoquinolyl such as 1-isoquinolyl, 3-isoquinolyl, 4-isoquinolyl and 5-isoquinolyl.

Examples of the "heterocyclic alkyl group" include a group in which a linear or branched alkyl group of 1 to 6 carbon atoms is attached to the aforementioned heterocyclic group, and preferable examples include 2-pyridylmethyl, 3-pyridylmethyl, 4-pyridylmethyl, 2-pyridylethyl, 3-pyridylethyl, 4-pyridylethyl, pyrazinylmethyl, pyrazinylethyl, 2-furylmethyl, 2-furylethyl, 2-thiazolylmethyl, 2-thiazolylethyl, 4-piperidylmethyl, 2-quinolylmethyl, 3-quinolylmethyl, 4-quinolylmethyl, 5-quinolylmethyl, 8-quinolylmethyl, 1-isoquinolylmethyl, 3-isoquinolylmethyl, 4-isoquinolylmethyl and 5-isoquinolylmethyl.

Examples of the "heterocyclic aminoalkyl group" include a group in which a linear or branched alkyl group of 1 to 12 carbon atoms is attached to a heterocyclic amino group, and preferable examples include a 4-amino-dihydro-1,3,5-triazin-2-ylamino group, a 4-alkylamino-dihydro-1,3,5-triazin-2-ylamino group and a 4-phenylalkylamino-dihydro-1,3,5-triazin-2-ylamino group.

Examples of the "alkyl group of 1 to 16 carbon atoms" include a linear or branched alkyl group, and preferable examples include methyl, ethyl, n-propyl, isopropyl, n-butyl, isobutyl, sec-butyl, tert-butyl, n-hexyl, n-heptyl, n-octyl, tert-octyl, n-nonyl, n-decyl, n-undecyl, n-dodecyl, n-tridecyl, n-tetradecyl, n-pentadecyl, and n-hexadecyl.

Examples of the "cycloalkyl group" include a cycloalkyl group of 3 to 6 carbon atoms, and examples include cyclopropyl, cyclobutyl, cyclopentyl and cyclohexyl.

Examples of the "cycloalkyl-alkyl group" include a group in which a linear or branched alkyl group of 1 to 6 carbon atoms is attached to the aforementioned cycloalkyl group, and preferable examples include cyclohexylmethyl, 1-cyclohexylethyl and 2-cyclohexylethyl.

A benzene ring of the phenyl group or the phenylalkyl group; a naphthalene ring of the naphthyl group or the naphthylalkyl group; a heterocyclic ring of the heterocyclic group, the heterocyclic alkyl group or the heterocyclic aminoalkyl group; an alkyl group of 1 to 16 carbon atoms; a cycloalkyl group of the cycloalkyl group or of the cycloalkyl-alkyl group may have a substituent. Examples of such substituents include a halogen atom, a hydroxy group, a nitro group, a cyano group, a $C_{1-6}$ alkyl group, a $C_{1-6}$ haloalkyl group, a $C_{3-6}$ cycloalkyl group, a $C_{6-10}$ aryl group, a $C_{6-10}$ aryloxy group, a $C_{1-6}$ alkoxy group, a $C_{1-6}$ haloalkoxy group, a $C_{3-6}$ cycloalkyloxy group, a $C_{1-7}$ alkanoyl group, a carboxyl group, a carbamoyl group, a $C_{2-7}$ alkoxycarbonyl group, a $C_{2-7}$ haloalkoxycarbonyl group, a $C_{7-11}$ aryloxycarbonyl group, a $C_{4-7}$ cycloalkyloxycarbonyl group, an amino group, a $C_{1-6}$ alkylamino group, a $C_{1-6}$ haloalkylamino group, di-$C_{1-6}$ alkylamino group, a $C_{1-7}$ alkanoylamino group, a cyclic amino group, a $C_{2-7}$ alkylaminocarbonyl group, a mercapto group, a sulfonic acid group, a sulfonamido group, a $C_{1-6}$ alkylthio group, a $C_{1-6}$ haloalkylthio group, a $C_{1-6}$ alkylsulfonyl group, a $C_{1-6}$ haloalkylsulfonyl group, a $C_{1-6}$ alkylsulfonyloxy group, a $C_{1-6}$ haloalkylsulfonyloxy group, a $C_{1-6}$ alkylslfonylamino group, and a $C_{1-6}$ haloalkylsulfonylamino group. About 1 to 6, preferably 1 to 3, substituent(s) may be attached to the same or different chemically acceptable arbitrary positions.

Examples of the "halogen atom" include a fluorine atom, a chlorine atom, a bromine atom and an iodine atom.

The "$C_{1-6}$ alkyl group" maybe linear or branched, and examples thereof include methyl, ethyl, n-propyl, isopropyl, n-butyl, isobutyl, sec-butyl, tert-butyl, n-pentyl, sec-pentyl, isopentyl, neopentyl, n-hexyl and isohexyl.

Examples of the "$C_{1-6}$ haloalkyl group" include chloromethyl, bromomethyl, 1-chloroethyl and trifluoromethyl.

Examples of the "$C_{3-6}$ cycloalkyl group" include cyclopropyl, cyclobutyl, cyclopentyl and cyclohexyl. Examples of the "$C_{6-10}$ aryl group" include phenyl and naphthyl, preferably phenyl.

Examples of the "$C_{6-10}$ aryloxy group" include phenyloxy and naphthyloxy, preferably phenyloxy.

Examples of the "$C_{1-6}$ alkoxy group" include methoxy, ethoxy, n-propoxy, isopropoxy, n-butoxy and isobutoxy.

Examples of the "$C_{1-6}$ haloalkoxy group" include trifluoromethoxy.

Examples of the "$C_{3-6}$ cycloalkyloxy group" include cyclopropyloxy, cyclobutyloxy, cyclopentyloxy and cyclohexyloxy.

Examples of the "$C_{1-7}$ alkanoyl group" include formyl, acetyl, propionyl, butyryl, isobutyryl, pentanoyl and hexanoyl.

Examples of the "$C_{2-7}$ alkoxycarbonyl group" include a group which is made through ester bond formation between a linear or branched alkyl group of 1 to 6 carbon atoms, preferably 1 to 4 carbon atoms, and a carboxyl group, and examples include methoxycarbonyl, ethoxycarbonyl, n-propoxycarbonyl, isopropoxycarbonyl, n-propoxycarbonyl and isobutoxycarbonyl.

Examples of the "$C_{2-7}$ haloalkoxycarbonyl group" include chloromethoxycarbonyl, bromomethoxycarbonyl and (1-chloro)ethoxycarbonyl.

Examples of the "$C_{4-7}$ cycloalkyloxycarbonyl group" include cyclopropoxycarbonyl and cyclopentyloxycarbonyl.

Examples of the "$C_{7-11}$ aryloxycarbonyl group" include phenyloxycarbonyl and naphthaleneoxycarbonyl.

Examples of the "$C_{1-6}$ alkylamino group" include methylamino, ethylamino, n-propylamino, isopropylamino, sec-butylamino and n-pentylamino.

Examples of the "di-$C_{1-6}$ alkylamino group" include dimethylamino, diethylamino and methylethylamino.

Examples of the "$C_{1-6}$ haloalkylamino group" include trifluoromethylamino.

Examples of the "$C_{1-7}$ alkanoylamino group" include a substituent in which an amino group is attached to the aforementioned $C_{1-7}$ alkanoyl group.

Examples of the "cycloamino group" include a morpholino group.

Examples of the "$C_{2-7}$ alkylamino carbonyl group" include a substituent in which a carbonyl group is attached to the aforementioned $C_{1-6}$ alkylamino group.

Examples of the "$C_{1-6}$ alkylthio group" include methylthio, ethylthio, n-propylthio, isospropylthio, sec-butylthio and n-pentylthio.

Examples of the "$C_{1-6}$ haloalkylthio group" include trifluoromethylthio.

Examples of the "$C_{1-6}$ alkylsulfonyl group" include methanesulfonyl, ethanesulfonyl, n-propylsulfonyl, isopropylsulfonyl, n-butylsulfonyl, isobutylsulfonyl, sec-butylsulfonyl, tert-butylsulfonyl, n-pentylsulfonyl, sec-pentylsulfonyl, isopentylsulfonyl, neopentylsulfonyl, n-hexylsulfonyl and isohexylsulfonyl.

Examples of the "$C_{1-6}$ haloalkylsulfonyl group" include chloromethylsulfonyl and trifluoromethylsulfonyl.

Examples of the "$C_{1-6}$ alkylsulfonylamino group" or the "$C_{1-6}$ haloalkylsulfonylamino group" include a substituent in which an amino group is attached to the "$C_{1-6}$ haloalkylsulfonyl group" or the "$C_{1-6}$ haloalkylsulfonyl group".

As the substituent $R_1$, (i) a hydrogen atom, (ii) a phenyl group or a phenylalkyl group, each of which is optionally substituted, (iii) an alkyl group of 1 to 16 carbon atoms or (iv) a cycloalkyl-alkyl group is preferable. As a phenylalkyl group, benzyl group or 2-phenylethyl group is more preferable. Examples of the substituent on the benzene ring of a phenyl group or a phenylalkyl group include a halogen atom, more preferably a fluorine atom and a chlorine atom; a hydroxy group; a $C_{1-6}$ alkyl group, more preferably methyl or t-butyl; a $C_{1-6}$ haloalkyl group, more preferably trifluoromethyl; a $C_{1-6}$ alkoxy group, more preferably methoxy; a $C_{1-6}$ haloalkoxy group, more preferably trifluoromethoxy. More preferable examples of the substituent $R_1$ include phenyl, benzyl, 4-chlorophenyl, 2,4-difluorophenyl, 2,3,4-trifluorophenyl, 4-t-butylphenyl, 4-methoxyphenyl, 2-methoxy-4-t-butylphenyl, 4-trifluoromethoxyphenyl, 4-hydroxybenzyl, 3,4-dichlorobenzyl, 2,3,4-trichlorobenzyl, 4-methylbenzyl, 4-trifluoromethylbenzyl, 4-methoxybenzyl, 3,4-dimethoxybenzyl, 2-(4-methoxyphenyl)-ethyl, ethyl, isopropyl, n-hexyl, n-heptyl, n-octyl, n-tetradecyl, and cyclohexylmethyl.

(a) When $R_1$ is hydrogen, then the substituent $R_1'$ represents (i) a phenyl group or a phenylalkyl group, each of which is optionally substituted, (ii) a naphthyl group or a naphthylalkyl group, each of which is optionally substituted, (iii) a heterocyclic group, a heterocyclic alkyl group or a heterocyclic aminoalkyl group, each of which is optionally substituted, (iv) an optionally substituted alkyl group of 1 to 16 carbon atoms, or (v) a cycloalkyl group or a cycloalkyl-alkyl group, each of which is optionally substituted, said group (i) to (v) being substituted at position 1 of the dihydrotriazine ring. These substituents are as described for the aforementioned substituent $R_1$.

(b) When $R_1$ is other than hydrogen, then the substituent $R_1'$ represents a hydrogen atom attached to the nitrogen atom at position 1 or 3 of the dihydrotriazine ring.

The substituents $R_2$ and $R_4$ each represents a hydrogen atom or an optionally substituted alkyl group of 1 to 16 carbon atoms. Herein, the alkyl group of 1 to 16 carbon atoms may be linear or branched, and examples include those exemplified for the aforementioned $R_1$. When $R_2$ is hydrogen, at least one of $R_1$ and $R_4$ is preferably an optionally substituted alkyl group of 6 to 16 carbon atoms, more preferably an alkyl group of 12 to 16 carbon atoms, most preferably an alkyl group of 13 to 15 carbon atoms. In the present invention, more preferably, at least one of $R_2$ and $R_4$ is an alkyl group of 6 to 16 carbon atoms, preferably 7 to 16 carbon atoms, and the other is hydrogen or an alkyl group of 1 to 6 carbon atoms. More preferably, at least one of $R_2$ and $R_4$ is a linear alkyl group of 7 to 13 carbon atoms, more preferably 8 to 12 carbon atoms, and the other is hydrogen or methyl.

The substituent $R_3$ represents a hydrogen atom or an optionally substituted alkyl group of 1 to 3 carbon atoms. Herein, an alkyl group of 1 to 3 carbon atoms maybe linear or branched, and examples include methyl, ethyl, propyl and isopropyl. In addition, the alkyl group of 1 to 3 carbon atoms may form a ring such as a cyclopropyl group.

Regarding $R_3$ and $R_4$, $R_3$ and $R_4$ may be taken together with the carbon atom to which they are attached to form a spirocycloalkane group or an alkylspirocycloalkane group. In this case, it is preferable that $R_2$ is an optionally substituted alkyl group of 6 to 16 carbon atoms, preferably 7 to 16 carbon atoms. Regarding the spirocycloalkane, the number of carbon atoms which constitute the ring is 3 to 16, preferably 3 to 12, more preferably 3 to 8, still more preferably 4 to 6. Examples of the "alkylspirocycloalkane" include those having one or more substituent(s), in which a replaceable number of alkyl groups of 1 to 6 carbon atoms are attached to chemically acceptable arbitrary position(s) of the aforementioned spirocycloalkane.

When the substituents $R_2$, $R_3$ and $R_4$ are an alkyl group, the aforementioned alkyl group may have a substituent. Examples of the substituent of such alkyl group include a halogen atom, a $C_{1-6}$ alkoxy group, a $C_{1-6}$ alkylthio group, a $C_{1-6}$ haloalkoxy group, a $C_{1-6}$ haloalkylthio group, a hydroxy group, an amino group, a $C_{1-6}$ alkylamino group, a di-$C_{1-6}$-alkylamino group, a $C_{1-7}$ alkanoylamino group, a formyl group, a $C_{1-6}$ alkoxycarbonyl group, $C_{1-6}$haloalkoxycarbonyl group, a carbamoyl group, a mercapto group and a cyano group. The substitution position of substituent(s) is not particularly limited as far as it is chemically acceptable, and the number of substituents may be within a replaceable number range, and is preferably 1 to 6.

In addition, when $R_3$ and $R_4$ are not the same, and $R_1$ and $R_2$ are not the same, there are two kinds of optical isomers of the carbon atom at position 6 of the dihydrotriazine ring, and any isomer is included in the scope of the aforementioned compound.

In the compound represented by the aforementioned general formula (1), a double bond represented by the dashed line is located at positions between 2 and 3, when $R_1$ is hydrogen and $R_1'$ is substituted at position 1 of the dihydrotriazine ring, or a double bond is located at positions between 1 and 2 or between 2 and 3, when the position 1 of the dihydrotriazine ring is unsubstituted. However, in the compounds represented by the general formula (1), there are several other tautomers, and a double bond can be moved depending on its environment. The present invention includes all of these tautomers.

Each group in the formula (1a) will be explained below.

The substituents $R_1$ and $R_1'$ in the formula (1a) are as explained for the aforementioned formula (1).

In the present invention, it is preferable that the substituent $R_1$ is (i) a hydrogen atom, (ii) a phenyl group or a phenylalkyl group, each of which is optionally substituted, (iii) an optionally substituted naphthyl group,(iv) a heterocyclic group, a heterocyclic alkyl group or a heterocyclic aminoalkyl group, each of which is optionally substituted, (v) an optionally substituted alkyl group of 1 to 16 carbon atoms, or (vi) a cycloalkyl group or a cycloalkyl-alkyl group, each of which is optionally substituted, and (a) When $R_1$ is hydrogen, then $R_1{}'$ is (i) a phenyl group or a phenylalkyl group, each of which is optionally substituted, (ii) a naphthyl group or a naphthylalkyl group, each of which is optionally substituted, (iii) a heterocyclic group, a heterocyclic alkyl group or a heterocyclic aminoalkyl group, each of which is optionally substituted, or (iv) an optionally substituted alkyl group of 1 to 16 carbon atoms (more preferably 7 to 16 carbon atoms), each of which is optionally substituted, said groups (i) to (iv) being substituted at position 1 of the dihydrotriazine ring.

$R_{21}$ represents an optionally substituted alkyl group of 7 to 16 carbon atoms. Examples of the "alkyl group of 7 to 16 carbon atoms" include a linear or branched alkyl group of 7 to 16 carbon atoms, and preferably such alkyl groups include, for example, n-heptyl, n-octyl, tert-octyl, n-nonyl, n-decyl, n-undecyl, n-dodecyl, n-tridecyl, n-tetradecyl, n-pentadecyl, and n-hexadecyl. The optionally substituted alkyl group of 7 to 16 carbon atoms may have the same substituents as those explained for the aforementioned formula (1).

The substituents $R_3$ and $R_4$ in the formula (1a) are as explained for the aforementioned formula (1) and, in the formula (1b), it is preferable that the substituent $R_3$ is an optionally substituted alkyl group of 1 to 3 carbon atoms, and $R_4$ is an optionally substituted alkyl group of 1 to 16 carbon atoms.

The dashed line in the formula (1a) is as explained for the aforementioned formula (1).

Each group in the formula (1b) will be explained below.

The substituent $R_{11}$ represents (i) a hydrogen atom, (ii) an optionally substituted phenyl group, (iii) a naphthyl group or a naphthylalkyl group, each of which is optionally substituted, (iv) a heterocyclic group or a heterocyclic alkyl group, each of which is optionally substituted, or (v) a cycloalkyl group or a cycloalkyl-alkyl group, each of which is optionally substituted. These groups may be the same as respective groups explained for the aforementioned $R_1$, respectively. In the present invention, it is preferable that the $R_{11}$ is an optionally substituted phenyl group.

(a) When $R_{11}$ is hydrogen, then the substituent $R_{11}{}'$ represents (i) a naphthyl group or a naphthylalkyl group, each of which is optionally substituted, (ii) a heterocyclic group or a heterocyclic alkyl group, each of which is optionally substituted, (iii) an optionally substituted alkyl group of 1 to 16 carbon atoms, or (iv) a cycloalkyl group or a cycloalkyl-alkyl group, each of which is optionally substituted, said groups (i) to (iv) being substituted at position 1 of the dihydrotriazine ring. These groups may be the same as those explained for the aforementioned $R_1{}'$.

(b) When $R_{11}$ is other than hydrogen, then the substituent $R_{11}{}'$ represents a hydrogen atom attached to the nitrogen atom at position 1 or 3 of the dihydrotriazine ring.

The substituents $R_3$ and $R_4$ in the formula (1b) are as explained for the aforementioned formula (1).

The dashed line in the formula (1b) is as explained for the aforementioned formula (1).

In the formula (1b), at least one of $R_{11}$ and $R_4$ is an optionally substituted alkyl group of 7 to 16 carbon atoms. The "optionally substituted alkyl group of 7 to 16 carbon atoms" is the same as the group explained for the aforementioned formula (1a).

Each group in the formula (1d) will be explained below.

The substituent $R_{12}$ in the formula (1d) represents a hydrogen atom, or a heterocyclic group, a heterocyclic alkyl group or a heterocyclic aminoalkyl group, the last three groups of which are optionally substituted.

(a) When $R_{12}$ is hydrogen, then the substituent $R_{12}{}'$ in the formula (1d) represents a heterocyclic group, a heterocyclic alkyl group or a heterocyclic aminoalkyl group, each of which is optionally substituted and is attached to position 1 of the dihydrotriazine ring, or (b) when $R_{12}$ is other than hydrogen, $R_{12}{}'$ represents a hydrogen atom attached to the nitrogen atom at position 1 or 3 of the dihydrotriazine ring. The "heterocyclic group, heterocyclic alkyl group or heterocyclic aminoalkyl group, each of which is optionally substituted" in the aforementioned substituents $R_{12}$ and $R_{12}{}'$ are as explained in the aforementioned formula (1).

The substituents $R_2$, $R_3$ and $R_4$ in the formula (1d) are as explained for the aforementioned formula (1). The dashed line in the formula (1d) is also as explained for the aforementioned formula (1).

The aforementioned compounds (1) may form a salt. Examples of such salt include salts with an organic acid such as formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid and methanesulfonic acid; salts with an inorganic acid such as hydrochloric acid, hydrobromic acid, sulfuric acid, phosphoric acid, nitric acid, carbonic acid, and boric acid. The aforementioned acid addition salt is prepared by adopting a normal salt forming method such as by (a) mixing the aforementioned compound (1) and an acid directly, (b) dissolving one of them in a solvent or a hydrous solvent, and mixing them, or (c) placing the compound (1) and an acid in a solvent or a hydrous solvent, and mixing them.

When the aforementioned compound (1) has an acidic group such as a carboxyl group and a sulfonic acid group, the compound (1) becomes a zwitterion salt, and such salt may be an alkali metal salt such as sodium salt and potassium salt, an alkaline earth metal salt such as calcium salt and magnesium salt, and a salt with an inorganic base such as aluminum salt and ammonium salt; a base addition salt such as salt with an organic base such as trimethylamine, triethylamine, pyridine, picoline, ethanolamine, diethanolamine, triethanolamine, dicyclohexylamine and N,N'-dibenzylethylenediamine. In addition, the salt of the aforementioned compound (1) may be a salt with a basic amino acid such as arginine, lysine and ornithine; a salt with an acidic amino acid such as aspartic acid.

The salt of the aforementioned compound (1) is preferably a pharmacologically acceptable salt, more preferably an acid addition salt, still more preferably acetate, hydrochloride, hydrobromide, methanesulfonate, malonate or oxalate.

When the aforementioned compound (1) is used as an external agent or a bactericide/disinfectant, the compound (1) may form a stable coordinated compound with a metal such as Ag, Mn and Zn.

Then, a process for preparing the compound (1) which is an active ingredient of the present invention will be explained. The compound (1) or a salt thereof can be prepared, for example, as follows:

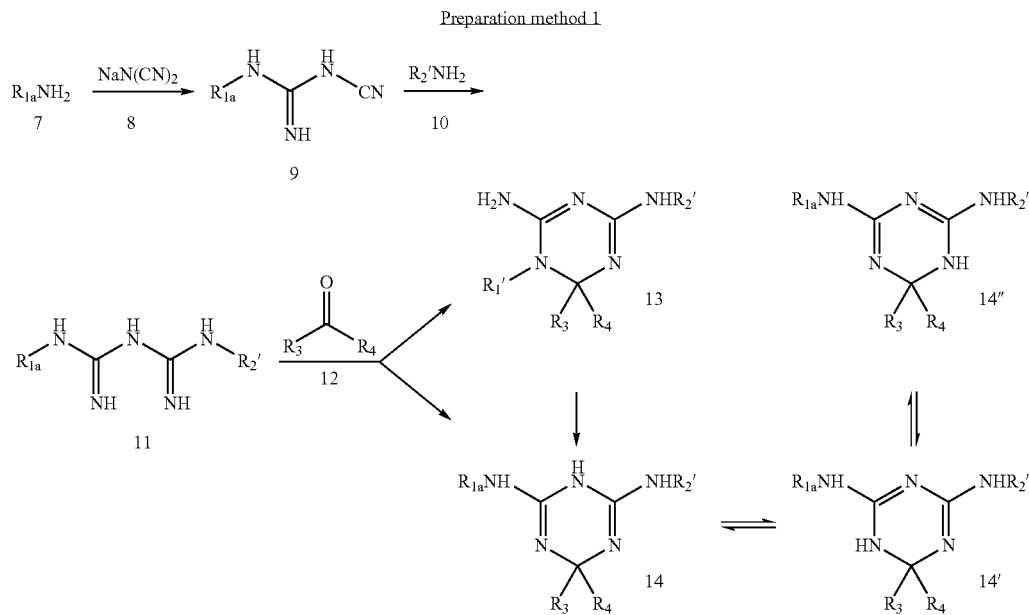

Preparation method 1

(wherein R$_2$' represents an optionally substituted alkyl group of 1 to 16 carbon atoms, R$_{1a}$ represents the aforementioned R$_1$ or R$_{11}$, and other all symbols are the same as defined above)

A process for preparing a compound represented by the general formula (1) wherein R$_2$ is an alkyl group (R$_2$') of 1 to 16 carbon atoms is shown in Preparation method 1. According to the present process, first, a compound (7) is converted into an acid addition salt (e.g. salt of hydrochloric acid, sulfuric acid, p-toluenesulfonic acid, benzenesulfonic acid, methanesulfonic acid, etc.), and is reacted with sodium dicyanamide (compound (8)) in a solvent (e.g. methanol, ethanol, propanol, isopropanol, butanol, benzene, toluene, xylene, ethyl acetate, tetrahydrofuran, acetonitrile, N,N-dimetylformamide) to prepare a cyanoguanidine derivative (compound (9)). The compound (9) may be prepared similarly by reacting a compound (7) with a compound (8) in the presence of an equivalent of an acid (e.g. hydrochloric acid, sulfuric acid, p-toluenesulfonic acid, benzenesulfonic acid, methanesulfonic acid, etc.) without converting the compound (7) into an acid addition salt. Amount of the compound (8) to be used is about 1 to 2 mol equivalents, preferably about 1 to 1.3 mol equivalents to 1 mole of a compound (7), and the reaction temperature is usually about 60° C. to 150° C., preferably about 80° C. to 120° C. The produced compound (9) is obtained in the form of a salt with an acid used, or may be recovered in the form of a free base by neutralization with sodium hydroxide or potassium hydroxide, if necessary.

Then, the compound (9) is reacted with an alkylamine (compound (10)) in the presence of an acid (e.g. hydrochloric acid, sulfuric acid, p-toluenesulfonic acid, benzenesulfonic acid, methanesulfonic acid etc.) in a solvent (e.g. methanol, ethanol, propanol, isopropanol, butanol, benzene, toluene, xylene, mesitylene, ethyl acetate, tetrahydrofuran, acetonitrile, N,N-dimethylformamide) to prepare a biguanide derivative (compound (11)). The acid and the compound (10) are used in an amount of about 1 to 2 mol equivalents, preferably about 1 to 1.3 mol equivalents to 1 mole of the compound (9), and the reaction temperature is usually about 60° C. to 170° C., preferably about 110° C. to 150° C. The produced compound (11) is obtained in the form of a salt with an acid used, or can be recovered in the form of a free base by neutralization using sodium hydroxide or potassium hydroxide, if necessary.

Then, the compound (11) is reacted with a compound (12) to prepare a compound (13) or (14), (14') or (14") which is an objective compound. The compound (11) may be used in the reaction in the form of an acid addition salt or a free base. As a compound (12), in addition to ketones and aldehydes, equivalents thereof such as acetals may be used. The present reaction is performed in a solvent which is the compound (12), or in a mixed solvent obtained by adding other solvent (e.g. methanol, ethanol, propanol, isopropanol, butanol, ethyl acetate, tetrahydrofuran, acetonitrile, N,N-dimethylformamide and a mixed solvent thereof) to the compound (12), or in a solvent in the presence of an acid (e.g. hydrochloric acid, sulfuric acid, p-toluenesulfonic acid, benzenesulfonic acid, methanesulfonic acid, etc.) or abase (e.g. piperidine, pyridine, triethylamine, sodium hydroxide, potassium hydroxide, etc.). In the present reaction, products are different depending on the kind of R$_{1a}$ and the reaction conditions. Usually, in the presence of an acid, a mixture of a compound (14) and a compound (13) is produced and, when R$_{1a}$ is a phenyl group, a compound (13) is preferentially produced. On the other hand, in the presence of a base, a compound (14) is preferentially produced in many cases regardless of the kind of R$_{1a}$. The amount of an acid and a base to be used is about 0.1 to 3 mol equivalents, preferably about 0.3 to 1.5 mol equivalents, relative to 1 mole of a compound (11). When a compound (12) is not used as a solvent, the amount of the compound (12) to be used is about 1 to 12 mol equivalents, preferably about 1 to 2 mol equivalents relative to 1 mole of a compound (11), and the reaction temperature is usually normal temperature to around 150° C., preferably about 60° C. to 80° C. In the presence of an acid, a compound (13) and a compound (14)

are obtained as a salt with an acid used, or is recovered in the form of a free base by neutralization using sodium hydroxide or potassium hydroxide, etc., if necessary. An acid salt or a free base of a compound (13) and a compound (14) can be separated and purified by silica gel column chromatography or recrystallization.

In addition, the resulting compound (13) or a mixture of compounds (13) and (14) can be heated in water or a hydrous solvent (e.g. methanol, ethanol, propanol, isopropanol, tetrahydrofuran, acetonitrile, etc.) to convert into a compound (14). The reaction temperature is usually about 50° C. to 100° C., preferably about 80° C. to 100° C. A compound (14') is a tautomer of a compound (14).

When a free base of the above-obtained compound (13), (14), (14') or (14") is extracted with an acetic acid ester (e.g. ethyl acetate), it can be converted into an acetate salt in accompany with hydrolysis of acetic acid ester. Alternatively, the compound may be led to an appropriate organic or inorganic acid addition salt using the aforementioned acid or acid salt (e.g. sodium chloride, sodium bromide, sodium acetate, potassium acetate, sodium nitrate, potassium nitrate, etc.) in water, a solvent (e.g. ethanol, methanol, acetonitrile, acetone, methyl ethyl ketone, etc.), or a hydrous solvent, and these acid addition salt may be purified by recrystallization or chromatography.

to 1 mole of the compound (7), and the reaction temperature is usually about 60° C. to 150° C., preferably about 80° C. to 100° C. The produced compound (16) is obtained in the form of a salt with an acid used, or may be recovered in the form of a free base by neutralization using sodium hydroxide or potassium hydroxide, etc., if necessary.

Then, the compound (16) is reacted with a compound (12) to prepare a compound (17), (18), (18') or (18") which is an objective compound. The reaction of the compound (16) with the compound (12) can be performed in the entirely same manner as that in the aforementioned reaction of the compound (11) with the compound (12), and the compound (17) can undergo migration into the compound (18) in entirely the same manner as that in the case of the compound (13). The compounds (18') and (18") are a tautomer of the compound (18).

In the compound (1) as mentioned above, when the position 6 of the dihydrotriazine ring bears an asymmetric carbon atom, two kinds of optical isomers can be separated into respective isomers by a normal optical resolution. That is, there are appropriately employed a method of isolating and purifying an objective salt by forming diastereomer salt using optically active carboxylic acid (e.g. D- and L-lactic acid, D- and L-mandelic acid, D- and L-malic acid, D- and L-tartaric acid, dibenzoyl-D- and L-tartaric acid, ditoloyl-L- and D-tar- Preparation method 2

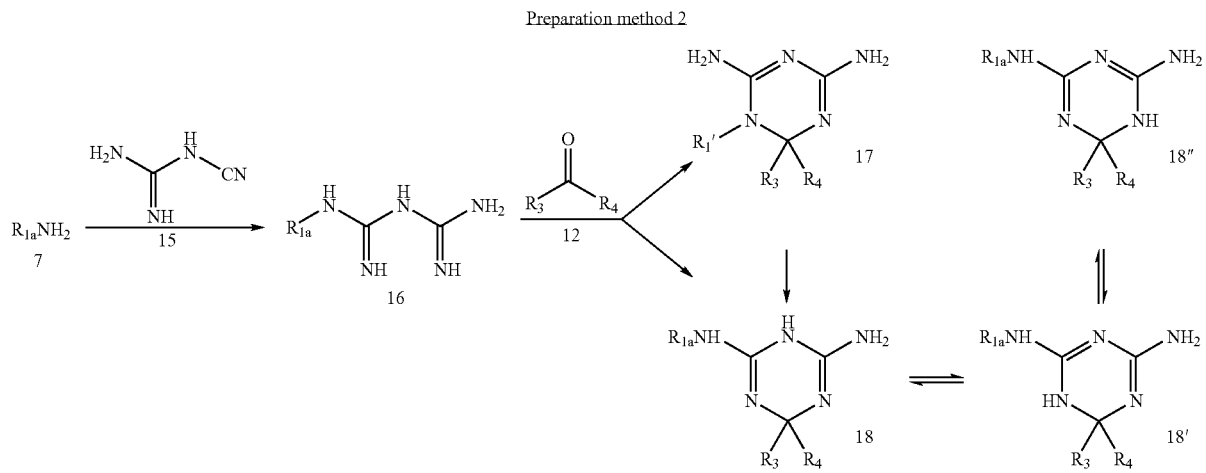

(wherein all the symbols are each the same as defined above)

A process for preparing a compound represented by the general formula (1) wherein R₂ is a hydrogen atom is shown in Preparation method 2. According to the present process, first, a compound (7) is converted into an acid addition salt (e.g. a salt of hydrochloric acid, sulfuric acid, p-toluenesulfonic acid, benzenesulfonic acid, methanesulfonic acid, etc.), and is reacted with dicyanodiamide (compound (15)) in a solvent (e.g. methanol, ethanol, propanol, isopropanol, butanol, benzene, toluene, xylene, ethyl acetate, tetrahydrofuran, acetonitrile, N,N-dimethylformamide, etc.) to prepare a biguanide derivative (compound (16)). The compound (16) may be similarly prepared by reacting a compound (7) with a compound (15) in the presence of an equivalent of an acid (e.g. hydrochloric acid, sulfuric acid, p-toluenesulfonic acid, benzenesulfonic acid, methanesulfonic acid, etc.) without converting the compound (7) into an acid addition salt. The amount of the compound (15) to be used is about 1 to 2 mol equivalents, preferably about 1 to 1.3 mol equivalents relative taric acid, acidic amino acid such as L- and D-aspartic acid, D- and L-glutamic acid, and N-protecting group-substituted derivative of D- and L-amino acid) or sulfonic acid (e.g. camphorsulfonic acid etc.), followed by neutralization; a preferential crystallization; or a high performance liquid chromatography using an optically active column. Among the compound (1) which is an active ingredient of an antibacterial agent of the present invention, the compounds (1a), (1b), (1c), and (1d) are novel compounds.

Examples of a preferable embodiment of the compound (1) include a compound in which at least one of R₂ and R₄ in the general formula (1) is an optionally substituted alkyl group of 7 to 16 carbon atoms.

Examples of a preferable embodiment of the compound (1a) include a compound in which R₁ in the general formula (1a) is (i) a hydrogen atom, (ii) a phenyl group or a phenylalkyl group, each of which is optionally substituted, (iii) an optionally substituted naphthyl group, (iv) a heterocyclic group, a heterocyclic alkyl group or a heterocyclic aminoalkyl group, each of which is optionally substituted, (v) an optionally substituted alkyl group of 1 to 16 carbon atoms, or (vi) a cyclo alkyl group or a cycloalkyl-alkyl group, each of which is optionally substituted, and (a) when $R_1$ is hydrogen, then $R_1'$ is (i) a phenyl group or a phenylalkyl group, each of which is optionally substituted, (ii) a naphthyl group or naphthylalkyl group, each of which is optionally substituted, (iii) a heterocyclic group, a heterocyclic alkyl group or a heterocyclic aminoalkyl group, each of which is optionally substituted, or (iv) an optionally substituted alkyl group of 1 to 16 carbon atoms, said groups (i) to (iv) being attached to position 1 of the dihydrotriazine ring. Examples of a more preferable embodiment include a compound in which $R_1$ in the aforementioned general formula (1a) is a phenyl group or a phenylalkyl group, each of which is optionally substituted, $R_3$ is an optionally substituted alkyl group of 1 to 3 carbon atoms, and $R_4$ is an optionally substituted alkyl group of 1 to 16 carbon atoms.

In addition, examples of a preferable embodiment of the compound (1b) include a compound in which $R_{11}$ in the aforementioned general formula (1b) is an optionally substituted phenyl group.

The compound (1) is not only useful in preventing or treating bacterial infectious diseases of humans and other mammals (dog, cat, sheep, pig, horse, cow, etc.), birds (chicken, dabbling duck, duck, quail, turkey, etc.) and fish (sea bream, young yellowtail, eel, etc.) by oral administration or parenteral administration, but also extremely useful as an external bactericides and disinfectants. When used as an external bactericidal or disinfectant agent, the compound can be not only used for the purpose of sterilizing or disinfecting a wound site, a burn site or a bedsore site, or for the purpose of sterilizing or disinfecting an operation site before and after operation, but also can be used for sterilizing or disinfecting a hand or an arm of a medical employee, or sterilizing or disinfecting medical equipments or medical environment (construction and facilities thereof).

The compound (1) may also be used as an antiseptic or a preservative for cosmetics (cream, emulsion, lotion, etc.).

As a medicine of the present invention, the compound (1) or a pharmacologically acceptable salt thereof may be used as it is, but generally a form of a medical preparation containing the aforementioned active ingredients and 1 or 2 or more pharmaceutical additives is preferable. Examples of such pharmaceutical preparation include tablets, pills, capsules, powders, granules, suppositories, injections, paste agents, ointments, creams, gels, gel-like creams, lotions, emulsions, suspensions, poultices, plasters, liniments, aerosols, syrups, oral cavity agents, eye drops and nasal drops. The aforementioned tablets maybe coated tablets such as sugar-coated tablets, gelatin-coated tablets, enteric coated tablets and film-coated tablets, or may be double tablets or multilayer tablets. Inter alia, the medicine of the present invention preferably has a dosage form of an external agent, more preferably a dosage form of external liquids.

The aforementioned pharmaceutical preparation can be prepared by the method which is known per se or conventional in the field of pharmacy.

In the medicine of the present invention, for preparing solid preparations such as tablets, pills, capsules, powders and granules, for example, excipients, binders, disintegrating agents, surfactants or lubricants may be used as a preparation additive. Examples of such excipients include sugars such as lactose, white sugar and glucose; starches such as starch; and crystalline cellulose; etc. Examples of such binders include sugars or sugar alcohols such as glucose and maltitol; polysaccharides such as starch; natural polymers such as gelatin; cellulose derivatives such as methylcellulose and carboxymethylcellulose; and synthetic polymer compounds such as polyvinylpyrrolidone. Examples of such disintegrating agents include starch, sodium alginate, corn starch, hydroxypropylstarch, polyvinylpyrrolidone and sodium croscarmellose. Examples of such lubricants include stearic acid salt, talc, boric acid powder and polyethylene glycol. Examples of such surfactants include fatty acid ester.

When the medicine of the present invention has a dosage form of suppositories, the medicine of the present invention can be prepared by incorporating the compound (1) or a pharmacologically acceptable salt thereof and, optionally, for example, local anesthetics, anti-histamine agents, local astringents, sulfa drugs, antibiotics, wound therapeutics, surfactants, vitamins, crude drug extracts, bile acids, antiseptics, excipients, absorption promoters or amino acids into a lipophilic base, a hydrophilic base or an emulsion base.

When the medicine of the present invention has a dosage form of injections, the medicine of the present invention can be prepared by incorporating the compound (1) or a pharmacologically acceptable salt thereof and, optionally, preparation additives such as solubilizers, buffers and soothing agents into a water-soluble solvent or a water-insoluble solvent. It is preferable that injections of the present invention are sterilized, and isotonic to blood, and injections may contain sodium chloride, glucose or glycerin, etc. in order to be isotonic to blood. Further, coloring agents, preservatives, perfumes, flavors or sweeteners may be optionally contained in pharmaceutical preparations.

When the medicine of the present invention has a dosage form of ointments, the medicine of the present invention can be prepared by incorporating the compound (1) or a pharmacologically acceptable salt thereof and, optionally, preparation additives such as emulsifying agents such as anionic or nonionic surfactants, and preservatives such as paraoxybenzoic acid esters into bases such as lipophilic bases such as vaseline, liquid paraffin, silicone and vegetable oil; emulsion bases such as hydrophilic vaseline and purified lanoline; or water-soluble bases such as macrogol.

When the medicine of the present invention has a dosage form of gels, the medicine of the present invention can be prepared by incorporating the compound (1) or a pharmacologically acceptable salt thereof and, optionally, preparation additives such as lower alcohols, neutralizing agents, surfactants and absorption promoters into a base obtained by adding a gelling agent (e.g. carboxyvinyl polymer, hydroxyethylcellulose, hydroxypropylcellulose, methylcellulose, ethylcellulose, carboxymethylcellulose and alginic acid propylene glycol ester, etc.) to water.

When the medicine of the present invention has a dosage form of creams, the medicine of the present invention can be prepared by incorporating the compound (1) or a pharmacologically acceptable salt thereof and, optionally, preparation additives such as emulsifying agents, antiseptics, absorption promoters and rash preventing agents into a base containing fatty acid esters (e.g. myristic acid ester, palmitic acid ester, diethyl sebacate, hexyl laurate, cetyl isooctate, etc.), lower alcohols (e.g. ethanol, isopropanol, etc.), hydrocarbons (e.g. liquid paraffin, squalane, etc.), polyhydric alcohols (e.g. propylene glycol, 1,3-butylene glycol, etc.) or higher alcohols (e.g. 2-hexyldecanol, cetanol, 2-octyldodecanol, etc.).

In addition, in order to obtain gel-like creams having a nature between creams and gels, a gelling agent and a neutralizing agent may be added to the aforementioned creams.

When the medicine of the present inventions has a dosage form of external liquids, the medicine of the present invention can be prepared by incorporating the compound (1) or a pharmacologically acceptable salt thereof and, optionally, preparation additives such as buffers, stabilizers, antiseptics, pH adjusting agents, solvents, solubilizers, flavors, gels, corrigents and refreshing agents into a solvent. Examples of such solvent include, for example, glycerin, propylene glycol, ethanol, isopropanol, butylene glycol, water, sorbitol, mannitol, xylitol, glucose, ε-aminocaproic acid, glycine, glutamic acid salt, sodium hyaluronate, polyethylene glycols, carboxyvinyl polymers, higher alcohols such as cetanol and stearyl alcohol, fatty acid esters such as medium-chain fatty acid esters and isopropyl mysristate, higher fatty acid such as stearic acid, squalane, liquid paraffin, white vaseline and purified lanolin.

Herein, examples of external liquids include liquid preparations which are subjected to external use such as washing, injection, wet compression, inhalation, spraying, enema administration, coating, drug bathing, clean wiping, disinfection, eye dropping, eye washing, ear dropping and nasal dropping.

Aerosols can be prepared by using external liquids of the present invention together with a normal propellant. Examples of the propellant include dimethyl ether, liquefied petroleum gas, $N_2$ gas, nitrous oxide gas, $CO_2$ gas, and alternative chlorofluorocarbon gas. The compressed air may be used without using a propellant. Alternatively, a mixture of them may be used.

Administration route, dose and administration frequency of the medicine of the present invention are not particularly limited, and can be appropriately selected depending on various conditions such as the kind of diseases to be treated, age and body weight of patients, symptom and severity of diseases. More specifically, a therapeutic dose as an antibacterial agent is about 0.001 to 100 mg/kg per adult a day in the case of oral administration. When the medicine of the present invention is an external agent for the purpose of sterilization or disinfection, it is preferable that a dose is adjusted so that an active ingredient is 0.01 to 10% by weight.

WORKING EXAMPLES

The present invention will be further explained in more detail by way of the following Working Examples. The present invention is not limited to these Examples.

Working Example 1

3,6-Dihydro-6,6-dimethyl-4-decylamino-2-(4'-methoxybenzylamino)-1,3,5-triazine hydrochloride 80 ml of methanol, 120 ml of acetone and 0.1 ml of concentrated hydrochloric acid were added to 2.0 g (4.6 mmol) of $N^1$-(4-methoxybenzyl)-$N^5$-decyl-bigunide dihydrochloride, and the mixture was refluxed for 21 hours. After removal of the solvent by evaporation under reduced pressure, the residue was dissolved in a 80% aqueous acetonitrile solution, and the solvent was removed by evaporation under reduced pressure. The residue was purified by subjecting to silica gel column chromatography (elution with a mixture of chloroform/ethanol/acetic acid (9:0.5:9.5) to obtain 1.7 g of a colorless resinous solid.

$^1$H-NMR(CDCl$_3$)δ: 0.87(3H,t,J=7 Hz,CH$_3$), 1.1-1.6(16H, m), 1.40(6H,s,(CH$_3$)$_2$C), 3.28(2H,br dt-like,NHCH$_2$), 3.77 (3H,s,CH$_3$O), 4.45(2H,d,J=5 Hz,ArCH$_2$NH), 6.81(2H,d,J=8 Hz,ArH), 7.11(1H,br t-like,NHCH$_2$), 7.19(2H,d,J=8 Hz,ArH), 7.45(1H,br t-like,ArCH$_2$NH), 8.47, 8.60(each 1H,br s,NH,NH$^+$).

By $^1$H—$^1$H COSY, coupling was recognized between NHCH$_2$(δ: 3.28), NHCH$_2$(δ: 7.11), ArCH$_2$NH(δ: 4.45) and ArCH$_2$NH(δ: 7.45) signals. In addition, no coupling was recognized between triazine ring NH and NH$^+$(δ: 8.47,8.60) signals and other proton.

Working Example 2

3,6-Dihydro-6,6-dimethyl-4-decylamino-2-benzylamino-1,3,5-triazine methanesulfonate To a solution of 11.0 g (27.2 mmol) of $N^1$-benzyl-$N^5$-decyl-biguanide dihydrochloride in 150 ml of methanol was added 16 ml of 5N aqueous sodium hydroxide, and the mixture was stirred at 60° C. for 30 minutes. After removal of the solvent by evaporation under reduced pressure, the residue was extracted with chloroform. The extract was washed with water, the solvent was removed by evaporation under reduced pressure, and 100 ml of acetone and 16 g (19.0 mmol) of piperidine were added to the residue. The mixture was refluxed for 17 hours, and then concentrated under reduced pressure to remove the solvent. The residue was washed with water, and sufficiently dried under reduced pressure to obtain 10.0 g of a colorless resinous solid. Then, 2.5 g (6.7 mmol) of the above solid was dissolved in 50 ml of acetone, and 16 g (16.7 mmol) of methanesulfonic acid was added thereto. The solvent was evaporated off under reduced pressure to give a residue, which was dissolved in 70% aqueous acetonitrile. The solvent was removed by evaporation under reduced pressure, and the residue was purified by silica gel column chromatography (elution with a mixture of chloroform and methanol (9:1.5)), and ether was added for crystallization, yielding 2.6 g of colorless crystals having a melting point of not higher than 50° C.

$^1$H-NMR(CDCl$_3$)δ: 0.88(3H,t J=7 Hz,CH$_3$), 1.1-1.6(16H, m), 1.40(6H,s,(CH$_3$)$_2$C), 2.76(3H,s,CH$_3$SO$_3$$^-$), 3.22(2H,br dt-like,NHCH$_2$), 4.50(2H,d,J=6 Hz,ArCH$_2$NH), 7.16(1H,br t-like,NH), 7.2-7.3(5H,m,ArH), 7.60(1H,t,J=6 Hz,NH), 7.96, 8.09(each 1H,br s,NH,NH$^+$).

Working Example 3

3,6-Dihydro-6,6-dimethyl-2-(3',4'-dimethoxybenzylamino)-4-decylamino-1,3,5-triazine hydrochloride 75 ml of methanol, 120 ml of acetone and 0.2 ml of concentrated hydrochloric acid were added to 3.5 g (7.5 mmol) of $N^1$-(3,4-dimethoxybenzyl)-$N^5$-dodecyl-biguanide dihydrochloride, and the mixture was refluxed for 24 hours. The solvent was distilled off under reduced pressure, and the residue was purified by silica gel column chromatography (elution with a mixture of chloroform and methanol (9:1.2)), and dissolved in 70% aqueous acetonitrile. The solution was concentrated under reduced pressure to remove the solvent, and the residue was sufficiently dried under reduced pressure to obtain 2.2 g of a colorless resinous solid.

$^1$H-NMR(CDCl$_3$)δ: 0.87(3H,t,J=7 Hz,CH$_3$), 1.1-1.6(16H, m), 1.42(6H,s,(CH$_3$)$_2$C), 3.30(2H,br dt-like,NHCH$_2$), 3.85, 3.86(each 3H,s,CH$_3$O), 4.46(2H,d,J=6 Hz,ArCH$_2$), 6.7-6.9 (3H,m,ArH), 7.12,7.46(each 1H,br t-like,NH), 8.51,8.63(each 1H,br s,NH,NH$^+$).

Working Example 4

3,6-Dihydro-6,6-dimethyl-4-decylamino-2-(4'-methoxyphenethylamino)-1,3,5-triazine hydrochloride 125 ml of methanol, 80 ml of acetone and 0.2 ml of concentrated hydrochloric acid were added to 2.0 g (4.5 mmol) of $N^1$-(4-methoxyphenethyl)-$N^5$-decyl-biguanide dihydrochloride. The mixture was refluxed for 24 hours, and the solvent was distilled off under reduced pressure. The residue was purified by silica gel column chromatography (elution with a mixture of chloroform/methanol/acetic acid (8:0.6:0.6)), and dissolved in 70% aqueous acetonitrile. The solvent was distilled off under reduced pressure, followed by sufficient drying under reduced pressure to obtain 2.1 g of a colorless resinous solid.

$^1$H-NMR(CDCl$_3$)δ: 0.87(3H,t,J=7 Hz,CH$_3$), 1.12-1.6 (16H,m), 1.43(6H,s,(CH$_3$)$_2$C), 2.80(2H,t,J=7 Hz,ArCH$_2$CH$_2$NH), 3.33(2H,br dt-like,NHCH$_2$), 3.51(2H,br dt-like,ArCH$_2$CH$_2$NH), 3.77(3H,s,CH$_3$O), 6.82(2H,d,J=9 Hz,ArH), 7.11(2H,d,J=9 Hz,ArH), 7.08-7.16(1H,over lap,NHCH$_2$), 7.21(1H,br t-like,ArCH$_2$CH$_2$NH), 8.49,8.51(each 1H,br s,NH,NH$^+$).

By $^1$H—$^1$H COSY, coupling was recognized between NHCH$_2$(δ: 3.33) and NHCH$_2$(δ: 7.08-7.16), ArCH$_2$CH$_2$NH(δ: 2.80) and ArCH$_2$CH$_2$NH(δ: 3.51), ArCH$_2$CH$_2$NH (δ: 3.51) and ArCH$_2$CH$_2$NH(δ: 7.21) signals. In addition, no coupling was recognized between triazine ring NH and NH$^+$ signals (δ: 8.49, 8.51) and other proton.

Working Example 5

3,6-Dihydro-6,6-dimethyl-4-nonylamino-2-(4'-methoxyphenethylamino)-1,3,5-triazine hydrochloride 100 ml of methanol, 40 ml of acetone and 0.2 ml of concentrated hydrochloric acid were added to 2.0 g (4.6 mmol) of $N^1$-(4-methoxyphenethyl)-$N^5$-nonyl-biguanide dihydrochloride, and the mixture was refluxed for 20 hours. The solvent was distilled off under reduced pressure to give a residue, which was dissolved in hydrous ethanol. The solvent was distilled off under reduced pressure, and the residue was purified by silica gel column chromatography (elution with a mixture of chloroform/methanol/acetic acid (8:0.7:0.7)) to obtain 1.2 g of a colorless resinous solid.

$^1$H-NMR(CD$_3$OD) δ: 0.90(3H,t,J=7 Hz,CH$_3$), 1.2-1.5 (18H,m,(CH$_2$)$_6$, (CH$_3$)$_2$C), 1.66(2H,m,NHCH$_2$CH$_2$), 2.91 (2H,t,J=7 Hz,ArCH$_2$CH$_2$), 3.29(2H,t,J=6 Hz,NHCH$_2$CH$_2$), 3.56(2H,t,J=7 Hz,ArCH$_2$CH$_2$), 3.77(3H,s,CH$_3$O), 6.88(2H,d,J=9 Hz,ArH), 7.22(2H,d,J=9 Hz,ArH).

Working Example 6

4-Undecylamino-3,6-dihydro-6,6-dimethyl-2-(4'-methoxyphenethylamino)-1,3,5-triazine hydrochloride 100 ml of methanol, 40 ml of acetone and 0.2 ml of concentrated hydrochloric acid were added to 2.0 g (4.3 mmol) of $N^1$-(4-methoxyphenethyl)-$N^5$-undecyl-biguanide dihydrochloride, and the mixture was refluxed for 16 hours. The solvent was distilled off under reduced pressure, and the residue was purified by silica gel column chromatography (elution with a mixture of chloroform/methanol/acetic acid (8:0.5:0.5)), and dissolved in hydrous ethanol. The solvent was distilled off under reduced pressure, followed by sufficient drying under reduced pressure to obtain 16 g of a colorless resinous solid.

$^1$H-NMR(DMSO-d$_6$)δ: 0.85(3H,m,CH$_3$), 1.0-1.6(18H,m), 1.35(6H,s,(CH$_3$)$_2$C), 2.74(2H,m,ArCH$_2$CH$_2$), 3.26(2H,m,NHCH$_2$), 3.42(2H,m,ArCH$_2$CH$_2$), 3.72(3H,s,CH$_3$O), 6.86(2H,m,ArH), 7.14(2H,m,ArH), 7.1-8.4(3H,m,NH×3), 8.49(1H,br s,NH$^+$).

Working Example 7

3,6-Dihydro-6,6-dimethyl-4-decylamino-2-(4'-hydroxybenzylamino)-1,3,5-triazine hydrochloride 25 ml of methanol, 40 ml of acetone and 0.1 ml of concentrated hydrochloric acid were added to 1.9 g (4.5 mmol) of $N^1$-(4-hydroxybenzyl)-$N^5$-decyl-biguanide dihydrochloride, and the mixture was refluxed for 30 hours. The solvent was distilled off under reduced pressure, and the residue was recrystallized with 80% aqueous acetonitrile to obtain 0.4 g of colorless crystals having a melting point of 109 to 111° C.

$^1$H-NMR(CDCl$_3$)δ: 0.87(3H,t,J=7 Hz,CH$_3$), 1.2-1.6(16H,m), 1.46(6H,s,(CH$_3$)$_2$C), 3.32(2H,br dt-like,NHCH$_2$), 4.41 (2H,d,J=6 Hz,ArCH$_2$), 6.81(2H,d,J=9 Hz,ArH), 7.11(2H,d,J=9 Hz,ArH), 7.24(2H,m,NH×2), 8.13,8.44,8.83(each 1H,brs,NH,OH,NH$^+$)

Working Example 8

4-Octylamino-3,6-dihydro-6,6-dimethyl-2-(4'-hydroxybenzylamino)-1,3,5-triazine hydrochloride 25 ml of methanol, 40 ml of acetone and 0.1 ml of concentrated hydrochloric acid were added to 16 g (4.6 mmol) of $N^1$-(4-hydroxybenzyl)-$N^5$-octyl-biguanide dihydrochloride, and the mixture was stirred at 40° C. for 63 hours, and refluxed for 8 hours. The solvent was distilled off under reduced pressure, to give a residue, which was dissolved in 80% aqueous acetonitrile. The solvent was distilled off under reduced pressure, and the residue was purified by silica gel column chromatography (elution with a mixture of chloroform and methanol (8:2)) to obtain 16 g of a colorless resinous solid.

$^1$H-NMR(CDCl$_3$)δ: 0.87(3H,t,J=7 Hz,CH$_3$), 1.0-1.6(12H,m), 1.40(6H,s,(CH$_3$)$_2$C), 3.31(2H,m,NHCH$_2$), 4.42(2H,m,ArCH$_2$), 6.82(2H,d,J=7 Hz,ArH), 7.09(2H,d,J=7 Hz,ArH), 7.0-7.2(1H,over lap), 7.26,8.19,8.25(each 1H,m).

Working Example 9

4-Undecylamino-3,6-dihydro-6,6-dimethyl-2-(4'-hydroxybenzylamino)-1,3,5-triazine hydrochloride 25 ml of methanol, 40 ml of acetone and 0.1 ml of concentrated hydrochloric acid were added to 2.0 g (4.5 mmol) of $N^1$-(4-hydroxybenzyl)-$N^5$-undecyl-biguanide dihydrochloride, and the mixture was refluxed for 24 hours. The solvent was distilled off under reduced pressure, and the residue was purified by silica gel column chromatography (elution with a mixture of chloroform and methanol (8:1.5)), and then recrystallized with 80% aqueous acetonitrile to obtain 0.73 g of colorless crystals having a melting point of 110 to 112° C.

$^1$H-NMR(CDCl$_3$)δ: 0.88(3H,t,J=7 Hz,CH$_3$), 1.1-1.6(20H,m), 1.46(6H,s,(CH$_3$)$_2$C), 3.32(2H,br dt-like,NHCH$_2$), 4.41

(2H,d,J=5 Hz,ArCH$_2$), 6.80(2H,d,J=9 Hz,ArH), 7.11(2H,d, J=9 Hz,ArH), 7.25(2H,m,NH×2), 8.13,8.44,8.86(each 1H,br s,NH,OH,NH$^+$).

Working Example 10

3,6-Dihydro-4-decylamino-2-(4'-methoxyphenethylamino)-1,3,5-triazine hydrochloride 200 ml of n-butanol, 6 ml (67.8 mmol) of methylal and 0.7 ml of concentrated hydrochloric acid were added to 2.5 g (5.6 mmol) of N$^1$-(4-methoxyphenethyl)-N$^5$-decyl-biguanide dihydrochloride, and the mixture was refluxed for 68 hours. The solvent was distilled of f under reduced pressure, and dissolved in 80% aqueous acetonitrile. The solvent was distilled off under reduced pressure to give a residue, which was purified by silica gel column chromatography (elution with a mixture of chloroform/methanol/acetic acid (8:0.7:0.7)) to obtain 0.7 g of a colorless resinous solid.

$^1$H-NMR(CDCl$_3$) δ: 0.87(3H,t,J=7 Hz, CH$_3$), 1.1-1.9 (16H,m), 2.80(2H,t,J=7 Hz,ArCH$_2$CH$_2$), 3.34(2H,br dt-like, NHCH$_2$), 3.52(2H,br dt-like,ArCH$_2$CH$_2$), 3.78(3H,s,CH$_3$O), 4.47(2H,s,CH$_2$), 6.83(2H,d,J=8 Hz,ArH), 7.12(2H,d,J=8 Hz,ArH), 7.3-7.5(2H,m,NH×2), 8.24(2H,m,NH,NH$^+$).

Working Example 11

4-Undecylamino-3,4-dihydro-6-methyl-2-(4'-methoxybenzylamino)-1,3,5-triazine hydrochloride Under ice-cooling, 100 ml of ethanol, 5 ml (89.2 mmol) of acetaldehyde and 0.4 ml of concentrated hydrochloric acid were added to 4.0 g (8.9 mmol) of N$^1$-(4-methoxybenzyl)-N$^5$-undecyl-biguanide dihydrochloride, and the mixture was refluxed for 24 hours. The solvent was distilled off under reduced pressure, and the residue was purified by silica gel column chromatography (elution with a mixture of chloroform and methanol (9:1.5)), and dissolved in 70% aqueous acetonitrile. The solvent was distilled off under reduced pressure, followed by sufficient drying under reduced pressure to obtain 1.4 g of a colorless resinous solid.

$^1$H-NMR(CDCl$_3$)δ: 0.88(3H,t,J=7 Hz,CH$_3$), 1.2-1.4(16H, m), 1.33(3H,d,J=6 Hz,HCCH$_3$), 1.50(2H,m,NHCH$_2$CH$_2$), 3.29(2H,br dt-like,NHCH$_2$CH$_2$), 3.77(3H,s,CH$_3$O), 4.45 (2H,d,J=6 Hz,ArCH$_2$NH), 4.72(1H,m,HCCH$_3$), 6.82(2H,d, J=9 Hz,ArH), 7.19(2H,d,J=9 Hz,ArH), 7.27(1H,br t-like,N H), 7.58(1H,t,J=6 Hz,NH), 8.33,8.45(each 1H,br s,NH, NH$^+$).

Working Example 12

4-Octylamino-2-(3',4'-dichlorobenzylamino)-3,6-dihydro-6,6-dimethyl-1,3,5-triazine hydrochloride
(1)

2-Amino-4-octylamino-1-(3',4'-dichlorobenzyl)-1,6-dihydro-6,6-dimethyl-1,3,5-triazine hydrochloride
(2)

25 ml of methanol, 40 ml of acetone and 0.1 ml of concentrated hydrochloric acid were added to 1.8 g (4.4 mmol) of N$^1$-(3',4'-dichlorobenzyl)-N$^5$-octyl-biguanide hydrochloride, and the mixture was refluxed for 24 hours. The solvent was distilled of f under reduced pressure, and the residue was dissolved in 80% aqueous acetonitrile. The solvent was distilled off under reduced pressure, and the residue was purified by silica gel column chromatography to obtain 0.5 g of a colorless resinous solid (1) from the first main elution fraction with a mixture of chloroform and methanol (95:5), and 0.7 g of a colorless resinous solid (2) from the second main elution fraction.

(1) $^1$H-NMR (CDCl$_3$) δ: 0.87(3H,t,J=7 Hz,CH$_3$), 1.2-1.6 (12H,m), 1.45(6H,s,(CH$_3$)$_2$C), 3.24(2H,br dt-like,NHCH$_2$), 4.46(2H,d,J=6 Hz,ArCH$_2$NH), 7.11(1H,d,J=8 Hz,ArH), 7.15 (1H,br t-like,NHCH$_2$), 7.35(1H,d,J=8 Hz,ArH), 7.36(1H,s, ArH), 7.71(1H,br t-like,ArCH$_2$NH), 8.54,8.58(each 1H,br s,NH,NH$^+$).

By $^1$H—$^1$H COSY, coupling was recognized between NHCH$_2$(δ: 3.24) and NHCH$_2$(δ: 7.15), ArCH$_2$NH(δ: 4.46) and ArCH$_2$NH(δ: 7.71) signals. In addition, no coupling was recognized between triazine ring NH and NH$^+$ signals (δ: 8.54, 8.58) and other proton.

(2) $^1$H-NMR (CDCl$_3$) δ: 0.88(3H,t,J=7 Hz, CH$_3$), 1.1-1.6 (12H,m), 1.47(6H,s,(CH$_3$)$_2$C), 3.21(2H,m,NHCH$_2$), 4.79 (2H,m,ArCH$_2$), 5.9-6.6(2H,br,NH$_2$), 7.05-7.45(3H,m,ArH), 7.30-7.45(1H,over lap,NHCH$_2$), 9.03(1H,m,NH$^+$).

By $^1$H—$^1$H COSY, coupling was recognized between NHCH$_2$(δ: 3.21) and NHCH$_2$ (δ: 7.30-7.45) signals. No coupling was recognized between NH$_2$(δ: 5.9-6.6) and NH$^+$(δ: 9.03) signals and other proton.

Working Example 13

2-Amino-1,6-dihydro-6,6-dimthyl-4-nonylamino-1-(2',3',4'-trifluorophenyl)-1,3,5-triazine hydrochloride 50 ml of methanol, 80 ml of acetone and 0.1 ml of concentrated hydrochloric acid were added to 1.3 g (3.0 mmol) of N$^1$- (2,3,4-trifluoroanilino)-N$^5$-nonyl-biguanide dihydrochloride, and the mixture was refluxed for 16 hours. The solvent was distilled off under reduced pressure, and the residue was purified by silica gel column chromatography (elution with a mixture of chloroform/methanol/acetic acid (9:0.5:0.5)), and dissolved in 80% aqueous ethanol. The solvent was distilled off under reduced pressure, followed by sufficient drying under reduced pressure to obtain 1.2 g of a pale yellow resinous solid.

$^1$H-NMR(CDCl$_3$)δ: 0.88(3H,t,J=7 Hz,CH$_3$), 1.1-1.6(14H, m), 1.44(6H,s,(CH$_3$)$_2$C), 3.32(2H,br dt-like,NHCH$_2$), 7.12 (1H,m,ArH), 8.46(1H,m,ArH).

Working Example 14

2-Amino-1,6-dihydro-6,6-dimethyl-4-decylamino-1-(4'-methoxyphenyl)-1,3,5-triazine hydrochloride 50 ml of methanol, 40 ml of acetone and 0.2 ml of concentrated hydrochloric acid were added to 1.5 g (3.6 mmol) of N$^1$-(4-methoxyphenyl)-N$^5$-decyl-biguanide dihydrochloride, and the mixture was refluxed for 20 hours. The solvent was distilled off under reduced pressure, and the residue was purified by silica gel column chromatography (elution with a mixture of chloroform and methanol (9:1)). The eluate was dissolved in 80% aqueous acetonitrile, and the solvent was distilled off under reduced pressure, followed by sufficient drying under reduced pressure to obtain 0.92 g of a pale yellow resinous solid.

$^1$H-NMR(CDCl$_3$)δ: 0.88(3H,t,J=7 Hz,CH$_3$), 1.1-1.7(16H, m), 1.49(6H,s,(CH$_3$)$_2$C), 3.33(2H,br dt-like,NHCH$_2$), 3.86

(3H,s,CH$_3$O), 4.4-5.5(2H,br,NH$_2$), 7.02(2H,d,J=9 Hz,ArH), 7.19(2H,d,J=9 Hz,ArH), 7.95(1H,t,J=6 Hz,NHCH$_2$), 9.83 (1H,m,NH$^+$).

Working Example 15

4-Amino-3,6-dihydro-6-dodecyl-2-(4'-methoxyphenethylamino)-1,3,5-triazine hydrochloride (1)

2,4-Diamino-1,6-dihydro-6-dodecyl-1-(4'-methoxyphenethyl)-1,3,5-triazine hydrochloride (2)

100 ml of ethanol, 8.8 ml (37.1 mmol) of 1-tridecanal and 0.8 ml of concentrated hydrochloric acid were added to 5.0 g (18.4 mmol) of N$^1$-(4-methoxyphenethyl)-biguanide hydrochloride, and the mixture was refluxed for 22 hours. The solvent was distilled of f under reduced pressure, and the residue was purified by silica gel column chromatography. The first main fraction eluted with a mixture of chloroform and methanol (9:1.5) was recrystallized from 70% aqueous acetonitrile to obtain 0.92 g of colorless crystals (1) having a melting point of 100 to 102° C., and the second main eluate was recrystallized from 70% aqueous acetonitrile to obtain 1.1 g of colorless crystals (2) having a melting point of 165 to 170° C.

(1) $^1$H-NMR (CDCl$_3$) δ: 0.87(3H,t,J=7 Hz,CH$_3$), 1.2-1.5 (20H,m), 1.64(2H,m,HCCH$_2$), 2.78(2H,t,J=8 Hz,ArCH$_2$CH$_2$NH), 3.50(2H,br dt-like,ArCH$_2$CH$_2$NH), 3.77(3H,s,CH$_3$O), 4.63(1H,br t-like,HCCH$_2$), 6.82(2H,d,J=8 Hz,ArH), 7.12(2H,d,J=8Hz,ArH), 7.46(1H,t,J=6 Hz,ArCH$_2$CH$_2$NH), 8.43, 8.77(each 1H,m,NH,NH$^+$).

By $^1$H—$^1$H COSY, coupling was recognized between HCCH$_2$ (δ: 1.64) and HCCH$_2$ (δ: 4.63), ArCH$_2$CH$_2$NH(δ: 2.78) and ArCH$_2$CH$_2$NH(δ: 3.50), ArCH$_2$CH$_2$NH(δ: 3.50) and ArCH$_2$CH$_2$NH(δ: 7.46) signals. In addition, no coupling was recognized between triazine ring NH and NH$^+$ signals(δ: 8.43, 8.77) and other proton.

(2) $^1$H-NMR (CDCl$_3$) δ: 0.87(3H,t,J=7 Hz,CH$_3$), 1.0-1.5 (20H,m), 1.60(2H,m,HCCH$_2$), 2.91(2H,m,ArCH$_2$CH$_2$), 3.10, 4.02(each 1H,m,m,ArCH$_2$CH$_2$), 3.78(3H,s,CH$_3$O), 4.20(1H,m,HCCH$_2$), 6.84(2H,d,J=9 Hz,ArH), 6.8-7.4(2H,br, NH$_2$), 7.20(2H,d,J=9 Hz,ArH), 8.05(2H,m,NH$_2$), 8.54(1H,br s,NH$^+$).

Working Example 16

4-Amino-3,6-dihydro-6-dodecyl-2-(4'-methoxybenzylamino)-1,3,5-triazine hydrochloride (1)

2,4-Diamino-1,6-dihydro-6-dodecyl-1-(4'-methoxybenzyl)-1,3,5-triazine hydrochloride (2)

100 ml of ethanol, 9.2 ml (38.7 mmol) of 1-tridecanal and 0.8 ml of concentrated hydrochloric acid were added to 5.0 g (19.4 mmol) of N$^1$-(4-methoxybenzyl)-biguanide hydrochloride, and the mixture was refluxed for 24 hours. The solvent was distilled off under reduced pressure, and the residue was purified by silica gel column chromatography. The first main fraction eluted with a mixture of chloroform and methanol (9:1.5) was recrystallized from 70% aqueous acetonitrile to obtain 3.0 g of colorless crystals (1) having a melting point of 162 to 164° C., and the second main eluate was recrystallized from 70% aqueous acetonitrile to obtain 1.3 g of colorless crystals (2) having a melting point of 182 to 184° C.

(1) $^1$H-NMR (CDCl$_3$) δ: 0.87(3H,t,J=7 Hz,CH$_3$), 1.2-1.5 (20H,m), 1.68(2H,m,HCCH$_2$), 3.77(3H,s,CH$_3$O), 4.42(2H, m,ArCH$_2$NH), 4.63(1H,br t-like,HCCH$_2$), 4.9-5.2(1H,br, NH), 6.83(2H,d,J=8 Hz,ArH), 7.18(2H,d,J=8 Hz,ArH), 7.72 (1H,t,J=6 Hz,ArCH$_2$NH), 8.45, 8.69(each 1H,br s,NH,NH$^+$).

(2) $^1$H-NMR (CDCl$_3$) δ: 0.88(3H,t,J=7 Hz,CH$_3$), 1.0-1.6 (20H,m), 1.66(2H,m,HCCH$_2$), 3.78(3H,s,CH$_3$O), 3.97,4.91 (each 1H,m,m,ArCH$_2$), 4.33(1H,m,HCCH$_2$), 6.82(2H,d,J=8 Hz,ArH), 7.13(2H,d,J=8 Hz,ArH), 6.4-8.9(3H,br,NH×3), 8.28(1H,m,NH).

Working Example 17

4-Amino-6-octyl-3,6-dihydro-2-(4'-trifluoromethylbenzylamino)-1,3,5-triazine hydrochloride 100 ml of ethanol, 4.4 ml (25.6 mmol) of 1-nonanal and 0.7 ml of concentrated hydrochloric acid were added to 5.0 g (16.9 mmol) of N$^1$-(4-trifluoromethylbenzyl)-biguanide hydrochloride, and the mixture was refluxed for 26 hours. The solvent was distilled off under reduced pressure, and the residue was purified by silica gel column chromatography (elution with a mixture of chloroform and methanol (9:1.5)) to give a residue, which was dissolved in 80% aqueous ethanol. The solvent was distilled off under reduced pressure, followed by sufficient drying under reduced pressure to obtain 2.3 g of a colorless resinous solid.

$^1$H-NMR (CDCl$_3$) δ: 0.87(3H,t,J=7 Hz,CH$_3$), 1.0-1.5 (12H,m), 1.70(2H,m,HCCH$_2$), 4.57(2H,d,J=6 Hz,ArCH$_2$NH), 4.73(1H,t,J=6 Hz,HCCH$_2$), 5.3-5.8(1H,br,NH), 6.8-7.5(1H,br,NH), 7.40(2H,d,J=8 Hz,ArH), 7.56(2H,d,J=8 Hz,ArH), 8.07(1H,t,J=6 Hz,ArCH$_2$NH), 8.49, 8.59(each 1H,br s,NH,NH$^+$).

Working Example 18

4-Amino-3,6-dihydro-6-decyl-2-(4'-trifluoromethylbenzylamino)-1,3,5-triazine hydrochloride (1)

2,4-Diamino-1,6-dihydro-6-decyl-1-(4'-trifluoromethylbenzyl)-1,3,5-triazine hydrochloride (2)

100 ml of ethanol, 5.3 ml (25.7 mmol) of 1-undecanal and 0.7 ml of concentrated hydrochloric acid were added to 5.01 g (16.9 mmol) of N$^1$-(4-trifluoromethylbenzyl)-biguanide hydrochloride, and the mixture was refluxed for 24 hours. The solvent was distilled off under reduced pressure, and the residue was purified by silica gel column chromatography. The first main fraction eluted with a mixture of chloroform and methanol (9:1.5) was recrystallized from 80% aqueous acetonitrile to obtain 1.41 g of colorless crystals (1) having a melting point of 163 to 166° C., and the second main eluate was recrystallized from 80% aqueous acetonitrile to obtain 0.87 g of colorless crystals (2) having a melting point of 208 to 211° C.

(1) $^1$H-NMR (CDCl$_3$)δ: 0.88(3H,t,J=7 Hz,CH$_3$), 1.0-1.5 (16H,m), 1.70(2H,m,HCCH$_2$), 4.58(2H,d,J=6 Hz,ArCH$_2$NH), 4.73(1H,t,J=6 Hz,HCCH$_2$), 5.6-6.3(1H,br,NH), 6.7-7.3(1H,br,NH), 7.42(2H,d,J=8 Hz,ArH), 7.57(2H,d,J=8 Hz,ArH), 8.08(1H,t,J=6 Hz,ArCH$_2$NH), 8.49,8.50(each 1H,br s,NH,NH$^+$).

(2) $^1$H-NMR(CDCl$_3$)δ: 0.88(3H,t,J=7 Hz,CH$_3$), 1.0-1.8 (18H,m), 4.31,5.19(each 1H,ABq,J=17 Hz,ArCH$_2$), 4.51(1H,m,HCCH$_2$), 6.9-7.4(2H,br,NH$_2$), 7.45(2H,d,J=8 Hz,ArH), 7.63(2H,d,J=8 Hz,ArH), 7.91(2H,br s,NH$_2$), 9.04 (1H,br s,NH$^+$).

Working Example 19

4-Amino-6-undecyl-3,6-dihydro-2-(4'-trifluoromethylbenzylamino)-1,3,5-triazine hydrochloride 100 ml of ethanol, 5.6 ml (25.4 mmol) of 1-dodecanal and 0.7 ml of concentrated hydrochloric acid were added to 5.0 g (16.9 mmol) of N$^1$-(4-trifluoromethylbenzyl)-biguanide hydrochloride, and the mixture was refluxed for 26 hours. The solvent was distilled off under reduced pressure, and the residue was purified by silica gel column chromatography (elution with a mixture of chloroform and methanol (9:1.5)). An aqueous acetonitrile solution was added to the eluate to obtain 2.4 g of colorless crystals having a melting point of 144 to 149° C.

$^1$H-NMR(CDCl$_3$)δ: 0.88(3H,t,J=7 Hz,CH$_3$), 1.1-1.5(18H, m), 1.69(2H,m,HCCH$_2$), 4.57(2H,d,J=6 Hz,ArCH$_2$NH), 4.72(1H,t,J=6 Hz,HCCH$_2$), 5.3-5.8(1H,br,NH), 6.9-7.4(1H, br,NH), 7.40(2H,d,J=8 Hz,ArH), 7.56(2H,d,J=8 Hz,ArH), 8.06(1H,br t-like,ArCH$_2$NH), 8.47,8.58(each 1H,br s,NH, NH$^+$).

Working Example 20

2,4-Diamino-1,6-dihydro-6-heptyl-1-(4'-tert-butylphenyl)-1,3,5-triazine hydrochloride 100 ml of ethanol, 4.3 g (33.1 mmol) of 1-octanal and 0.9 ml of concentrated hydrochloric acid were added to 6.0 g (22.2 mmol) of N$^1$-(4-tert-butylphenyl)-biguanide hydrochloride, and the mixture was refluxed for 20 hours. The solvent was concentrated under reduced pressure, and the residue was cooled. The resulting precipitated colorless crystals were collected by filtration, and recrystallized from 80% aqueous ethanol to obtain 4.2 g of colorless crystals having a melting point of 239 to 241° C.

$^1$H-NMR(DMSO-d$_6$)δ: 0.77(3H,t,J=7 Hz,CH$_3$), 1.0-1.4 (10H,m), 1.24(9H,s,(CH$_3$)$_3$C), 1.49(2H,m,HCCH$_2$), 4.85(1H,m,HCCH$_2$), 6.3-6.8(1H,br,NH), 7.2-7.8(2H,over lap,NH), 7.23(2H,d,J=9 Hz,ArH), 7.47(2H,d,J=9 Hz,ArH), 8.71(1H,br s,NH$^+$).

Working Example 21

6-Octyl-2,4-diamino-1,6-dihydro-1-(4'-tert-butylphenyl)-1,3,5-triazine hydrochloride 100 ml of ethanol, 4.8 ml (27.9 mmol) of 1-nonanal and 0.8 ml of concentrated hydrochloric acid were added to 5.0 g (18.5 mmol) of N$^1$-(4-tert-butylphenyl)-biguanide hydrochloride, and the mixture was refluxed for 15 hours. The solvent was distilled off under reduced pressure, and the residue was purified by silica gel column chromatography (elution with a mixture of chloroform and methanol (9:1.5)), and recrystallized from 70% aqueous acetonitrile to obtain 16 g of colorless crystals having a melting point of 231 to 234° C.

$^1$H-NMR(CDCl$_3$)δ: 0.86(3H,t,J=6 Hz,CH$_3$), 1.1-1.5(12H, m), 1.36(9H,s,(CH$_3$)$_3$C), 1.67(2H,m,HCCH$_2$), 4.91(1H,m, HCCH$_2$), 5.2-5.6(1H,br,NH), 6.4-6.8(1H,br,NH), 7.22(2H,d, J=9 Hz,ArH), 7.55(2H,d,J=9 Hz,ArH), 7.8-8.1(1H,br,NH), 9.77(1H,br s,NH$^+$).

Working Example 22

2,4-Diamino-1,6-dihydro-6-nonyl-1-(4'-tert-butylphenyl)-1,3,5-triazine hydrochloride 100 ml of ethanol, 5.2 g (33.3 mmol) of 1-decanal and 0.9 ml of concentrated hydrochloric acid were added to 6.0 g (22.2 mmol) of N$^1$-(4-tert-butylphenyl)-biguanide hydrochloride, and the mixture was refluxed for 7 hours. The solvent was concentrated under reduced pressure, and the residue was cooled. The resulting precipitated crystals were filtered, and recrystallized from 80% aqueous ethanol to obtain 3.1 g of colorless crystals having a melting point of 238 to 240° C.

$^1$H-NMR(DMSO-d$_6$) δ: 0.78(3H,t,J=7 Hz,CH$_3$), 1.0-1.4 (14H,m), 1.24(9H,s,(CH$_3$)$_3$C), 1.49(2H,m,HCCH$_2$), 4.85(1H,m,HCCH$_2$), 6.4-6.8(1H,br,NH), 7.2-7.8(2H,m, NH), 7.23(2H,d,J=8 Hz,ArH), 7.47(2H,d,J=8 Hz,ArH), 8.74 (1H,m,NH$^+$).

Working Example 23

4-Amino-3,6-dihydro-6-nonyl-2-(4'-tert-butylanilino)-1,3,5-triazine hydrochloride 50 ml of ethanol and 50 ml of water were added to 2.0 g (4.9 mmol) of the compound of Working Example 22, and the mixture was adjusted to a pH of 11 to 12 with 5N sodium hydroxide. The mixture was refluxed for 2 hours, and cooled. The resulting precipitated crystals were filtered, and recrystallized from methanol. After addition of 50 ml of methanol to the crystals, the mixture was dissolved by heating, and 0.9 ml of concentrated hydrochloric acid was added thereto. The solvent was distilled off under reduced pressure, and the residue was dissolved in 70% aqueous acetonitrile. The solvent was distilled off under reduced pressure, followed by sufficient drying under reduced pressure to obtain 1.2 g of a colorless resinous solid.

$^1$H-NMR(CDCl$_3$) δ: 0.85(3H,t,J=7 Hz, CH$_3$), 1.1-1.6 (14H,m), 1.29(9H,s,(CH$_3$)$_3$C), 1.74(2H,m,HCCH$_2$), 4.78(1H,br t-like,HCCH$_2$), 5.0-5.4(1H,br,NH), 7.29(2H,d, J=9 Hz,ArH), 7.36(2H,d,J=9 Hz, ArH), 8.48(1H,m,NH), 8.83 (1H,br s,NH), 9.52 (1H,m,NH$^+$).

Working Example 24

6-Octyl-2,4-diamino-1,6-dihydro-1-(2'-methoxy-5'-tert-butylphenyl)-1,3,5-triazine hydrochloride 100 ml of ethanol, 3.7 g (26.2 mmol) of 1-nonanal and 0.8 ml of concentrated hydrochloric acid were added to 6.0 g (20.0 mmol) of N$^1$-(2-methoxy-5-tert-butylphenyl)-biguanide hydrochloride, and the mixture was refluxed for 20 hours. The solvent was distilled off under reduced pressure, and the residue was purified by silica gel column chromatography (elution with a mixture of chloroform and methanol (9:1.5)). The eluate was dissolved in 80% aqueous ethanol, and the solvent was distilled off under reduced pressure. The residue was recrystallized from ethanol and ether to obtain 2.3 g of pale yellow crystals having a melting point of 217 to 219° C.

$^1$H-NMR(DMSO-d$_6$) δ: 0.77(3H,t,J=7 Hz,CH$_3$), 0.9-1.5 (14H,m), 1.21(9H,s,(CH$_3$)$_3$C), 3.75(3H,s,CH$_3$O), 4.69, 4.89

(1H,m,m,HCCH$_2$), 6.2-6.6(1H,br,NH),7.00-7.60(2H,overlap,NH), 7.09(1H,m,ArH), 7.30(1H,m,ArH), 7.41(1H,m,ArH), 8.58,8.63(1H,m,m,NH$^+$).

Working Example 25

4-Amino-6-octyl-3,6-dihydro-2-(2'-methoxy-5'-tert-butylanilino)-1,3,5-triazine 50 ml of ethanol and 50 ml of water were added to 2.0 g (4.7 mmol) of the compound of Working Example 24, and the mixture was adjusted to a pH of 11 to 12 with 5N sodium hydroxide. The mixture was refluxed for 2 hours, and then cooled. The resulting precipitated crystals were filtered, and recrystallized from ethanol and ether to obtain 0.7 g of pale yellow crystals having a melting point of 129 to 132° C.

$^1$H-NMR(DMSO-d$_6$) δ: 0.87(3H,t,J=7 Hz,CH$_3$), 1.0-1.7 (14H,m), 1.28(9H,s,(CH$_3$)$_3$C), 3.76(3H,s,CH$_3$O), 4.77(1H, br t-like,HCCH$_2$), 5.3-5.7(1H,br,NH), 6.75(1H,d,J=8 Hz,ArH), 6.96(1H,d,d,J=3, 8 Hz, ArH), 7.26(1H,br s,ArH), 7.2-7.4(2H,m,NH×2), 8.12(1H,m,NH).

Working Example 26

6-Octyl-2,4-diamino-1,6-dihydro-1-(4'-trifluoromethoxyphenyl)-1,3,5-triazine hydrochloride 100 ml of ethanol, 4.4 ml (25.6 mmol) of 1-nonanal, and 0.7 ml of concentrated hydrochloric acid were added to 5.0 g (16.8 mmol) of N$^1$-(4-trifluoromethoxyphenyl)-biguanide hydrochloride, and the mixture was refluxed for 9 hours. The solvent was distilled off under reduced pressure, and the residue was recrystallized from hydrous ethanol to obtain 0.7 g of colorless crystals having a melting point of 216 to 220° C.

$^1$H-NMR(DMSO-d$_6$) δ: 0.84(3H,t,J=7 Hz,CH$_3$), 1.0-1.4 (12H,m), 1.55(2H,m,HCCH$_2$), 4.99(1H,br t-like,HCCH$_2$), 6.7-7.0(1H,br,NH), 7.3-7.7(2H,over lap,NH), 7.51(2H,d,J=9 Hz,ArH), 7.55(2H,d,J=9 Hz,ArH), 7.7-7.9(1H,br,NH), 8.91 (1H,br s,NH$^+$).

Working Example 27

4-Amino-6-octyl-3,6-dihydro-2-(4'-trifluoromethoxyanilino)-1,3,5-triazine hydrochloride 80 ml of ethanol and 50 ml of water were added to 6.4 g of the compound of Working Example 26 (the solvent of the hydrous ethanol in the recrystallization mother liquid was distilled off), and the mixture was adjusted to a pH of 11 to 12 with 5N sodium hydroxide. The mixture was refluxed for 2 hours, and the solvent was distilled off under reduced pressure to give a residue, which was extracted with chloroform. The extract was concentrated under reduced pressure to give a residue, which was dissolved in 50 ml of methanol. After 2.5 ml of concentrated hydrochloric acid was added thereto, the solvent was distilled off under reduced pressure. The residue was purified by silica gel column chromatography (elution with a mixture of chloroform and methanol (8:2)), and the eluate was dissolved in 70% aqueous acetonitrile. The solvent was distilled off under reduced pressure, and the residue was sufficiently dried under reduced pressure to obtain 2.0 g of a colorless solid.

$^1$H-NMR(CD$_3$OD)δ: 0.90(3H,t,J=7 Hz,CH$_3$), 1.2-1.6 (12H,m), 1.73(2H,m,HCCH$_2$), 4.83(1H,m,HCCH$_2$), 7.27 (2H,d,J=9 Hz,ArH), 7.56(2H,d,J=9 Hz,ArH).

Working Example 28

2,4-Diamino-1,6-dihydro-6-nonyl-1-(4'-trifluoromethoxyphenyl)-1,3,5-triazine hydrochloride 100 ml of ethanol, 4.7 ml (25.1 mmol) of 1-decanal and 0.7 ml of concentrated hydrochloric acid were added to 5.0 g (16.8 mmol) of N$^1$-(4-trifluoromethoxyphenyl)-biguanide hydrochloride, and the mixture was refluxed for 16 hours. The solvent was distilled off under reduced pressure, and the residue was purified by silica gel column chromatography (elution with a mixture of chloroform and methanol (8:1.5)), and recrystallized from 80% ethanol to obtain 1.1 g of colorless crystals having a melting point of 213 to 215° C.

$^1$H-NMR(CDCl$_3$)δ: 0.87(3H,t,J=7 Hz,CH$_3$), 1.0-1.8(16H, m), 4.93(1H,m,HCCH$_2$), 5.8-6.4(1H,br,NH), 6.89(1H,m,NH), 7.41(4H,m,ArH), 7.79(2H,m,NH$_2$), 9.73 (1H,m,NH$^+$).

Working Example 29

4-Amino-3,6-dihydro-6-nonyl-2-(4'-trifluoromethoxyanilino)-1,3,5-triazine hydrochloride 50 ml of ethanol and 50 ml of water were added to 2.8 g of the compound of Working Example 28 (the 80% ethanol solvent in the recrystallization mother liquid was distilled off), and the pH of the mixture was adjusted to 11 to 12 with 5N sodium hydroxide. The mixture was refluxed for 2 hours, and cooled. The resulting precipitated crystals were filtered to obtain 2.4 g of colorless crystals. Then, the crystals were dissolved in 50 ml of methanol, and 1 ml of concentrated hydrochloric acid was added thereto. The solvent was distilled off under reduced pressure, and the residue was dissolved in 70% aqueous acetonitrile. The solvent was distilled off under reduced pressure, followed by sufficient drying under reduced pressure to obtain 16 g of a colorless solid.

$^1$H-NMR(CDCl$_3$-D$_2$O)δ: 0.85(3H,t,J=7 Hz,CH$_3$), 1.1-1.6 (14H,m), 1.76(2H,m,HCCH$_2$), 4.82(1H,t,J=6 Hz,HCCH$_2$), 7.13(2H,d,J=9 Hz,ArH), 7.52(2H,d,J=9 Hz,ArH).

Working Example 30

2,4-Diamino-1,6-dihydro-1-(2',3',4'-trifluorophenyl)-6-nonyl-1,3,5-triazine hydrochloride 100 ml of ethanol, 5.3 ml (28.1 mmol) of 1-decanal and 0.8 ml of concentrated hydrochloric acid were added to 5.0 g (18.7 mmol) of N$^1$-(2,3,4-trifluorophenyl)-biguanide hydrochloride, and the mixture was refluxed for 4 hours. The solvent was distilled off under reduced pressure, and the residue was purified by silica gel column chromatography (elution with a mixture of chloroform and methanol (9:2)), and recrystallized from 80% aqueous acetonitrile to obtain 4.7 g of colorless crystals having a melting point of 210 to 212° C.

$^1$H-NMR(CDCl$_3$)δ: 0.87(3H,t,J=7 Hz,CH$_3$), 1.0-1.8(16H, m), 4.88(1H,br t-like,HCCH$_2$), 6.7-7.5(2H,br,NH$_2$), 7.19 (2H,m,ArH), 7.5-7.9(2H,br,NH$_2$), 9.63(1H,br s,NH$^+$).

Working Example 31

2,4-Diamino-1,6-dihydro-1-(2',3',4'-trifluorophenyl)-6-decyl-1,3,5-triazine hydrochloride 100 ml of ethanol, 4.8 g (28.2 mmol) of 1-undecanal and 0.8 ml of concentrated hydrochloric acid were added to 5.0 g (18.7 mmol) of $N^1$-(2,3,4-trifluorophenyl)-biguanide hydrochloride, and the mixture was refluxed for 24 hours. The solvent was distilled off under reduced pressure, and the residue was purified by silica gel column chromatography (elution with a mixture of chloroform and methanol (9:1.5)), and recrystallized from 80% aqueous acetonitrile to obtain 3.2 g of colorless crystals having a melting point of 210 to 213° C.

$^1$H-NMR(DMSO-$d_6$)δ: 0.85(3H,t,J=7 Hz,CH$_3$), 1.1-1.5 (16H,m), 1.55(2H,m,HCC$\underline{H}_2$), 4.98(1H,m, $\underline{H}$CCH$_2$), 6.9-7.1 (1H,br,NH), 7.4-7.8(2H,br,NH×2), 7.51(2H,m,ArH), 7.8-8.1 (1H,br,NH), 8.99(1H,br s,NH$^+$).

Working Example 32

4-Amino-3,6-dihydro-6-decyl-2-(2',3',4'-trifluoroanilino)-1,3,5-triazine hydrochloride 50 ml of ethanol and 50 ml of water were added to 2.8 g (6.6 mmol) of the compound of Working Example 31, and the pH of the mixture was adjusted to 11 to 12 with 5N sodium hydroxide. The mixture was refluxed for 2 hours, and cooled. The resulting precipitated crystals were filtered, and recrystallized from 70% aqueous acetonitrile to obtain 1.3 g of colorless crystals having a melting point of 145 to 148° C. Then, 30 ml of methanol was added to 0.8 g (2.1 mmol) of the above crystals, and the mixture was dissolved by heating. After addition of 0.4 ml of concentrated hydrochloric acid, the solvent was distilled off under reduced pressure, and recrystallized from 80% aqueous ethanol to obtain 0.4 g of colorless crystals having a melting point of 60 to 65° C.

$^1$H-NMR(CDCl$_3$) δ: 0.87(3H,t,J=7 Hz,CH$_3$), 1.0-1.6(16H, m), 1.80(2H,m,HCC$\underline{H}_2$), 4.90(1H,m,$\underline{H}$CCH$_2$), 5.6-6.0(1H, br,NH), 6.96,7.42(each 1H,m,ArH), 7.5-7.8(1H,br,NH), 8.9-9.7(3H,br,NH,NH$^+$).

Working Example 33

2,4-Diamino-1,6-dihydro-6-decyl-1-(2',4'-difluorophenyl)-1,3,5-triazine hydrochloride 100 ml of ethanol, 5.1 g (29.9 mmol) of 1-undecanal and 0.8 ml of concentrated hydrochloric acid were added to 5.0 g (20.0 mmol) of $N^1$- (2,4-difluorophenyl)-biguanide hydrochloride, and the mixture was refluxed for 8 hours. The solvent was distilled off under reduced pressure, and the residue was purified by silica gel column chromatography (elution with a mixture of chloroform and methanol mixed solution (9:1.5)), and recrystallized from 80% aqueous ethanol to obtain 1.7 g of colorless crystals having a melting point of 207 to 209° C.

$^1$H-NMR(CD$_3$OD)δ: 0.89(3H,t,J=7 Hz,CH$_3$), 1.2-1.5 (16H,m), 1.71(2H,m,HCC$\underline{H}_2$), 4.92(1H,m,$\underline{H}$CCH$_2$), 7.10-7.32(2H,m,ArH), 7.48-7.62(1H,m,ArH).

Working Example 34

4-Amino-3,6-dihydro-6-decyl-2-(2'4'-difluoroanilino)-1,3,5-triazine 50 ml of ethanol and 50 ml of water were added to 4.0 g (10.0 mmol) of the compound of Working Example 33 (the 80% ethanol solvent in the recrystallization mother liquid was distilled off), and the pH of the mixture was adjusted to 11 to 12 with 5N sodium hydroxide. The mixture was refluxed for 2 hours and cooled. The resulting precipitated crystals were filtered, and recrystallized from 80% aqueous ethanol to obtain 2.5 g of colorless crystals having a melting point of 151 to 152° C.

$^1$H-NMR(CDCl$_3$)δ: 0.88(3H,t,J=7 Hz,CH$_3$), 1.1-1.5(16H, m), 1.63(2H,m,HCC$\underline{H}_2$), 4.78(1H,t,J=6 Hz,$\underline{H}$CCH$_2$), 6.7-6.9 (2H,m,ArH), 8.0-8.2(1H,m,ArH).

Working Example 35

6-Undecyl-2,4-diamino-1,6-dihydro-1-(2',4'-difluorophenyl)-1,3,5-triazine hydrochloride 100 ml of ethanol, 6.6 ml (29.9 mmol) of 1-dodecanal and 0.9 ml of concentrated hydrochloric acid were added to 5.0 g (20.0 mmol) of $N^1$-(2,4-difluorophenyl)-biguanide hydrochloride, and the mixture was refluxed for 20 hours. The solvent was distilled off under reduced pressure, and the residue was purified by silica gel column chromatography (elution with a mixture of chloroform and methanol (9:1.5)), and recrystallized from 70% aqueous acetonitrile to obtain 3.9 g of colorless crystals having a melting point of 206 to 208° C.

$^1$H-NMR(CDCl$_3$)δ: 0.88(3H,t,J=7 Hz,CH$_3$), 1.0-1.4(18H, m), 1.61(2H,m,HCC$\underline{H}_2$), 4.85(1H,m,$\underline{H}$CCH$_2$), 6.1-6.7(1H, br,NH), 6.8-7.3(1H,over lap,NH), 7.0-7.2(2H,m,ArH), 7.3-7.5(1H,m,ArH), 7.80(2H,m,NH$_2$), 9.63(1H,br s,NH$^+$).

Working Example 36

4-Amino-3,6-dihydro-6-undecyl-2-(2',4'-difluoroanilino)-1,3,5-triazine hydrochloride 60 ml of ethanol and 60 ml of water were added to 3.0 g (7.2 mmol) of the compound of Working Example 35, and the pH of the mixture was adjusted to 11 to 12 with 5N sodium hydroxide. The mixture was refluxed for 2 hours, and cooled. The resulting precipitated crystals were filtered off, and further recrystallized from 80% aqueous ethanol to obtain 2.3 g of colorless crystals. Then, 30 ml of methanol was added to 0.8 g (2.1 mmol) of the crystals, and the mixture was dissolved under heating. After addition of 0.4 ml of concentrated hydrochloric acid, the solvent was distilled off under reduced pressure, followed by recrystallization from 80% aqueous ethanol to obtain 0.7 g of colorless crystals having a melting point of 144 to 146° C.

$^1$H-NMR(CDCl$_3$) δ: 0.87(3H,t,J=7 Hz,CH$_3$), 1.0-1.6(18H, m), 1.78(2H,m,HCC$\underline{H}_2$), 4.85(1H,m,$\underline{H}$CCH$_2$), 5.4-5.8(1H, br,NH), 6.7-6.9(2H,m,ArH), 7.3-7.7(1H,over lap,NH), 7.5-7.7(1H,m,ArH), 9.03,9.16,9.36(each 1H,m,NH,NH$^+$).

Working Example 37

4-Octylamino-3,6-dihydro-6,6-dimethyl-2-(4'-methylbenzylamino)-1,3,5-triazine

40 ml of methanol, 80 ml of acetone and 16 ml (16.2 mmol) of piperidine were added to 3.0 g (7.7 mmol) of $N^1$-(4-methylbenzyl)-$N^5$-octyl-biguanide dihydrochloride, and the mixture was refluxed for 23 hours. The solvent was distilled off under reduced pressure, and the residue was purified by silica gel column chromatography (elution with a mixture of chloroform, methanol and acetic acid (9:0.5:0.5)). 50 ml of ethanol and 50 ml of water were added to the resulting colorless resinous solid, and the pH of the mixture was adjusted to 11 to 12 with 5N sodium hydroxide. The mixture was refluxed for 1 hour, and the solvent was distilled off under reduced pressure. The residue was washed with water, and dried well under reduced pressure to obtain 1.3 g of a colorless solid.

$^1$H-NMR(CDCl$_3$)δ: 0.87(3H,t,J=7 Hz,CH$_3$), 1.1-1.6(12H, m), 1.33(6H,s,(CH$_3$)$_2$C), 2.31(3H,s,ArCH$_3$), 3.16(2H,t,J=7 Hz,NHCH$_2$), 4.36(2H,br s,ArCH$_2$), 7.09(2H,d,J=8 Hz,ArH), 7.18(2H,d,J=8 Hz,ArH).

Working Example 38

3,6-Dihydro-6,6-dimethyl-4-decylamino-2-(4'-methoxybenzylamino)-1,3,5-triazine acetate (1)

3,6-Dihydro-6,6-dimethyl-4-decylamino-2-(4'-methoxybenzylamino)-1,3,5-triazine methanesulfonate (2)

55 ml of 5N aqueous sodium hydroxide was added to 40 g (92.1 mmol) of $N^1$-(4-methoxybenzyl)-$N^5$-decylbiguanide dihydrochloride in 400 ml of methanol, and the mixture was stirred at 60° C. for 30 minutes. The solvent was distilled off under reduced pressure, and the residue was extracted with chloroform. The extract was washed with water, and the solvent was distilled off under reduced pressure to give a residue, to which were added 450 ml of acetone, 150 ml of methanol and 6.4 ml (46.6 mmol) of piperidine. The mixture was refluxed for 15 hours, and the solvent was distilled off under reduced pressure. The residue was washed with water while stirring, dissolved in ethyl acetate, and washed with water. After removal of the solvent by evaporation under reduced pressure, the residue was dried under reduced pressure to obtain 37 g of a colorless solid (1). Then, 2.3 g (5.9 mmol) of the solid was dissolved in 100 ml of methanol, and 169 g (19.7 mmol) of methanesulfonic acid was added thereto. The solvent was distilled off under reduced pressure, and the residue was dissolved in 70% aqueous acetonitrile. The solvent was distilled off under reduced pressure, and the residue was purified by silica gel column chromatography (elution with a mixture of chloroform and methanol (9:1.5)). Crystallization took place upon addition of ether to obtain 1.9 g of colorless crystals (2) having a melting point of 56 to 58° C.

(2) $^1$H-NMR(CDCl$_3$)δ: 0.87(3H,t,J=7 Hz,CH$_3$), 1.0-1.6 (16H,m), 1.39(6H,s,(CH$_3$)$_2$C), 2.75(3H,s,CH$_3$SO$_3^-$), 3.28(2H,br dt-like,NHCH$_2$), 3.78(3H,s,CH$_3$O), 4.43(2H,d, J=6 Hz,ArCH$_2$), 6.82(2H,d,J=9 Hz,ArH), 7.1-7.3(1H,over lap,NH), 7.20(2H,d,J=9 Hz,ArH), 7.53(1H,t,J=6 Hz,N HCH$_2$), 7.92,8.01(1H,br s,NH,NH$^+$).

Working Example 39

3,6-Dihydro-6,6-dimethyl-4-decylamino-2-(4'-methoxybenzylamino)-1,3,5-triazine malonate

3.0 g (7.5 mmol) of the compound (1) of Working Example 38 was dissolved in 30 ml of 70% aqueous acetonitrile, and to the solution was added 0.85 g (8.17 mmol) of malonic acid. The mixture was dissolved by heating, and then cooled to obtain 3.0 g of colorless crystals having a melting point of 109 to 112° C.

$^1$H-NMR(CDCl$_3$)δ: 0.87(3H,t,J=7 Hz,CH$_3$), 1.0-1.6(16H, m), 1.44(6H,s,(CH$_3$)$_2$C), 3.15(2H,s,HOOCH$_2$COO$^-$), 3.33(2H,br dt-like,NHCH$_2$), 3.79(3H,s,CH$_3$O), 4.48(2H,d, J=6 Hz,ArCH$_2$), 6.85(2H,d,J=9 Hz,ArH), 7.23(2H,d,J=9 Hz,ArH), 7.72, 8.12(each 1H,br t-like,NH), 8.38, 8.47(each 1H,br s,NH,NH$^+$).

Working Example 40

3,6-Dihydro-6,6-dimethyl-4-decylamino-2-(4'-methoxybenzylamino)-1,3,5-triazine oxalate

6.5 g (16.2 mmol) of the compound (1) of Working Example 38 was dissolved in 50 ml of 30% aqueous acetonitrile, and 3.0 g (23.8 mmol) of oxalic acid dihydrate was added thereto. The mixture was dissolved under heating, and then cooled. The resulting crystals were recrystallized from 50% aqueous acetonitrile to obtain 2.9 g of colorless crystals having a melting point of 101 to 103° C.

$^1$H-NMR(CDCl$_3$)δ: 0.87(3H,t,J=7 Hz,CH$_3$), 1.0-1.6(16H, m), 1.45(6H,s,(CH$_3$)$_2$C), 3.31(2H,br dt-like,NHCH$_2$), 3.78 (3H,s,CH$_3$O), 4.46(2H,d,J=5 Hz,ArCH$_2$), 6.4-6.8(1H,br, NH), 6.83(2H,d,J=9 Hz,ArH), 7.22(2H,d,J=9 Hz,ArH), 7.64, 7.92,8.49,8.59(each 1H,m,COOH,NH×2,NH$^+$).

Working Example 41

3,6-Dihydro-6,6-dimethyl-4-decylamino-2-benzylamino-1,3,5-triazine acetate (1)

3,6-Dihydro-6,6-dimethyl-4-decylamino-2-benzylamino-1,3,5-triazine malonate (2)

140 ml of methanol, 100 ml of acetone and 0.6 ml of concentrated hydrochloric acid were added to 8.5 g (21.0 mmol) of $N^1$-benzyl-$N^5$-decyl-biguanide dihydrochloride, and the mixture was refluxed for 24 hours. The solvent was distilled off under reduced pressure to give a residue, which was dissolved in 150 ml of ethanol. To the solution were added 100 ml of water and 10 ml of 5N aqueous sodium hydroxide, and the mixture was refluxed for 1.5 hours. The solvent was distilled off under reduced pressure, and the residue was extracted with ethyl acetate. The extract was washed with water, concentrated under reduced pressure to remove the solvent, and dried well under reduced pressure to obtain 8 g of a colorless solid (1). Then, 3.6 g (9.6 mmol) of the solid was dissolved in 30 ml of 70% aqueous acetonitrile, and to the solution was added 16 g (15.4 mmol) of malonic acid. The mixture was dissolved under heating, and then cooled. The resulting crystals were recrystallized from 70% aqueous acetonitrile to obtain 3.9 g of colorless crystals (2) having a melting point of 78 to 81° C.

(2) $^1$H-NMR(CDCl$_3$)δ: 0.87(3H,t,J=7 Hz,CH$_3$), 1.0-1.6 (16H,m), 1.45(6H,s,(CH$_3$)$_2$C), 3.22(2H,s,HOOCH$_2$COO$^-$), 3.27(2H,br dt-like,NHCH$_2$), 4.55(2H,d,J=5 Hz,ArCH$_2$), 7.2-7.4(5H,m,ArH), 7.50,7.98,8.29,8.43(each 1H,m).

Working Example 42

3,6-Dihydro-6,6-dimethyl-4-decylamino-2-benzy-lamino-1,3,5-triazine oxalate 3.6 g (9.6 mmol) of the compound (1) of Working Example 41 was dissolved in 30 ml of 70% aqueous acetonitrile, and to the solution was added 2.0 g (15.9 mmol) of oxalic acid dehydrate. The mixture was dissolved under heating, and then cooled. The resulting crystals were recrystallized from 70% aqueous acetonitrile to obtain 4.0 g of colorless crystals having a melting point of 95 to 98° C.

$^1$H-NMR(CDCl$_3$)δ: 0.87(3H,t,J=7 Hz,CH$_3$), 1.0-1.6(16H, m), 1.46(6H,m,(CH$_3$)$_2$C), 3.27(2H,br dt-like,NHCH$_2$), 4.53 (2H,d,J=5 Hz,ArCH$_2$), 7.2-7.3(5H,m,ArH), 7.2-7.7(2H,br), 7.99(1H,m), 8.52(2H,m).

Working Example 43

4-Amino-6-undecyl-3,6-dihydro-2-benzylamino-1,3,5-triazine hydrochloride (1)

6-Undecyl-2,4-diamino-1,6-dihydro-1-benzyl-1,3,5-triazine hydrochloride (2)

160 ml of ethanol, 13.0 g (70.5 mmol) of 1-dodecanal and 1.5 ml of concentrated hydrochloric acid were added to 8.0 g (35.1 mmol) of N$^1$-benzyl-biguanide hydrochloride. The mixture was refluxed for 16 hours, and concentrated under reduced pressure to remove the solvent. The residue was purified by silica gel column chromatography, and the first main fraction eluted with a mixture of chloroform and methanol (9:1.5) was recrystallized from 80% aqueous ethanol to obtain 3.1 g of colorless crystals (1) having a melting point of 152 to 155° C. The second main fraction was recrystallized from 80% aqueous ethanol to obtain 0.9 g of colorless crystals (2) having a melting point of 153 to 156° C.

(1) $^1$H-NMR (CDCl$_3$) δ: 0.88(3H,t,J=7 Hz,CH$_3$), 1.0-1.5 (18H,m), 1.68(2H,m,HCCH$_2$), 4.50(2H,d,J=6 Hz,ArCH$_2$NH), 4.67(1H,t,J=5 Hz,HCCH$_2$), 7.2-7.4(6H,m,ArH, NH), 7.77(1H,br t-like,ArCH$_2$NH), 8.31,8.63(each 1H,m, NH,NH$^+$).

$^1$H-NMR spectrum indicates the following structure (19). In particular, since coupling was recognized between methylene proton at benzyl position (δ: 4.50) and NH (δ: 7.77) signals, it was confirmed that the benzyl was attached to NH at position 2.

(2) $^1$H-NMR (CD$_3$OD) δ: 0.90(3H,t,J=7 Hz,CH$_3$), 1.1-1.5 (18H,m), 1.69(2H,m,HCCH$_2$), 4.45,4.87(each 1H,ABq,J=16 Hz,ArCH$_2$NH), 4.62(1H,dd,J=4,7 Hz,HCCH$_2$), 7.3-7.5(5H, m,ArH).

$^1$H-NMR spectrum indicates a compound of the following structure (4). In particular, since AB-type signals (δ: 4.45, 4.87) of methylene proton at benzyl position were recognized, it was confirmed that the benzyl was attached to a considerably fixed position of 1.

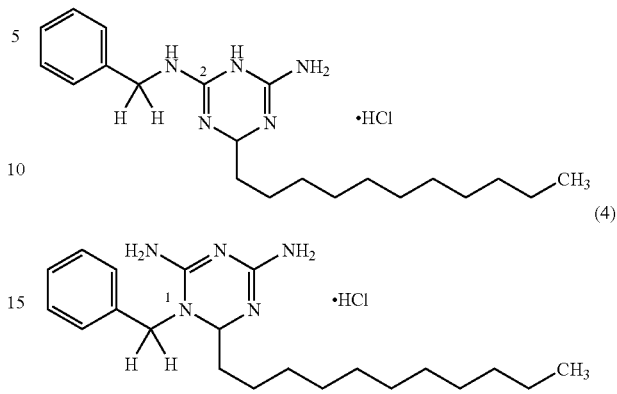

Working Example 44

4-Amino-3,6-dihydro-6-dodecyl-2-benzylamino-1,3,5-triazine hydrochloride 150 ml of ethanol, 6.5 g (32.8 mmol) of 1-tridecanal and 0.9 ml of concentrated hydrochloric acid were added to 5.0 g (22.0 mmol) of N$^1$-benzyl-biguanide hydrochloride. The mixture was refluxed for 17 hours, and concentrated under reduced pressure to remove the solvent. The residue was dissolved in 100 ml of ethanol, and the solution was added to 50 ml of water and 10 ml of 5N aqueous sodium hydroxide. The mixture was refluxed for 2 hours, and the solvent was distilled off under reduced pressure. The residue was extracted with ethyl acetate, and the extract was washed with water. After addition of 5 ml of concentrated hydrochloric acid, the solvent was distilled off under reduced pressure. The residue was purified by silica gel column chromatography (elution with a mixture of chloroform and methanol (9:1.5)), and further recrystallized from 80% aqueous ethanol to obtain 1.2 g of colorless crystals having a melting point of 168 to 170° C.

$^1$H-NMR (CDCl$_3$) δ: 0.88(3H,t,J=7 Hz,CH$_3$), 1.0-1.5 (20H,m), 1.69(2H,m,HCCH$_2$), 4.53(2H,d,J=6 Hz,ArCH$_2$), 4.72(1H,t,J=6 Hz,HCCH$_2$), 7.2-7.4(6H,m,ArH,NH), 7.78(1H,br t-like,NH), 8.30,8.55(1H,br s,NH,NH$^+$).

Working Example 45

6-Undecyl-1-(4'-chlorophenyl)-2,4-diamino-1,6-dihydro-6-methyl-1,3,5-triazine hydrochloride 200 ml of ethanol, 10.1 g (50.9 mmol) of 2-tridecanone and 2.0 ml of concentrated hydrochloric acid were added to 12.0 g (48.4 mmol) of N$^1$-phenyl-biguanide hydrochloride, and the mixture was refluxed for 40 hours. The solvent was distilled off under reduced pressure, and the residue was purified two times by silica gel column chromatography (elution with a mixture of chloroform and methanol (8:1.5) and subsequently with a mixture of chloroform/methanol/acetic acid (8:0.5:0.5→8:1:1)). The eluate was dissolved in 80% aqueous ethanol, and the solvent was distilled off under reduced pressure. The residue was dried well under reduced pressure to obtain 6.6 g of a pale yellow resinous solid.

$^1$H-NMR (CDCl$_3$) δ: 0.88(3H,t,J=7 Hz,CH$_3$), 1.0-1.6 (18H,m), 1.51(3H,s,H$_3$CCCH$_2$), 1.72(2H,m,H$_3$CCCH$_2$), 5.0-5.4(1H,br,NH), 7.1-7.3(1H,over lap,NH), 7.24(2H,d,J=9 Hz,ArH), 7.45(2H,d,J=9 Hz,ArH), 8.58,9.04,9.58(each 1H,br s,NH×2,NH$^+$).

Working Example 46

4-Amino-6-undecyl-3,6-dihydro-6-methyl-2-benzylamino-1,3,5-triazine hydrochloride 180 ml of ethanol, 13.0 g(65.5 mmol) of 2-tridecanone and 1.5 ml of concentrated hydrochloric acid were added to 8.0 g (35.1 mmol) of N$^1$-benzyl-biguanide hydrochloride. The mixture was refluxed for 24 hours, and the solvent was distilled off under reduced pressure. The residue was recrystallized from ethanol to remove recovered N$^1$-benzyl-biguanide hydrochloride, and the solvent of the recrystallization mother liquid was distilled off under reduced pressure. The residue was purified by silica gel column chromatography (elution with a mixture of chloroform/methanol/acetic acid (8:1.2:1)) to obtain 3.3 g of a resinous solid. Then, the resinous solid was dissolved in 50 ml of ethanol, and to the solution were added 50 ml of water and 2.5 ml of 5N aqueous sodium hydroxide. The mixture was refluxed for 2 hours, and the solvent was distilled off under reduced pressure. The residue was extracted with ethyl acetate, and the extract was washed with water. After addition of 2 ml of concentrated hydrochloric acid, the solvent was distilled off under reduced pressure to give a residue, which was recrystallized from 70% aqueous acetonitrile to obtain 2.6 g of white yellow crystals having a melting point of 104 to 105° C.

$^1$H-NMR (CDCl$_3$) δ: 0.88(3H,t,J=7 Hz,CH$_3$), 1.1-1.5 (18H,m), 1.40(3H,s,C$\underline{H}_3$CCH$_2$), 1.64(2H,m,CH$_3$CC$\underline{H}_2$), 4.50(2H,d,J=6 Hz,ArC$\underline{H}_2$NH), 7.2-7.4(6H,m,ArH,NH), 7.61 (1H,br t-like,ArCH$_2$N$\underline{H}$), 8.60,8.70(1H,br s,NH,NH$^+$).

Working Example 47

3,6-Dihydro-6,6-dimethyl-4-nonylamino-2-benzylamino-1,3,5-triazine carbonate 140 ml of methanol, 100 ml of acetone and 0.5 ml of concentrated hydrochloric acid were added to 7.2 g (18.4 mmol) of N$^1$-benzyl-N$^5$-nonyl-biguanide dihydrochloride. The mixture was refluxed for 16 hours, and the solvent was distilled off under reduced pressure. The residue was dissolved in 100 ml of ethanol, and to the solution were added 80 ml of water and 8 ml of 5N aqueous sodium hydroxide. The mixture was refluxed for 1.5 hours, concentrated under reduced pressure, and extracted with ethyl acetate. The extract was washed with water, and carbon dioxide gas was bubbled through the solution. The resulting precipitated crystals were filtered to obtain 4.7 g of colorless crystals. The crystals were recrystallized from 70% aqueous acetonitrile to obtain colorless crystals having a melting point of 85 to 88° C.

$^1$H-NMR(CD$_3$OD) δ: 0.89(3H,t,J=7 Hz,CH$_3$), 1.2-1.6 (14H,m), 1.42(3H,s,(CH$_3$)$_2$C), 3.24(2H,t,J=7 Hz,NHC$\underline{H}_2$), 4.49(2H,s,ArCH$_2$), 7.2-7.4(5H,m,ArH).

Working Example 48

3,6-Dihydro-6,6-dimethyl-4-nonylamino-2-benzylamino-1,3,5-triazine acetate 300 ml of methanol, 250 ml of acetone and 1.2 ml of concentrated hydrochloric acid were added to 18.2 g (46.6 mmol) of N$^1$-benzyl-N$^5$-nonyl-biguanide dihydrochloride. The mixture was refluxed for 22 hours, and the solvent was distilled off under reduced pressure. The residue was dissolved in 300 ml of ethanol, and to the solution were added 200 ml of water and 18 ml of 5N aqueous sodium hydroxide. The mixture was refluxed for 1.5 hours, concentrated under reduced pressure, and extracted with ethyl acetate. The extract was washed with water, and the solvent was distilled off under reduced pressure to obtain 18.9 g of colorless crystals.

3.0 g of colorless crystals were recrystallized from ethanol/ether to obtain 1.9 g of colorless crystals having a melting point of 99 to 102° C.

$^1$H-NMR(CDCl$_3$)δ: 0.87(3H,t,J=7 Hz,CH$_3$), 1.0-1.4(12H, m), 1.31(6H,s,(CH$_3$)$_2$C), 1.44(2H,m,NHCH$_2$C$\underline{H}_2$), 1.92(3H, s,C$\underline{H}_3$COOH), 3.22(2H,br dt-like,NHC$\underline{H}_2$CH$_2$), 4.48(2H,d, J=5 Hz,ArCH$_2$), 7.2-7.3(5H,m,ArH), 8.16, 8.68(each 1H,br t-like,NH), 9.09,9.25(each 1H,br s,NH,NH$^+$).

Working Example 49

3,6-Dihydro-6,6-dimethyl-4-nonylamino-2-benzylamino-1,3,5-triazine hydrobromide 5.1 g (13.6 mmol) of colorless crystals of Working Example 48 were dissolved in 20 ml of 30% aqueous acetonitrile, and to the solution was added 5 ml of 47% hydrobromic acid. The mixture was cooled, and the resulting precipitated crystals were filtered, and recrystallized from 70% aqueous acetonitrile to obtain 5.0 g of colorless crystals having a melting point of 91 to 93° C.

$^1$H-NMR(CDCl$_3$)δ: 0.87(3H,t,J=7 Hz,CH$_3$), 1.0-1.6(14H, m), 1.43(6H,s,(CH$_3$)$_2$C), 3.26(2H,br dt-like,NHC$\underline{H}_2$), 4.52 (2H,d,J=6 Hz,ArCH$_2$), 6.87(1H,br t-like,NH), 7.1-7.4(6H,m, ArH,NH), 8.16,8.31(each 1H,br s,NH,NH$^+$).

Working Example 50

3,6-Dihydro-6,6-dimethyl-4-decylamino-2-benzylamino-1,3,5-triazine acetate 110 ml of methanol, 80ml of acetone and 0.5 ml of concentrated hydrochloric acid were added to 6.8 g (16.9 mmol) of N$^1$-benzyl-N$^5$-decyl-biguanide dihydrochloride. The mixture was refluxed for 22 hours, and the solvent was distilled off under reduced pressure, and the residue was dissolved in 100 ml of ethanol. To the solution were added 80 ml of water and 7 ml of 5N aqueous sodium hydroxide. The mixture was refluxed for 1.5 hours, concentrated under reduced pressure, and extracted with ethyl acetate. The extract was washed with water, and the solvent was distilled off under reduced pressure. The residue was recrystallized from ethanol/ether to obtain 2.9 g of colorless crystals having a melting point of 106 to 108° C.

$^1$H-NMR(CDCl$_3$) δ: 0.88(3H,t,J=7 Hz,CH$_3$), 1.0-1.6(16H, m), 1.31(6H,s,(CH$_3$)$_2$C), 1.92(3H,s,C$\underline{H}_3$COOH), 3.23(2H, m,NHC$\underline{H}_2$), 4.47(2H,m,ArCH$_2$), 7.1-7.4(5H,m,ArH), 8.18, 8.69, 9.10, 9.25(each 1H, m,NH×3,NH$^+$).

Working Example 51

3,6-Dihydro-6,6-dimethyl-4-undecylamino-2-benzylamino-1,3,5-triazine oxalate 140 ml of methanol, 100 ml of acetone and 0.5 ml of concentrated hydrochloric acid were added to 8.0 g (19.1 mmol) of N$^1$-benzyl-N$^5$-nonyl-biguanide dihydrochloride. The mixture was refluxed for 20 hours, and the solvent was distilled off under reduced pressure. The residue was dissolved in 100 ml of ethanol, and to the solution were added 60 ml of water and 8.4 ml of 5N aqueous sodium hydroxide. The mixture was refluxed for 1.5 hours, concentrated under reduced pressure, and extracted with ethyl acetate. The extract was washed with water, and the solvent was distilled off under reduced pressure. The residue was dissolved in 50 ml of 70% aqueous acetonitrile, and to the solution was added 4.8 g (38.2 mmol) of oxalic acid dehydrate. The mixture was dissolved under heating, and then cooled. The resulting crystals were recrystallized from 70% aqueous acetonitrile to obtain 8.1 g of colorless crystals having a melting point of 105 to 107° C.

$^1$H-NMR(CDCl$_3$) δ: 0.88(3H,t,J=7 Hz,CH$_3$), 1.0-1.6(18H, m), 1.40(6H,s,(CH$_3$)$_2$C), 3.29(2H,br dt-like,NHC$\underline{H}_2$), 4.54 (2H,d,J=5 Hz,ArCH$_2$), 7.0-7.4(6H,m,ArH,NH), 7.86(1H,br t-like), 8.41,8.56(each 1H,br s).

Working Example 52

3,6-Dihydro-6,6-dimethyl-4-octylamino-2-benzylamino-1,3,5-triazine acetate 100 ml of methanol, 100 ml of acetone and 0.4 ml of concentrated hydrochloric acid were added to 5.0 g (13.3 mmol) of N$^1$-benzyl-N$^5$-octyl-biguanide dihydrochloride. The mixture was refluxed for 22 hours, and the solvent was distilled off under reduced pressure. The residue was dissolved in 100 ml of ethanol, and to the solution were added 80 ml of water and 5.8 ml of 5N aqueous sodium hydroxide. The mixture was refluxed for 1.5 hours, concentrated under reduced pressure, and extracted with ethyl acetate. The extract was washed with water, and the solvent was distilled off under reduced pressure, and a portion (2.8 g) of 5.8 g of the resulting crystals were recrystallized from ether to obtain 1.1 g of colorless crystals having a melting point of 88 to 91° C.

$^1$H-NMR(CDCl$_3$)δ: 0.87(3H,t,J=7 Hz,CH$_3$), 1.1-1.4(10H, m), 1.31(6H,s,(CH$_3$)$_2$C), 1.45(2H,m,NHCH$_2$C$\underline{H}_2$), 1.92(3H, s,C$\underline{H}_3$COOH), 3.22(2H,m,NHC$\underline{H}_2$CH$_2$), 4.47(2H,m, ArCH$_2$), 7.1-7.3(5H,m,ArH), 8.13,8.64(each 1H,m,NH), 9.07,9.23(each 1H,br s,NH,NH$^+$).

Working Example 53

3,6-Dihydro-6,6-diethyl-4-heptylamino-2-benzylamino-1,3,5-triazine hydrochloride 100 ml of methanol, 150 ml of 3-pentanone, and 0.5 ml of concentrated hydrochloric acid were added to 6.0 g (15.6 mmol) of N$^1$-benzyl-N$^5$-heptyl-biguanide dihydrochloride. The mixture was refluxed for 24 hours, and the solvent was distilled off under reduced pressure. The residue was dissolved in 100 ml of methanol, and to the solution were added 80 ml of water and 5 ml of 5N aqueous sodium hydroxide. The mixture was refluxed for 1.5 hours, concentrated under reduced pressure and extracted with ethyl acetate. The extract was washed with water, and acidified with 6N hydrochloric acid, and concentrated under reduced pressure to remove the solvent. The residue was purified by silica gel column chromatography (elution with a mixture of chloroform and methanol (9:1)) to obtain 4.7 g of a pale yellow resinous solid.

$^1$H-NMR(CDCl$_3$)δ: 0.86(3H,t,J=7 Hz,CH$_3$), 0.91(6H,t, J=7 Hz,CH$_2$C$\underline{H}_3$×2), 1.1-1.6(10H,m), 1.63(4H,q,J=7 Hz, C$\underline{H}_2$CH$_3$×2), 3.24(2H,br dt-like,NHC$\underline{H}_2$),4.51(2H,d,J=6 Hz,ArCH$_2$), 7.21(1H,br t-like,NH), 7.1-7.4(5H,m,ArH), 7.60 (1H,br t-like,NH), 8.21,8.38(each 1H,br s,NH,NH$^+$).

Working Example 54

3,6-Dihydro-6-spirocyclopentane-4-heptylamino-2-benzylamino-1,3,5-triazine acetate 15.0 g (0.178 mol) of cyclopentanone, 80 ml of methanol, and 0.9 ml of concentrated hydrochloric acid were added to 8.0 g (22.1 mmol) of N$^1$-benzyl-N$^5$-heptyl-biguanide dihydrochloride. The mixture was refluxed for 48 hours, and the solvent was distilled off under reduced pressure. The residue was dissolved in 100 ml of methanol, and to the solution were added 20 ml of water and 14 ml of 5N aqueous sodium hydroxide. The mixture was concentrated under reduced pressure, and extracted with ethyl acetate. The extract was washed with water, and the solvent was distilled off under reduced pressure. Half amount of the residue was taken, and recrystallized two times from ethanol/ether to obtain 2.8 g of colorless crystals having a melting point of 100 to 102° C.

$^1$H-NMR(CDCl$_3$) δ: 0.86(3H,t,J=7 Hz,CH$_3$), 1.1-1.5(10H, m), 1.5-1.9(8H,m), 1.91(3H,s,C$\underline{H}_3$COOH), 3.18(2H,br dt-like,NHC$\underline{H}_2$), 4.45(2H,d,J=6 H$\overline{z}$,ArCH$_2$), 7.1-7.3(5H,m, ArH), 8.41,8.90(each 1H,br t-like,NH), 9.11,9.22(each 1H,br s,NH,NH$^+$).

Working Example 55

3,6-Dihydro-6,6-dimethyl-4-decylamino-2-phenethylamino-1,3,5-triazine malonate 200 ml of methanol, 150 ml of acetone, and 0.7 ml of concentrated hydrochloric acid were added to 12.0 g (28.7 mmol) of N$^1$-phenethyl-N$^5$-decyl-biguanide dihydrochloride. The mixture was refluxed for 17 hours, and the solvent was distilled off under reduced pressure. The residue was dissolved in 150 ml of ethanol, and to the solution were added 120 ml of water and 12.6 ml of 5N aqueous sodium hydroxide. The mixture was refluxed for 1.5 hours, concentrated under reduced pressure, and extracted with ethyl acetate. The extract was washed with water, and the solvent was distilled off under reduced pressure to obtain 12.5 g of a solid. Then, 5.9 g of the solid was dissolved in 50 ml of 70% aqueous acetonitrile, and to the solution was added 163 g (15.7 mmol) of malonic acid. The mixture was dissolved under heating, and then cooled. The resulting crystals were recrystallized from 70% aqueous acetonitrile to obtain 1.7 g of colorless crystals having a melting point of 105 to 106° C.

$^1$H-NMR(CDCl$_3$) δ: 0.87(3H,t,J=6 Hz,CH$_3$), 1.1-1.7(16H, m), 1.44(6H,s,(CH$_3$)$_2$C), 2.88(2H,t,J=7 Hz,ArC$\underline{H}_2$CH$_2$NH), 3.18(2H,s,HOOCC$\underline{H}_2$COO$^-$), 3.35(2H,br dt-like,NHC$\underline{H}_2$), 3.59(2H,br dt-like,ArCH$_2$C$\underline{H}_2$NH), 7.1-7.3(5H,m,ArH), 7.65,7.75(each 1H,m), 8.37(2H,m).

Working Example 56

3,6-Dihydro-6,6-dimethyl-4-nonylamino-2-phenethylamino-1,3,5-triazine acetate 350 ml of methanol, 350 ml of acetone and 1.9 ml of concentrated hydrochloric acid were added to 31.0 g (76.7 mmol) of N$^1$-phenethyl-N$^5$-nonyl-biguanide dihydrochloride. The mixture was refluxed for 16 hours, and the solvent was distilled off under reduced pressure. The residue was dissolved in 350 ml of ethanol, and to the solution were added 250 ml of water and 31 ml of 5N sodium hydroxide. The mixture was refluxed for 1.5 hours, concentrated under reduced pressure, and extracted with ethyl acetate. The extract was washed with water, and the solvent was distilled off under reduced pressure. The residue was recrystallized from ether to obtain 16.3 g of colorless crystals having a melting point of 72 to 76° C.

$^1$H-NMR(CDCl$_3$)δ: 0.86(3H,t,J=7 Hz,CH$_3$), 1.1-1.4(12H, m), 1.34(6H,s,(CH$_3$)$_2$C), 1.54(2H,m,NHCH$_2$CH$_2$), 1.93(3H, s,CH$_3$COO$^-$), 2.84(2H,t,J=6 Hz,ArCH$_2$CH$_2$NH), 3.31(2H,br dt-like,NHCH$_2$CH$_2$), 3.53(2H,br dt-like,ArCH$_2$CH$_2$NH), 7.1-7.3(5H,m,ArH), 8.15,8.29(each 1H,m,NH), 9.12,9.23(each 1H,br s,NH,NH$^+$).

Working Example 57

4-Octylamino-3,6-dihydro-6,6-dimethyl-2-phenethylamino-1,3,5-triazine acetate 150 ml of methanol, 150 ml of acetone and 0.8 ml of concentrated hydrochloric acid were added to 13.1 g (33.6 mmol) of N$^1$-phenethyl-N$^5$-octyl-biguanide dihydrochloride. The mixture was refluxed for 24 hours, and the solvent was distilled off under reduced pressure. The residue was dissolved in 150 ml of ethanol, and to the solution were added 100 ml of water and 13 ml of 5N aqueous sodium hydroxide. The mixture was refluxed for 1.5 hours, concentrated under reduced pressure, and extracted with ethyl acetate. The extract was washed with water, and the solvent was distilled off under reduced pressure. The residue was recrystallized two times from ethanol/ether to obtain 4.8 g of colorless crystals having a melting point of 86 to 88° C.

$^1$H-NMR(CDCl$_3$) δ: 0.86(3H,t,J=7 Hz,CH$_3$), 1.1-1.5(10H, m), 1.34(6H,s,(CH$_3$)$_2$C), 1.54(2H,m,NHCH$_2$CH$_2$), 1.94(3H, s,CH$_3$COO$^-$), 2.84(2H,t,J=7 Hz,ArCH$_2$CH$_2$NH), 3.31(2H,br dt-like,NHCH$_2$CH$_2$), 3.53(2H,br dt-like,ArCH$_2$CH$_2$NH), 7.1-7.3(5H,m,ArH), 8.15,8.30(each 1H,m,NH), 9.11,9.22(each 1H,br s,NH,NH$^+$).

Working Example 58

4-Octylamino-3,6-dihydro-6,6-dimethyl-2-(4'-methylbenzylamino)-1,3,5-triazine acetate 300 ml of methanol, 180 ml of acetone and 1.2 ml of concentrated hydrochloric acid were added to 18.0 g (46.1 mmol) of N$^1$-4-methylbenzyl-N$^5$-octyl-biguanide dihydrochloride. The mixture was refluxed for 24 hours, and the solvent was distilled off under reduced pressure. The residue was dissolved in 200 ml of ethanol, and to the solution were added 140 ml of water and 18.5 ml of 5N aqueous sodium hydroxide. The mixture was refluxed for 1.5 hours, concentrated under reduced pressure, and extracted with ethyl acetate. The extract was washed with water, and the solvent was distilled off under reduced pressure. The residue was dissolved in ether, and cooled. The resulting precipitated crystals were filtered off, and recrystallized from ethanol/ether to obtain 10.1 g of colorless crystals having a melting point of 101 to 102° C.

$^1$H-NMR(CDCl$_3$) δ: 0.87(3H,t,J=7 Hz,CH$_3$), 1.1-1.4(10H, m), 1.30(6H,s,(CH$_3$)$_2$C), 1.46(2H,m,NHCH$_2$CH$_2$), 1.91(3H, s,CH$_3$COO$^-$), 2.30(3H,s,ArCH$_3$), 3.25(2H,br dt-like,NHCH$_2$CH$_2$), 4.43(2H,d,J=5 Hz,ArCH$_2$), 7.07(2H,d,J=8 Hz,ArH), 7.15(2H,d,J=8 Hz,ArH), 8.18,8.60(each 1H,m,NH), 9.12,9.22(each 1H,m,NH,NH$^+$).

Working Example 59

3,6-Dihydro-6,6-dimethyl-4-heptylamino-2-(4'-methylbenzylamino)-1,3,5-triazine acetate 140 ml of methanol, 60 ml of acetone and 0.7 ml of concentrated hydrochloric acid were added to 10.0 g (26.6 mmol) of N$^1$-4-methylbenzyl-N$^5$-heptyl-biguanide dihydrochloride. The mixture was refluxed for 24 hours, and the solvent was distilled off under reduced pressure. The residue was dissolved in 100 ml of ethanol, and to the solution were added 60 ml of water and 10.8 ml of 5N aqueous sodium hydroxide. The mixture was refluxed for 1 hour, concentrated under reduced pressure, and extracted with ethyl acetate. The extract was washed with 10% aqueous sodium acetate solution, and washed with water. The solvent was distilled off under reduced pressure, and the residue was recrystallized from methyl ethyl ketone to obtain 7.2 g of colorless crystals having a melting point of 102 to 104° C.

$^1$H-NMR(CDCl$_3$) δ: 0.87(3H,t,J=7 Hz,CH$_3$), 1.1-1.4(8H, m), 1.30(6H,s,(CH$_3$)$_2$C), 1.46(2H,m,NHCH$_2$CH$_2$), 1.91(3H, s,CH$_3$COO$^-$), 2.30(3H,s,ArCH$_3$), 3.24(2H,br dt-like,NHCH$_2$CH$_2$), 4.43(2H,d,J=3 Hz,ArCH$_2$), 7.07(2H,d,J=8 Hz,ArH), 7.15(2H,d,J=8 Hz,ArH), 8.17,8.59(each 1H,m,NH), 9.10,9.21(each 1H,br s,NH,NH$^+$).

Working Example 60

3,6-Dihydro-6,6-dimethyl-4-decylamino-2-(4'-hydroxycarbonylbenzylamino)-1,3,5-triazine hydrochloride 50 ml of methanol, 100 ml of acetone and 1.6 ml of piperidine were added to 5.0 g (10.8 mmol) of N$^1$-(4-methoxycarbonylbenzyl)-N$^5$-decyl-biguanide dihydrochloride. The mixture was refluxed for 24 hours, and the solvent was distilled off under reduced pressure. The residue was purified by silica gel column chromatography (elution with a mixture of chloroform/methanol/acetic acid (8:0.7:0.7→8:1:1)). 4.0 g of the purified product was dissolved in 60 ml of ethanol, and to the solution were added 60 ml of water and 2.4 ml of 5N aqueous sodium hydroxide. The mixture was refluxed for 2 hours, and 5 ml of concentrated hydrochloric acid was added thereto. The mixture was concentrated under reduced pressure, and extracted with chloroform. The aqueous layer was separated, and the solvent was distilled off under reduced pressure. The residue was dried well under reduced pressure, heated and extracted with methanol. The extract was filtered, and cooled. The resulting precipitates were filtered, and the solvent of the filtrate was distilled off under reduced pressure. The residue was extracted with ethanol under heating, and filtered. The solvent of the filtrate was distilled off under reduced pressure, and ether was added to the residue to obtain 3.4 g of a white yellow solid.

$^1$H-NMR(CDCl$_3$) δ: 0.87(3H,t,J=7 Hz,CH$_3$), 1.1-1.6(16H, m), 1.49(6H,s,(CH$_3$)$_2$C), 3.25(2H,br dt-like,NHCH$_2$), 4.59 (2H,d,J=6 Hz,ArCH$_2$), 7.16(1H,m,NH), 7.36(2H,d,J=8 Hz,ArH), 7.74(1H,m,NH), 7.99(2H,d,J=8 Hz,ArH), 8.33,8.45(each 1H,br s,NH,NH$^+$).

Working Example 61

2-Amino-1,6-dihydro-6,6-dimethyl-4-nonylamino-1-phenyl-1,3,5-triazine hydrochloride 100 ml of methanol, 80 ml of acetone and 0.6 ml of concentrated hydrochloric acid were added to 9.0 g (23.9 mmol) of $N^1$-phenyl-$N^5$-nonyl-biguanide dihydrochloride. The mixture was refluxed for 24 hours, and the solvent was distilled off under reduced pressure. The residue was recrystallized from methyl ethyl ketone to obtain 3.8 g of colorless crystals having a melting of 134 to 137° C.

$^1$H-NMR(CDCl$_3$) δ: 0.88(3H,t,J=7 Hz,CH$_3$), 1.0-1.5(12H, m), 1.52(6H,m,(CH$_3$)$_2$C), 1.61(2H,m,NHCH$_2$C$\underline{H}_2$), 3.36(2H,br dt-like,NHC$\underline{H}_2$CH$_2$), 4.2-6.0(2H,br,NH$_2$), 7.26-7.31(2H,m,ArH), 7.53-7.58(3H,m,ArH), 8.10(1H,br t-like, NH), 10.00(1H, br s,NH$^+$).

Working Example 62

3,6-Dihydro-6,6-dimethyl-4-nonylamino-2-phenylamino-1,3,5-triazine acetate

The recrystallization mother liquid of Working Example 61 was taken, and the solvent was distilled off under reduced pressure. The residue was dissolved in 70 ml of ethanol, and to the solution were added 45 ml of water and 6.8 ml of 5N aqueous sodium hydroxide. The mixture was refluxed for 1 hour, concentrated under reduced pressure, and extracted with ethyl acetate. The extract was washed with 10% aqueous sodium acetate solution, and washed with water. The solvent was distilled off under reduced pressure, and the residue was recrystallized from methyl ethyl ketone to obtain 4.4 g of colorless crystals having a melting point of 113 to 116° C.

$^1$H-NMR(CDCl$_3$) δ: 0.87(3H,t,J=7 Hz,CH$_3$), 1.1-1.7(14H, m), 1.46(6H,s,(CH$_3$)$_2$C), 2.03(3H,s,CH$_3$COO$^-$), 3.32(2H,br dt-like,NHC$\underline{H}_2$), 7.0-7.6(5H,m,ArH), 7.85,9.03,9.37(each 1H,m,NH×2,NH$^+$).

Working Example 63

2-Amino-4-octylamino-1,6-dihydro-6,6-dimethyl-1-(1'-naphthyl)-1,3,5-triazine hydrochloride 50 ml of methanol, 50 ml of acetone and 0.2 ml of concentrated hydrochloric acid were added to 2.6 g (6.3 mmol) of $N^1$-(1-naphthyl)-$N^5$-octyl-biguanide dihydrochloride. The mixture was refluxed for 24 hours, and the solvent was distilled off under reduced pressure. The residue was purified by silica gel column chromatography (elution with a mixture of chloroform and methanol (9:1)) to obtain 1.7 g of a pale yellow solid.

$^1$H-NMR(CDCl$_3$) δ: 0.88(3H,t,J=7 Hz,CH$_3$), 1.1-1.8(18H, m,(CH$_2$)$_6$, (CH$_3$)$_2$C), 3.39(2H,br dt-like,NHC$\underline{H}_2$), 4.2-5.8 (2H,br,NH$_2$), 7.4-8.1(7H,m,ArH), 8.23(1H,br t-like,NH), 10.01(1H,brs,NH$^+$).

Working Example 64

4-Octylamino-3,6-dihydro-6,6-dimethyl-2-(1'-naphthylamino)-1,3,5-triazine 1.6 g of the pale yellow solid of Working Example 63 was dissolved in 50 ml of ethanol, and to the solution were added 30 ml of water and 1.7 ml of 5N aqueous sodium hydroxide. The mixture was refluxed for 1.5 hours, concentrated under reduced pressure, and extracted with ether. The extract was washed with water, concentrated, and cooled to obtain 1.1 g of colorless crystals having a melting point of 157 to 159° C.

$^1$H-NMR(CD$_3$OD) δ: 0.90(3H,t,J=7 Hz,CH$_3$), 1.2-1.6 (12H,m), 1.37(6H,s,(CH$_3$)$_2$C), 3.15(2H,t,J=7 Hz,NHC$\underline{H}_2$), 7.36-8.06(7H,m,ArH).

Working Example 65

4-Octylamino-2-cyclohexylmethylamino-3,6-dihydro-6,6-dimethyl-1,3,5-triazine acetate 100 ml of methanol, 80 ml of acetone and 0.6 ml of concentrated hydrochloric acid were added to 9.0 g (23.5 mmol) of $N^1$-cyclohexylmethyl-$N^5$-octyl-biguanide dihydrochloride. The mixture was refluxed for 21 hours, and the solvent was distilled off under reduced pressure. To the residue were added 120 ml of ethanol, 80 ml of water, and 9.5 ml of 5N sodium hydroxide, and the mixture was refluxed for 1 hour, concentrated under reduced pressure, and extracted with methyl ethyl ketone. The extract was washed with water, and 1.7 g of acetic acid was added thereto. The solvent was distilled of f under reduced pressure, and the residue was dried well, and recrystallized from methyl ethyl ketone two times to obtain 4.9 g of colorless crystals having a melting point of 70 to 73° C.

$^1$H-NMR(CDCl$_3$) δ: 0.88(3H,t,J=7 Hz,CH$_3$), 0.8-1.8(23H, m,cyclohexyl, (CH$_2$)$_6$), 1.36(6H,s,(CH$_3$)$_2$C), 1.97(3H,s, CH$_3$COO$^-$), 3.16,3.27(each 2H,m,NHC$\underline{H}_2$×2), 8.15(2H,m, NH×2), 9.13(2H,br s,NH,NH$^+$).

Working Example 66

2,4-Dioctylamino-3,6-dihydro-6,6-dimethyl-1,3,5-triazine acetate 100 ml of methanol, 80 ml of acetone and 0.6 ml of concentrated hydrochloric acid were added to 10.0 g (25.1 mmol) of $N^1$,$N^5$-dioctyl-biguanide dihydrochloride. The mixture was refluxed for 64 hours, and the solvent was distilled off under reduced pressure. To the residue were added 110 ml of ethanol, 60 ml of water and 10.1 ml of 5N sodium hydroxide, and the mixture was refluxed for 1 hour, concentrated under reduced pressure, and then extracted with ethyl acetate. The extract was washed with water, and the solvent was distilled off under reduced pressure. The residue was recrystallized from methyl ethyl ketone to obtain 7.2 g of colorless crystals having a melting point of 91 to 93° C.

$^1$H-NMR(CDCl$_3$) δ: 0.88(6H,t,J=7 Hz, CH$_3$×2), 1.0-1.4 (20H,m), 1.36(6H,s,(CH$_3$)$_2$C), 1.53(4H,m,NHCH$_2$C$\underline{H}_2$×2), 1.97(3H,s,CH$_3$COO$^-$), 3.29(4H,br dt-like,NHC$\underline{H}_2$CH$_2$×2), 8.09(2H,m,NH×2), 9.10(2H,br s,NH,NH$^+$).

Working Example 67

4-Octylamino-3,6-dihydro-6,6-dimethyl-2-heptylamino-1,3,5-triazine acetate 100 ml of methanol, 80 ml of acetone and 0.5 ml of concentrated hydrochloric acid were added to 8.0 g (20.8 mmol) of $N^1$-octyl-$N^5$-heptyl-biguanide dihydrochloride. The mixture was refluxed for 64 hours, and the solvent was distilled off under reduced pressure. To the residue were added 100 ml of ethanol, 60 ml of water and 8.5 ml of 5N sodium hydroxide, and the mixture was refluxed for 1 hour, concentrated under reduced pressure, and extracted with ethyl acetate. The extract was washed with water, and 1.3 g of acetic acid was added thereto. The solvent was distilled off under reduced pressure, and the residue was dried well, and recrystallized from methyl ethyl ketone to obtain 4.1 g of colorless crystals having a melting point of 82 to 84° C.

$^1$H-NMR(CDCl$_3$) δ: 0.88(6H,t,J=7 Hz,CH$_3$×2), 1.1-1.5 (18H,m), 1.36(6H,s,(CH$_3$)$_2$C), 1.53(4H,m,NHCH$_2$C$\underline{H}_2$×2), 1.97(3H,s,CH$_3$COO$^-$), 3.29(4H,br dt-like,NHC$\underline{H}_2$CH$_2$×2), 8.12(2H,m,NH×2), 9.11(2H,br s,NH,NH$^+$).

Working Example 68

4-Octylamino-3,6-dihydro-6,6-dimethyl-2-hexylamino-1,3,5-triazine acetate 120 ml of methanol, 100 ml of acetone and 0.7 ml of concentrated hydrochloric acid were added to 10.0 g (27.0 mmol) of N$^1$-octyl-N5-hexyl-biguanide dihydrochloride. The mixture was refluxed for 40 hours, and the solvent was distilled off under reduced pressure. To half amount of the residue were added 70 ml of ethanol, 46 ml of water and 6 ml of 5N sodium hydroxide, and the mixture was refluxed for 1 hour, concentrated under reduced pressure, and extracted with ethyl acetate. The extract was washed with water, and the solvent was distilled off under reduced pressure. The residue was recrystallized from methyl ethyl ketone to obtain 3.7 g of colorless crystals having a melting point of 92 to 94° C.

$^1$H-NMR(CDCl$_3$) δ: 0.88(6H,t,J=7 Hz,CH$_3$×2), 1.1-1.5 (16H,m), 1.36(6H,s,(CH$_3$)$_2$C), 1.52(4H,m,NHCH$_2$C$\underline{H}_2$×2), 1.96(3H,s,CH$_3$COO$^-$), 3.28(4H,br dt-like,NHC$\underline{H}_2$CH$_2$×2), 8.11(2H,m,NH×2), 9.10(2H,br s,NH,NH$^+$).

Working Example 69

2,4-Diheptylamino-3,6-dihydro-6,6-dimethyl-1,3,5-triazine acetate 100 ml of methanol, 80 ml of acetone and 0.7 ml of concentrated hydrochloric acid were added to 10.0 g (27.0 mmol) of N$^1$,N$^5$-diheptyl-biguanide dihydrochloride, and the mixture was refluxed for 24 hours. The solvent was distilled off under reduced pressure. To the residue were added 100 ml of ethanol, 60 ml of water, and 10.9 ml of 5N sodium hydroxide, and the mixture was refluxed for 1 hour, concentrated under reduced pressure, and extracted with ethyl acetate. The extract was washed with 10% aqueous sodium acetate, washed with water, and concentrated under reduced pressure to remove the solvent. The residue was recrystallized from methyl ethyl ketone to obtain 7.3 g of colorless crystals having a melting point of 83 to 85° C.

$^1$H-NMR(CDCl$_3$) δ: 0.88(6H,t,J=7 Hz,CH$_3$×2), 1.0-1.4 (16H,m), 1.36(6H,s,(CH$_3$)$_2$C), 1.53(4H,m,NHCH$_2$C$\underline{H}_2$×2), 1.97(3H,s,CH$_3$COO$^-$), 3.29(4H,m,NHC$\underline{H}_2$CH$_2$×2), 8.12 (2H,m,NH×2), 9.11(2H,m,NH,NH$^+$).

Working Example 70

3,6-Dihydro-6,6-dimethyl-2-hexylamino-4-heptylamino-1,3,5-triazine acetate 100 ml of methanol, 80 ml of acetone and 0.7 ml of concentrated hydrochloric acid were added to 10.0 g (28.1 mmol) of N$^1$-hexyl-N$^5$-heptyl-biguanide dihydrochloride. The mixture was refluxed for 23 hours, and the solvent was distilled off under reduced pressure. To the residue were added 100 ml of ethanol, 60 ml of water and 11.3 ml of 5N sodium hydroxide, and the mixture was refluxed for 1 hour, concentrated under reduced pressure, and extracted with ethyl acetate. The extract was washed successively with 10% aqueous sodium acetate and water, and the solvent was distilled off under reduced pressure. The residue was recrystallized from methyl ethyl ketone to obtain 8.4 g of colorless crystals having a melting point of 70 to 75° C.

$^1$H-NMR(CDCl$_3$) δ: 0.88(6H,t,J=7 Hz,CH$_3$×2), 1.2-1.7 (18H,m), 1.36(6H,s,(CH$_3$)$_2$C), 1.97(3H,s,CH$_3$COO$^-$), 3.29 (4H,br dt-like,NHC$\underline{H}_2$×2), 8.10(2H,m,NH×2), 9.10(2H,br s,NH,NH$^+$).

Working Example 71

3,6-Dihydro-6,6-dimethyl-4-heptylamino-2-(1',1',3',3'-tetramethylbutylamino)-1,3,5-triazine acetate 100 ml of methanol, 80 ml of acetone and 2.9 ml of concentrated hydrochloric acid were added to 9.0 g (25.9 mmol) of N$^1$-heptyl-N$^5$- (1,1,3,3-tetramethylbutyl)-biguanide hydrochloride. The mixture was refluxed for 21 hours, and the solvent was distilled off under reduced pressure. To the residue were added 100 ml of ethanol, 60 ml of water and 10.6 ml of 5N sodium hydroxide, and the mixture was refluxed for 1 hour, concentrated under reduced pressure, and extracted with ethyl acetate. The extract was washed successively with 10% aqueous sodium acetate and water, and the solvent was distilled off under reduced pressure. The residue was recrystallized from methyl ethyl ketone two times to obtain 8.3 g of colorless crystals having a melting point of 98 to 101° C.

$^1$H-NMR(CDCl$_3$) δ: 0.87(3H,t,J=7 Hz,CH$_3$), 0.98(9H,s, (CH$_3$)$_3$C), 1.1-1.6(10H,m), 1.38,1.42(each6H,s,(CH$_3$)$_2$C× 2), 1.89(2H,s,CH$_2$), 1.97(3H,s,CH$_3$COO$^-$),3.29(2H,br dt-like,NHC$\underline{H}_2$),7.33(1H,br s,NH), 8.09(1H,m,NH), 8.81,9.09(each H,m,NH,NH$^+$).

Working Example 72

2-Amino-3,6-dihydro-6,6-dimethyl-4-tetradecylamino-1,3,5-triazine hydrochloride 150 ml of n-propanol was added to 27 g (0.108 mol) of 1-aminotetradecane hydrochloride and 9.5 g (0.113 mol) of dicyanodiamide, and the mixture was refluxed for 64 hours. The precipitated crystals (1-aminotetradecane hydrochloride) formed upon cooling were filtered off, and the filtrate was concentrated, and cooled to obtain colorless crystals (crude N$^1$-tetradecyl-biguanide hydrochloride). Then, to 10.0 g (30.0 mmol) of the crystals were added 100 ml of methanol, 80 ml of acetone and 3.0 ml of concentrated hydrochloric acid, and the mixture was refluxed for 20 hours. The solvent was distilled off under reduced pressure, and the residue was purified by silica gel column chromatography (elution with a mixture of chloroform/methanol/acetic acid (8:1:1→8:1:2)), and recrystallized from methyl ethyl ketone to obtain 1.2 g of colorless crystals having a melting point of 186 to 187° C.

$^1$H-NMR(DMSO-d$_6$) δ: 0.86(3H,t,J=7 Hz,CH$_3$), 1.2-1.6 (22H,m), 1.43(6H,s,(CH$_3$)$_2$C), 3.25(2H,br t-like,NHC$\underline{H}_2$), 7.02,7.41(each 2H,m), 8.68(1H,m).

Working Example 73

2-Ethylamino-3,6-dihydro-6,6-dimethyl-4-dodecylamino-1,3,5-triazine acetate 100 ml of methanol, 80ml of acetone and 2.6 ml of concentrated hydrochloric acid were added to 8.0 g (24.0 mmol) of N$^1$-ethyl-N$^5$-dodecyl-biguanide hydrochloride, and the mixture was refluxed for 64 hours. The solvent was distilled off under reduced pressure. To the residue were added 100 ml of ethanol, 60 ml of water and 12.0 ml of 5N sodium hydroxide, and the mixture was refluxed for 1 hour, concentrated under reduced pressure, and extracted with ethyl acetate. The extract was washed successively with 10% aqueous sodium acetate and water, and the solvent was distilled off under reduced pressure. The residue was recrystallized from methyl ethyl ketone to obtain 6.2 g of colorless crystals having a melting point of 79 to 82° C.

$^1$H-NMR(CDCl$_3$) δ: 0.88(3H,t,J=7 Hz,CH$_3$), 1.16(3H,t, J=7 Hz,NHCH$_2$CH$_3$), 1.1-1.4(18H,m), 1.37(6H,s,(CH$_3$)$_2$C), 1.53(2H,m,NHCH$_2$CH$_2$), 1.97(3H,s,CH$_3$COO$^-$), 3.31(4H, m,NHCH$_2$CH$_2$,NHCH$_2$CH$_3$), 8.13(2H,m,NH×2), 9.12(2H, m,NH,NH$^+$).

Working Example 74

3,6-Dihydro-2,4-dioctylamino-1,3,5-triazine acetate 200 ml of butanol, 13 ml (0.15 mol) of methylal and 1.2 ml of concentrated hydrochloric acid were added to 5.8 g (14.6 mmol) of N$^1$,N$^5$-dioctyl-biguanide dihydrochloride, and the mixture was refluxed for 28 hours. The solvent was distilled off under reduced pressure. To the residue were added 50 ml of ethanol, 30 ml of water, and 5.9 ml of 5N sodium hydroxide, and the mixture was refluxed for 1 hour, concentrated under reduced pressure, and extracted with ethyl acetate. The extract was washed successively with 10% aqueous sodium acetate andwater, and the solvent was distilled off under reduced pressure. The residue was recrystallized from methyl ethyl ketone to obtain 2.1 g of colorless crystals having a melting point of 117 to 121° C.

$^1$H-NMR(CDCl$_3$) δ: 0.88(6H,t,J=7Hz,CH$_3$×2), 1.1-1.4 (20H,m), 1.54(4H,m,NHCH$_2$CH$_2$×2), 1.97(3H,s, CH$_3$COO$^-$), 3.30(4H,br t-like,NHCH$_2$CH$_2$×2), 4.37(2H,s, CH$_2$), 7.28(1H,m,NH), 8.22(2H,m,NH×2).

Working Example 75

2-Amino-3,6-dihydro-6,6-dimethyl-4-dodecylamino-1,3,5-triazine.nitrate 17.0 g (76.6 mmol) of 1-aminododecane and 6.5 g (77.3 mmol) of dicyanodiamide were stirred and heated in an oil bath at 185 to 190° C. for 40 minutes. The mixture was dissolved in 200 ml of ethanol, and to the solution were added 100 ml of acetone and 7.7 ml of concentrated hydrochloric acid. The solution was refluxed for 20 hours, and the solvent was distilled off under reduced pressure. The residue was purified by silica gel column chromatography (elution with a mixture of chloroform and methanol (8:2)). 20 g of the purified product was dissolved in a mixture of ethyl acetate and methanol, and to the solution were added 15 ml of 5N sodium hydroxide and water. The mixture was stirred well, and the ethyl acetate layer was washed with 10% aqueous sodium acetate solution. The solvent was distilled off under reduced pressure, and the residue was dissolved in 100 ml of methanol, and to the solution was added 3.0 ml of concentrated nitric acid under ice-cooling. The solvent was distilled off under reduced pressure, and the residue was purified by silica gel column chromatography (elution with a mixture of chloroform/methanol/acetic acid (8:1:1→8:1:2)) to obtain 6.2 g of a pale yellow resinous solid.

$^1$H-NMR(DMSO-d$_6$) δ: 0.86(3H,t,J=7 Hz,CH$_3$), 1.1-1.6 (20H,m), 1.39(6H,s,(CH$_3$)$_2$C), 3.0-3.3(2H,m,NHCH$_2$), 7.10, 8.01(each 2H,m), 8.35(1H,m).

Working Example 76

4-Octylamino-3,6-dihydro-6,6-dimethyl-2-hexylamino-1,3,5-triazine gluconate 70 ml of ethanol, 35 ml of water and 5 ml of 5N sodium hydroxide were added to 5.4 g of the residue in Working Example 68, and the mixture was refluxed for 1 hour, concentrated under reduced pressure, and extracted with ether. The extract was washed with water, and the solvent was distilled off under reduced pressure. The residue was dissolved in acetone, and 5.4 g (13.8 mmol) of 50% gluconic acid solution was added thereto. The resulting precipitated crystals were recrystallized from a mixture of methyl ethyl ketone and ethanol (8:2) to obtain 3.6 g of colorless crystals having a melting point of 103 to 105° C.

$^1$H-NMR(CD$_3$OD) δ: 0.80-0.95(6H,m,CH$_3$×2), 1.1-1.7 (20H,m), 1.46(6H,s,(CH$_3$)$_2$C), 3.1-3.4(4H,m,NHCH$_2$×2), 3.5-4.1(6H,m,gluconic acid).

Working Example 77

4-Octylamino-3,6-dihydro-6,6-dimethyl-2-(4'-methylbenzylamino)-1,3,5-triazine gluconate 100 ml of ether, 30 ml of water and 1.7 ml of 5N sodium hydroxide were added to 3.0 g (7.2 mmol) of the compound of Working Example 58. The mixture was stirred, washed with water, and concentrated under reduced pressure to remove the solvent. The residue was dissolved in 20 mol of acetone, and to the solution was added 3.1 g (7.9 mmol) of 50% gluconic acid solution. The resulting precipitated crystals were recrystallized from a mixture of methyl ethyl ketone and ethanol mixed solution (8:2) to obtain 2.0 g of colorless crystals having a melting point of 122 to 124° C.

$^1$H-NMR(DMSO-d$_6$-D$_2$O) δ: 0.85(3H,t,J=7 Hz,CH$_3$), 1.1-1.5(12H,m), 1.37(6H,s,(CH$_3$)$_2$C), 2.27(3H,s,ArCH$_3$), 3.0-3.9(6H,m,gluconic acid), 3.20(2H, br t-like,NHCH$_2$), 4.41 (2H,s,ArCH$_2$), 7.12,7.17(each 2H,d,J=8 Hz,ArH).

Working Example 78

3,6-Dihydro-6,6-dimethyl-4-nonylamino-2-benzylamino-1,3,5-triazine gluconate 100 ml of ether, 30 ml of water and 1.7 ml of 5N sodium hydroxide were added to 3.2 g (7.6 mmol) of the compound of Working Example 48, and the mixture was stirred, washed with water, and concentrated under reduced pressure to remove the solvent. The residue was dissolved in 20 ml of acetone, and to the solution was added 3.1 g (7.9 mmol) of 50% gluconic acid solution. The resulting precipitated crystals were recrystallized from a mixture of methyl ethyl ketone and ethanol (8:2) to obtain 3.4 g of colorless crystals having a melting point of 102 to 104° C.

$^1$H-NMR(DMSO-d$_6$-D$_2$O) δ: 0.85(3H,t,J=7 Hz,CH$_3$), 1.1-1.5(14H,m), 1.38(6H,s,(CH$_3$)$_2$C), 3.0-3.9(6H,m,gluconic acid), 3.19(2H,br t-like,NHCH$_2$), 4.46(2H,s,ArCH$_2$), 7.2-7.4 (5H,m,ArH).

Working Example 79

3,6-Dihydro-6,6-dimethyl-4-dodecylamino-2-furfurylamino-1,3,5-triazine acetate 150 ml of methanol, 120 ml of acetone and 0.6 ml of concentrated hydrochloric acid were added to 10.0 g (23.7 mmol) of $N^1$-furfuryl-$N^5$-dodecyl-biguanide dihydrochloride. The mixture was refluxed for 22 hours, and the solvent was distilled off under reduced pressure. The residue was dissolved in ethyl acetate, and to the solution was added 11 ml of 5N sodium hydroxide. The mixture was stirred, washed with 10% aqueous sodium acetate, and concentrated under reduced pressure to remove the solvent. The residue was purified by silica gel column chromatography (elution with a mixture of chloroform/methanol/acetic acid (9:1:1)) to obtain 8.4 g of a pale yellow resinous solid.

$^1$H-NMR(CDCl$_3$) δ: 0.88(3H,t,J=7 Hz,CH$_3$), 1.2-1.4(18H, m), 1.31(6H,s,(CH$_3$)$_2$C), 1.52(2H,m,NHCH$_2$C$\underline{H}_2$), 1.93(3H, s,CH$_3$COO$^-$), 3.29(2H,m,NHC$\underline{H}_2$CH$_2$), 4.49(2H,m,furfuryl), 6.17,6.27,7.29(each H,m,furfuryl), 8.22,8.59(each H,NH), 9.13,9.26(each H,br s,NH, NH$^+$).

Working Example 80

3,6-Dihydro-6,6-dimethyl-4-dodecylamino-2-(4-sulfamoylbenzylamino)-1,3,5-triazine 100 ml of methanol, 80 ml of acetone and 0.3 ml of concentrated hydrochloric acid were added to 5.5 g (10.0 mmol) of $N^1$-(4-sulfamoylbenzyl)-$N^5$-dodecyl-biguanide dihydrochloride. The mixture was refluxed for 22 hours, and the solvent was distilled off under reduced pressure. To the residue were added 60 ml of ethanol, 40 ml of water and 6.2 ml of 5N sodium hydroxide, and the mixture was refluxed for 1 hour, concentrated under reduced pressure, and extracted with ethyl acetate. The extract was washed with 10% aqueous sodium acetate, washed with water, and concentrated under reduced pressure to remove the solvent. The residue was recrystallized repeatedly from a mixture of methyl ethyl ketone and ethanol (8:2) and then from ethanol to obtain 1.4 g of colorless crystals having a melting point of 188 to 191° C.

$^1$H-NMR(CDCl$_3$) δ: 0.87(3H,t,J=7 Hz,CH$_3$), 1.0-1.6(20H, m), 1.40(6H,s,(CH$_3$)$_2$C), 3.26(2H,br dt-like,NHC$\underline{H}_2$), 4.49 (2H,m,ArCH$_2$), 7.16(2H,d,J=8 Hz,ArH), 7.60(2H,d,J=8 Hz,ArH).

Working Example 81

2-Amino-4-octylamino-1-(3-quinolyl)-1,6-dihydro-6,6-dimethyl-1,3,5-triazine dihydrochloride 150 ml of methanol, 120 ml of acetone and 0.5 ml of concentrated hydrochloric acid were added to 7.0 g (18.6 mmol) of $N^1$-(3-quinolyl)-$N^5$-octyl-biguanide dihydrochloride. The mixture was refluxed for 26 hours, and 1.8 ml of concentrated hydrochloric acid was further added thereto. The mixture was refluxed for 22 hours, and the solvent was distilled off under reduced pressure. The residue was purified by silica gel column chromatography (elution with a mixture of chloroform and methanol (9:1)) to obtain 5.3 g of a pale yellow powder.

$^1$H-NMR(CDCl$_3$-D$_2$O) δ: 0.79(3H,t,J=7 Hz,CH$_3$), 1.1-1.7 (12H,m), 1.63(6H,s,(CH$_3$)$_2$C), 3.41(2H,t,J=7 Hz,NHC$\underline{H}_2$), 7.6-9.3(6H,m,quinolyl).

Working Example 82

4-Octylamino-2-(3-quinolylamino)-3,6-dihydro-6,6-dimethyl-1,3,5-triazine acetate 60 ml of ethanol, 40 ml of water and 5.5 ml of 5N sodium hydroxide were added to 4.0 g (8.8 mmol) of the compound of Working Example 81. The mixture was refluxed for 1 hour, concentrated under reduced pressure, and extracted with ethyl acetate. The extract was washed with 10% aqueous sodium acetate, washed with water, and concentrated under reduced pressure to remove the solvent. The residue was recrystallized from methyl ethyl ketone and ether to obtain 2.5 g of pale yellow crystals having a melting point of 62 to 65° C.

$^1$H-NMR(CDCl$_3$-D$_2$O) δ: 0.81(3H,t,J=7 Hz,CH$_3$), 1.1-1.6 (12H,m), 1.48(6H,s,(CH$_3$)$_2$C), 2.06(3H,s,CH$_3$COO$^-$), 3.30 (2H,t,J=7 Hz,NHC$\underline{H}_2$), 7.4-9.0(6H,m,quinolyl).

Reference Example 1

$N^1$-(4-methoxybenzyl)-cyanoguanidine (Compound 9 in Preparation method 1 of Working Example 1)

800 ml of acetonitrile was added to 70.0 g (0.40 mol) of 4-methoxybenzylamine hydrochloride and 39.5 g (0.44 mol) of sodium dicyanamide. The mixture was refluxed for 19 hours, and the solvent was distilled off under reduced pressure. The residue was heated and dissolved in methanol, and insolubles were filtered off. The solvent was distilled off under reduced pressure, and the residue was recrystallized from ethyl acetate to obtain 67.0 g of colorless crystals having a melting point of 89 to 92° C.

$^1$H-NMR (DMSO-d$_6$) δ: 3.73(3H,s,CH$_3$O), 4.19(2H,d,J=6 Hz,ArCH$_2$), 6.71(1H,m,NH), 6.90(2H,d,J=9 Hz,ArH), 7.19 (2H,d,J=9 Hz,ArH), 7.1-7.3(1H,over lap,NH).

Reference Example 2

$N^1$-(4-methoxybenzyl)-$N^5$-decyl-biguanide dihydrochloride (Compound 11 in Preparation method 1 of Working Example 1)

40.0 g (0.17 mol) of the compound of Reference Example 1 and 27.4 g (0.17 mol) of 1-aminodecane were suspended in 660 ml of xylene, and 16 ml of concentrated hydrochloric acid was added thereto. Dean Stark (water fractional distillator) was attached thereto, and the mixture was refluxed for 8 hours, then concentrated under reduced pressure to remove the solvent. The residue was dissolved in 70% aqueous acetonitrile, and to the solution was added 28 ml of concentrated hydrochloric acid under ice-cooling. The resulting precipitated crystals were recrystallized from 70% aqueous acetonitrile to obtain 62.0 g of colorless crystals having a melting point of 222 to 224° C.

$^1$H-NMR (DMSO-d$_6$) δ: 0.86(3H,t,J=7 Hz,CH$_3$), 0.9-1.6 (16H,m), 3.15(2H,m,NHC$\underline{H}_2$), 3.74(3H,s,CH$_3$O), 4.38(2H, m,ArCH$_2$), 5.0-5.6(1H,br,NH), 6.92(2H,d,J=8 Hz,ArH), 7.32(2H,m,ArH), 8.4-9.6(3H,br,NH×3).

Reference Example 3

N$^1$-4-methoxyphenethyl-biguanide hydrochloride (Compound 15 in Preparation method 2 of Working Example 15)

200 ml of n-propanol was added to 30.0 g (0.16 mol) of 4-methoxyphenethylamine hydrochloride and 14.1 g (0.17 mol) of dicyanodiamide, and the mixture was refluxed for 24 hours, and cooled. The resulting precipitated crystals were filtered off, and the filtrate was concentrated and cooled. The precipitated crystals were recrystallized from n-propanol to obtain 22.6 g of colorless crystals having a melting point of 136 to 139° C.

$^1$H-NMR (DMSO-d$_6$) δ: 2.70(2H,t-like,ArC$\underline{H}_2$CH$_2$), 3.27 (2H,dt-like,ArCH$_2$C$\underline{H}_2$), 3.72(3H,s,CH$_3$O), 6.66(4H,m,NH), 6.87(2H,d,J=9 Hz,ArH), 6.7-7.1(2H,overlap,NH), 7.16(2H,d,J=9 Hz,ArH), 7.2-7.5(1H,br,NH$^+$).

Reference Example 4

N$^1$-hexyl-cyanoguanidine (Compound 9 in Preparation method 1 of Working Example 68)

300 ml of isopropyl alcohol was added to 49.0 g (0.36 mol) of 1-hexylamine hydrochloride and 35.0 g (0.39 mol) of sodium dicyanamide, and the mixture was refluxed for 20 hours. The solvent was distilled off under reduced pressure, and methanol was added to the residue. The mixture was heated, and insolubles were filtered off. The solvent was distilled off under reduced pressure, and dioxane was added to the residue. The mixture was heated, concentrated, and cooled to obtain 35.2 g of colorless crystals.

$^1$H-NMR (DMSO-d$_6$) δ: 0.86(3H,t,J=7 Hz,CH$_3$), 1.1-1.5 (8H,m), 3.02(2H,br dt-like NHC$\underline{H}_2$), 6.61(2H,m,NH×2), 7.77(1H,m,NH).

Reference Example 5

N$^1$-hexyl-N$^5$-octyl-biguanide dihydrochloride (Compound 11 in Preparation method 1 of Working Example 68)

10.0 g (59.4 mmol) of the compound of Reference Example 4 and 8.1 g (62.4 mmol) of 1-aminooctane were suspended in 200 ml of xylene, and 5.7 ml of concentrated hydrochloric acid was added thereto. Dean Stark (water fractional distillator) was attached thereto, and the mixture was refluxed for 8 hours. The solvent was distilled off under reduced pressure, and the residue was dissolved in 100 ml of 70% aqueous acetonitrile, and 9.9 ml of concentrated hydrochloric acid was added thereto. The solution was ice-cooled to obtain 16.2 g of colorless crystals.

$^1$H-NMR (DMSO-d$_6$,D$_2$O) δ: 0.87(6H,m,CH$_3$×2), 0.15-1.40(16H,m), 1.52(4H,m,NHCH$_2$C$\underline{H}_2$×2), 3.18(4H,t,J=7 Hz,NHC$\underline{H}_2$CH$_2$×2).

<Antibacterial Activity Test>

Regarding compounds obtained in respective Working Examples, in order to investigate antibacterial activity, minimal inhibitory concentration (MIC) was determined according to a standard method of Japanese Society of Chemotherapy.

As a test bacterium, nine kinds of *S. aureus* 209PJC, MRSA 97-115, MRSA KM 97-53, MRSA KM97-108, VRE 49, *E. coli* NIHJ JC-2, *P. aeruginosa* PAO-1, *P. aeruginosa* No. 12, *P. aeruginosa* KM97-5 were used and, as a medium, Mueller-Hinton Broth (DIFCO) was used. One platinum loop of a test bacterium was inoculated into 20 ml of a medium, and static culture was carried out at 37° C. for 16 to 20 hours, and then each bacterium species was diluted with a sterilized physiological saline to 10$^5$/ml, which was used as a test bacterium solution.

Then, each compound was dissolved in methanol, subjected to ½ stepwise dilution with a medium to prepare a medium for measuring sensitivity, and each 2 ml was dispensed into a test tube. A compound concentration in a medium was adjusted to 100 μg/ml and its 2$^n$-fold (n=−10 to 1). 25 μl of a test bacterium solution was inoculated into each sensitivity medium and, after cultured at 37° C. for 20 to 24 hours, determination was performed, and a minimum concentration at which growth was completely inhibited (minimal inhibitory concentration, MIC) was measured. As a control drug, a similar test was performed using 20% chlorhexidine gluconate solution (manufactured by Wako Pure Chemical Industries, Ltd.).

Test results are shown in the following Tables. Numerical values in Tables represent MIC expressed in μg/ml unit.

TABLE 1

| Bacterium strain | Compound | | | | | | |
|---|---|---|---|---|---|---|---|
| | Working Example 1 | Working Example 2 | Working Example 3 | Working Example 4 | Working Example 5 | Working Example 6 | Working Example 7 |
| *S. aureus* 209PJC | 0.4 | 0.4 | 1.6 | 0.4 | 0.5 | 0.9 | 0.2 |
| MRSA 97-115 | 0.4 | 0.8 | 1.6 | 0.8 | 0.9 | 1.8 | 0.8 |
| *E. coli* NIHJ JC-2 | 12.5 | 12.5 | 25 | 50 | 15 | 57 | 12.5 |
| *P. aeruginosa* PAO-1 | 25 | 50 | 50 | 50 | 30 | 114 | 50 |

TABLE 2

| Bacterium strain | Compound | | | | | | |
|---|---|---|---|---|---|---|---|
| | Working Example 8 | Working Example 9 | Working Example 10 | Working Example 11 | Working Example 12(1) | Working Example 12(2) | Working Example 13 |
| S. aureus 209PJC | 0.4 | 0.4 | 0.4 | 0.4 | 0.4 | 0.8 | 1.6 |
| MRSA 97-115 | 3.1 | 1.6 | 6.4 | 1.6 | 0.8 | 1.6 | 1.6 |
| E. coli NIHJ JC-2 | 25 | 100 | 12.8 | >100 | 25 | 50 | >100 |
| P. aeruginosa PAO-1 | >100 | >100 | 26 | >100 | 25 | 50 | >100 |

TABLE 3

| Bacterium strain | Compound | | | | | | |
|---|---|---|---|---|---|---|---|
| | Working Example 14 | Working Example 15(1) | Working Example 15(2) | Working Example 16(1) | Working Example 16(2) | Working Example 17 | Working Example 18(1) |
| S. aureus 209PJC | 3.1 | 0.4 | 0.4 | 0.4 | 0.4 | 0.8 | 0.4 |
| MRSA 97-115 | 3.1 | 1.6 | 1.6 | 1.6 | 1.6 | 1.6 | 0.8 |
| E. coli NIHJ JC-2 | 50 | 25 | 50 | 25 | 25 | 12.5 | 6.3 |
| P. aeruginosa PAO-1 | 100 | 50 | 50 | 50 | 25 | 25 | 25 |

TABLE 4

| Bacterium strain | Compound | | | | | | |
|---|---|---|---|---|---|---|---|
| | Working Example 18(2) | Working Example 19 | Working Example 20 | Working Example 21 | Working Example 22 | Working Example 23 | Working Example 24 |
| S. aureus 209PJC | 0.8 | 0.4 | 3.1 | 1.5 | 0.8 | 0.8 | 1.6 |
| MRSA 97-115 | 1.6 | 3.1 | 3.1 | 3.1 | 0.8 | 1.6 | 1.6 |
| E. coli NIHJ JC-2 | 6.3 | 50 | 50 | 25 | 25 | >100 | 50 |
| P. aeruginosa PAO-1 | 12.5 | 100 | 50 | 50 | 25 | >100 | 50 |

TABLE 5

| Bacterium strain | Compound | | | | | | |
|---|---|---|---|---|---|---|---|
| | Working Example 25 | Working Example 26 | Working Example 27 | Working Example 28 | Working Example 29 | Working Example 30 | Working Example 31 |
| S. aureus 209PJC | 1.6 | 3.1 | 1.6 | 1.6 | 0.8 | 1.6 | 1.6 |
| MRSA 97-115 | 1.6 | 6.3 | 1.6 | 3.1 | 1.6 | 3.1 | 3.1 |
| E. coli NIHJ JC-2 | 50 | 50 | 25 | 25 | >100 | 25 | 12.5 |
| P. aeruginosa PAO-1 | 100 | 50 | >100 | 50 | >100 | 50 | 25 |

TABLE 6

| Bacterium strain | Compound | | | | | | |
|---|---|---|---|---|---|---|---|
| | Working Example 32 | Working Example 33 | Working Example 34 | Working Example 35 | Working Example 36 | Working Example 37 | Working Example 38(2) |
| S. aureus 209PJC | 0.8 | 1.6 | 1.6 | 0.8 | 0.8 | 0.8 | 0.4 |
| MRSA 97-115 | 1.6 | 3.1 | 1.6 | 3.1 | 1.6 | 1.6 | 0.8 |
| E. coli NIHJ JC-2 | 25 | 25 | 50 | 25 | >100 | 12.5 | 25 |
| P. aeruginosa PAO-1 | 100 | 50 | 100 | 25 | >100 | 25 | 100 |

TABLE 7

| Bacterium strain | Compound | | | | | | |
|---|---|---|---|---|---|---|---|
| | Working Example 39 | Working Example 40 | Working Example 41(2) | Working Example 42 | Working Example 43(1) | Working Example 43(2) | Working Example 44 |
| S. aureus 209PJC | 0.4 | 0.4 | 0.4 | 0.8 | 0.4 | 0.8 | 0.2 |
| MRSA 97-115 | 0.8 | 0.8 | 0.8 | 1.6 | 0.8 | 1.6 | 0.8 |
| E. coli NIHJ JC-2 | 25 | 25 | 6.3 | 12.5 | 6.3 | 25 | 1.6 |
| P. aeruginosa PAO-1 | 50 | 25 | 12.5 | 12.5 | 25 | 25 | 12.5 |

TABLE 8

| Bacterium strain | Compound | | |
|---|---|---|---|
| | Working Example 45 | Working Example 46 | Working Example 47 |
| S. aureus 209PJC | 0.4 | 0.4 | 0.4 |
| MRSA 97-115 | 0.4 | 0.4 | 0.8 |
| E.coli NIHJ JC-2 | >100 | 12.5 | 12.5 |
| P. aeruginosa PAO-1 | >100 | 25 | 12.5 |

TABLE 9

| Bacterium strain | Compound | | | | | | |
|---|---|---|---|---|---|---|---|
| | Working Example 48 | Working Example 49 | Working Example 50 | Working Example 51 | Working Example 52 | Working Example 53 | Working Example 54 |
| S. aureus 209PJC | 0.8 | 0.4 | 0.4 | 0.4 | 0.8 | 1.6 | 0.8 |
| MRSA 97-115 | 1.6 | 0.8 | 0.4 | 0.8 | 1.6 | 3.1 | 1.6 |
| E. coli NIHJ JC-2 | 12.5 | 12.5 | 12.5 | 50 | 12.5 | 50 | 50 |
| P. aeruginosa PAO-1 | 12.5 | 25 | 25 | 100 | 25 | 100 | 100 |

TABLE 10

| Bacterium strain | Compound | | | | | | |
|---|---|---|---|---|---|---|---|
| | Working Example 55 | Working Example 56 | Working Example 57 | Working Example 58 | Working Example 59 | Working Example 60 | Working Example 61 |
| S. aureus 209PJC | 0.4 | 0.4 | 0.8 | 0.4 | 0.8 | 3.1 | 6.3 |
| MRSA 97-115 | 0.8 | 0.8 | 1.6 | 0.4 | 1.6 | 6.3 | 6.3 |
| E. coli NIHJ JC-2 | 12.5 | 12.5 | 25 | 12.5 | 25 | >100 | >100 |
| P. aeruginosa PAO-1 | 50 | 12.5 | 25 | 12.5 | 50 | >100 | >100 |

TABLE 11

| Bacterium strain | Compound | | | | | | |
|---|---|---|---|---|---|---|---|
| | Working Example 62 | Working Example 63 | Working Example 64 | Working Example 65 | Working Example 66 | Working Example 67 | Working Example 68 |
| S. aureus 209PJC | 0.8 | 6.3 | 0.8 | 0.8 | 0.8 | 0.8 | 0.8 |
| MRSA 97-115 | 0.8 | 6.3 | 0.8 | 0.8 | 1.6 | 1.6 | 0.8 |
| E. coli NIHJ JC-2 | 12.5 | 100 | 25 | 25 | 100 | 100 | 12.5 |
| P. aeruginosa PAO-1 | 12.5 | 100 | 25 | 50 | >100 | 100 | 50 |

TABLE 12

| Bacterium strain | Compound | | | | | | | |
|---|---|---|---|---|---|---|---|---|
| | Working Example 69 | Working Example 70 | Working Example 71 | Working Example 72 | Working Example 73 | Working Example 74 | Working Example 75 | Working Example 76 |
| S. aureus 209PJC | 0.8 | 0.8 | 0.8 | 0.8 | 0.8 | 0.8 | 0.8 | 0.8 |
| MRSA 97-115 | 0.8 | 1.6 | 0.8 | 1.6 | 1.6 | 0.8 | 3.1 | 1.6 |
| E. coli NIHJ JC-2 | 12.5 | 25 | 100 | 25 | 12.5 | 12.5 | 25 | 25 |
| P. aeruginosa PAO-1 | 50 | 25 | 100 | 25 | 50 | 100 | 50 | 50 |

TABLE 13

| Bacterium strain | Compound | | | | |
|---|---|---|---|---|---|
| | Working Example 79 | Working Example 80 | Working Example 81 | Working Example 82 | Control drug |
| S. aureus 209PJC | 0.8 | 0.4 | 0.8 | 0.8 | 0.2 |
| MRSA 97-115 | 1.6 | 1.6 | 1.6 | 1.6 | 3.1 |
| E. coli NIHJ JC-2 | 50 | >100 | 12.5 | 25 | 1.6 |
| P. aeruginosa PAO-1 | 100 | >100 | 50 | 50 | 50 |

TABLE 14

| Bacterium strain | Working Example 48 | Working Example 58 | Working Example 68 | Control drug |
|---|---|---|---|---|
| MRSA KM 97-53 | 0.8 | 1.6 | 1.6 | 3.1 |
| MRSA KM 97-108 | 1.6 | 1.6 | 1.6 | 3.1 |
| VRE 49 | 0.8 | 1.6 | 1.6 | 3.1 |
| P. aeruginosa No. 12 | 25 | 25 | 50 | 12.5 |
| P. aeruginosa KM 97-5 | 25 | 25 | 50 | 12.5 |

<Bactericidal Activity Test>

Regarding compounds of Working Examples 1, 2, 4, 15 (1), 22, 31, 37, 38 (2), 43 (1), 43 (2), 48, 49, 56, 58, 65, 68, 69, 72 and 82 and a control drug, bactericidal activity was evaluated using a phenol coefficient measuring method.

As a test bacterium, the same bacteria species as those of the antibacterial activity test were used; as a medium to be used, a SCD medium (manufactured by Eiken Chemical Co., Ltd.) was used for pre-culture medium; and a heart infusion bouillon medium (manufactured by Eiken Chemical Co., Ltd.) was used as a medium for growing a live bacterium in a test solution after bactericidal treatment. One platinum loop of a test bacterium was inoculated into 20 ml of a medium, and static culture was carried out at 37° C. for 18 to 20 hours, and the cells were adjusted with a sterilized physiological saline to $1 \times 10^7$/ml, which was used as a test bacterium solution.

Then, a solution of each compound in methanol was subjected to ½ stepwise dilution with sterilized water, each 5 ml was dispensed into a test tube, 0.5 ml of the previously prepared test bacterium solution was added thereto, and the mixture was blended well. After 1 minute, 3 minutes and 5 minutes has passed, 5 μl of the test solution was collected and inoculated into 2 ml of a heart infusion bouillon medium, this was cultured at 37° C. for 40 to 48 hours, and the presence or absence of growth of a bacterium was determined. A test was performed three times, a minimum concentration at which growth of a bacterium was not recognized two or more times was adopted as a minimal bactericidal concentration (MBC value). A 20% chlorhexidine gluconate solution (manufactured by Wako Pure Chemical Industries, Ltd.) was used as a control drug to perform the similar test.

Test results are shown in the following Tables. Numerical values in Tables represent MBC expressed in μg/ml unit.

TABLE 15

| Bacterium strain | Working Example 1 | | | Working Example 2 | | | Working Example 4 | | |
|---|---|---|---|---|---|---|---|---|---|
| | 1 min | 3 min | 5 min | 1 min | 3 min | 5 min | 1 min | 3 min | 5 min |
| S. aureus 209PJC | 6.3 | 3.1 | 3.1 | 12.5 | 6.3 | 3.1 | 50 | 12.5 | 6.3 |
| MRSA 97-115 | 25 | 6.3 | 6.3 | 25 | 12.5 | 6.3 | 25 | 6.3 | 6.3 |
| E. coli NIHJ JC-2 | 6.1 | 3.1 | 1.6 | 6.3 | 3.1 | 3.1 | 3.1 | 1.6 | 1.6 |
| P. aeruginosa PAO-1 | 1.6 | 0.8 | 0.8 | 3.1 | 1.6 | 1.6 | 3.1 | 3.1 | 1.6 |

TABLE 16

| Bacterium strain | Working Example 15(1) | | | Working Example 22 | | |
|---|---|---|---|---|---|---|
| | 1 min | 3 min | 5 min | 1 min | 3 min | 5 min |
| S. aureus 209PJC | 12.5 | 3.1 | 3.1 | 12.5 | 6.3 | 6.3 |
| MRSA 97-115 | 25 | 12.5 | 6.3 | 25 | 25 | 12.5 |
| E. coli NIHJ JC-2 | 6.3 | 3.1 | 1.6 | 6.3 | 6.3 | 6.3 |
| P. aeruginosa PAO-1 | 6.3 | 3.1 | 3.1 | 12.5 | 3.1 | 3.1 |

TABLE 17

| Bacterium strain | Working Example 31 | | | Working Example 37 | | | Working Example 38(2) | | |
|---|---|---|---|---|---|---|---|---|---|
| | 1 min | 3 min | 5 min | 1 min | 3 min | 5 min | 1 min | 3 min | 5 min |
| S. aureus 209PJC | 25 | 12.5 | 12.5 | 12.5 | 6.3 | 6.3 | 12.5 | 6.3 | 3.1 |
| MRSA 97-115 | 25 | 12.5 | 6.3 | 25 | 25 | 12.5 | 25 | 12.5 | 12.5 |
| E. coli NIHJ JC-2 | 12.5 | 12.5 | 6.3 | 12.5 | 6.3 | 3.1 | 6.3 | 3.1 | 3.1 |
| P. aeruginosa PAO-1 | 12.5 | 12.5 | 6.3 | 3.1 | 3.1 | 3.1 | 6.3 | 3.1 | 1.6 |

TABLE 18

| Bacterium strain | Working Example 43(1) | | | Working Example 43(2) | | |
|---|---|---|---|---|---|---|
| | 1 min | 3 min | 5 min | 1 min | 3 min | 5 min |
| S. aureus 209PJC | 25 | 6.3 | 6.3 | 25 | 6.3 | 6.3 |
| MRSA 97-115 | 50 | 25 | 12.5 | >50 | 25 | 25 |
| E. coli NIHJ JC-2 | 12.5 | 6.3 | 3.1 | 12.5 | 6.3 | 6.3 |
| P. aeruginosa PAO-1 | 3.1 | 3.1 | 3.1 | 12.5 | 6.3 | 6.3 |

TABLE 19

| Bacterium strain | Working Example 48 | | | Working Example 49 | | | Working Example 56 | | |
|---|---|---|---|---|---|---|---|---|---|
| | 1 min | 3 min | 5 min | 1 min | 3 min | 5 min | 1 min | 3 min | 5 min |
| S. aureus 209PJC | 12.5 | 6.3 | 6.3 | 12.5 | 6.3 | 6.3 | 25 | 12.5 | 6.3 |
| MRSA 97-115 | 12.5 | 6.3 | 6.3 | 25 | 12.5 | 12.5 | 25 | 12.5 | 6.3 |
| E. coli NIHJ JC-2 | 6.3 | 6.3 | 3.1 | 12.5 | 6.3 | 3.1 | 12.5 | 3.1 | 3.1 |
| P. aeruginosa PAO-1 | 6.3 | 3.1 | 3.1 | 12.5 | 3.1 | 3.1 | 12.5 | 3.1 | 1.6 |

TABLE 20

| Bacterium strain | Working Example 58 | | | Working Example 65 | | | Working Example 68 | | |
|---|---|---|---|---|---|---|---|---|---|
| | 1 min | 3 min | 5 min | 1 min | 3 min | 5 min | 1 min | 3 min | 5 min |
| S. aureus 209PJC | 6.3 | 3.1 | 3.1 | 12.5 | 3.1 | 3.1 | 12.5 | 6.3 | 6.3 |
| MRSA 97-115 | 25 | 25 | 12.5 | 25 | 12.5 | 12.5 | 12.5 | 6.3 | 6.3 |
| E. coli NIHJ JC-2 | 12.5 | 6.3 | 6.3 | 3.1 | 1.6 | 1.6 | 12.5 | 6.3 | 6.3 |
| P. aeruginosa PAO-1 | 12.5 | 6.3 | 3.1 | 3.1 | 1.6 | 1.6 | 6.3 | 3.1 | 1.6 |

TABLE 21

| Bacterium strain | Working Example 69 | | | Working Example 72 | | | 
|---|---|---|---|---|---|---|
| | 1 min | 3 min | 5 min | 1 min | 3 min | 5 min |
| S. aureus 209PJC | 6.3 | 6.3 | 3.1 | 3.1 | 1.6 | 1.6 |
| MRSA 97-115 | 25 | 25 | 12.5 | 25 | 12.5 | 12.5 |
| E. coli NIHJ JC-2 | 6.3 | 3.1 | 3.1 | 6.3 | 3.1 | 3.1 |
| P. aeruginosa PAO-1 | 3.1 | 1.6 | 1.6 | 3.1 | 1.6 | 1.6 |

TABLE 22

| Bacterium strain | Working Example 82 | | | Control drug | | |
|---|---|---|---|---|---|---|
| | 1 min | 3 min | 5 min | 1 min | 3 min | 5 min |
| S. aureus 209PJC | 12.5 | 6.3 | 6.3 | 62.5 | 62.5 | 62.5 |
| MRSA 97-115 | 50 | 25 | 25 | 1000 | 250 | 125 |
| E. coli NIHJ JC-2 | 6.3 | 6.3 | 3.1 | 62.5 | 31.3 | 15.6 |
| P. aeruginosa PAO-1 | 12.5 | 12.5 | 6.3 | >400 | >400 | >400 |

TABLE 23

| Bacterium strain | Working Example 48 | | | Working Example 58 | | |
|---|---|---|---|---|---|---|
| | 1 min | 3 min | 5 min | 1 min | 3 min | 5 min |
| MRSA KM 97-53 | 50 | 25 | 25 | 50 | 50 | 25 |
| MRSA KM 97-108 | 50 | 50 | 25 | 50 | 50 | 25 |
| VRE 49 | 25 | 12.5 | 12.5 | 25 | 25 | 12.5 |
| P. aeruginosa No. 12 | 25 | 12.5 | 12.5 | 6.3 | 6.3 | 3.1 |
| P. aeruginosa KM 97-5 | 3.1 | 3.1 | 3.1 | 6.3 | 3.1 | 3.1 |

TABLE 24

| Bacterium strain | Working Example 68 | | | Control drug | | |
|---|---|---|---|---|---|---|
| | 1 min | 3 min | 5 min | 1 min | 3 min | 5 min |
| MRSA KM 97-53 | 50 | 25 | 25 | 500 | 250 | 250 |
| MRSA KM 97-108 | 50 | 25 | 25 | 500 | 500 | 500 |
| VRE 49 | 25 | 25 | 12.5 | >1000 | >1000 | >1000 |
| P. aeruginosa No. 12 | 3.1 | 3.1 | 1.6 | 125 | 32 | 32 |
| P. aeruginosa KM 97-5 | 12.5 | 6.3 | 6.3 | 31 | 16 | 8 |

INDUSTRIAL APPLICABILITY

Since the compound (1) which is an active ingredient of the present invention has strong antibacterial activity and bactericidal activity, it is extremely useful as an antibacterial agent or a bactericidal/disinfectant agent.

The invention claimed is:

1. A dihydrotriazine compound represented by the formula (1a):

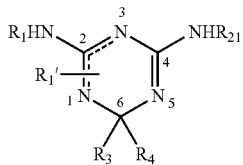

wherein
$R_1$ is (i) a phenyl group, (ii) a benzyl or 2-phenylethyl group which is optionally substituted by methyl or methoxy, (iii) a quinolyl group or (iv) a cyclohexylmethyl group; $R_{21}$ is n-octyl, n-nonyl or n-decyl; $R_3$ and $R_4$ are each methyl; and $R_1'$ is a hydrogen atom attached to the nitrogen atom at position 1 or 3 of the dihydrotriazine ring, or a tautomer thereof or a salt thereof.

2. The dihydrotriazine compound according to claim 1, wherein $R_1$ is (i) a phenyl group or (ii) a benzyl or 2-phenylethyl group which is optionally substituted by methyl or methoxy, or a tautomer thereof or a salt thereof.

3. The dihydrotriazine compound according to claim 1, which is 4-octylamino-3,6-dihydro-6,6-dimethyl-2-(4'-methylbenzylamino)-1,3,5-triazine, or a tautomer thereof or a salt thereof.

4. The dihydrotriazine compound according to claim 1, which is 4-octylamino-2-cyclohexylmethylamino-3,6-dihydro-6,6-dimethyl-1,3,5-triazine or a tautomer thereof or a salt thereof.

5. A method for sterilizing/disinfecting, which comprises applying externally an effective amount of the dihydrotriazine compound as defined in claim 1, or a tautomer thereof or a salt thereof, to a wound site, a burn site or a bedsore site, or an operation site before and after operation, a hand or an arm of a medical employee, or sterilizing or disinfecting medical equipment or a medical environment in need of sterilization/disinfection.

6. A method of preparation of an external bactericidal/disinfectant agent, which comprises mixing the dihydrotriazine compound represented by the formula (1a) as defined in claim 1, or a tautomer thereof or a pharmacologically acceptable salt thereof together with a pharmaceutically acceptable additive.

* * * * *